US009126969B2

(12) United States Patent
Cherrier et al.

(10) Patent No.: US 9,126,969 B2
(45) Date of Patent: Sep. 8, 2015

(54) PYRAZOLYLBENZIMIDAZOLE DERIVATIVES, COMPOSITIONS CONTAINING THEM AND USE THEREOF

(75) Inventors: Marie-Pierre Cherrier, Antony (FR); Eric Parmantier, Antony (FR); Hervé Minoux, Antony (FR); François Clerc, Antony (FR); Odile Angouillant-Boniface, Antony (FR); Maurice Brollo, Antony (FR); Laurent Schio, Antony (FR)

(73) Assignee: AVENTIS PHARMA S.A., Antony (FR)

( * ) Notice: Subject to any disclaimer, the term of this patent is extended or adjusted under 35 U.S.C. 154(b) by 1377 days.

(21) Appl. No.: 12/338,176

(22) Filed: Dec. 18, 2008

(65) Prior Publication Data

US 2009/0197866 A1 Aug. 6, 2009

Related U.S. Application Data

(63) Continuation of application No. PCT/FR2007/001126, filed on Jul. 3, 2007.

(30) Foreign Application Priority Data

Jul. 4, 2006 (FR) ..................................... 06 06064

(51) Int. Cl.

| | |
|---|---|
| ***C07D 413/14*** | (2006.01) |
| ***C07D 401/14*** | (2006.01) |
| ***C07D 235/04*** | (2006.01) |
| ***C07D 403/04*** | (2006.01) |
| ***C07D 403/14*** | (2006.01) |
| ***C07D 405/14*** | (2006.01) |

(52) U.S. Cl.

CPC ............ *C07D 403/04* (2013.01); *C07D 235/04* (2013.01); *C07D 401/14* (2013.01); *C07D 403/14* (2013.01); *C07D 405/14* (2013.01); *C07D 413/14* (2013.01)

(58) Field of Classification Search

CPC ... C07D 412/14; C07D 401/14; C07D 235/04
See application file for complete search history.

(56) References Cited

U.S. PATENT DOCUMENTS

| | | | |
|---|---|---|---|
| 6,897,208 | B2 | 5/2005 | Edwards et al. |
| 2006/0014756 | A1 | 1/2006 | Edwards et al. |
| 2008/0125418 | A1 | 5/2008 | Babin et al. |

FOREIGN PATENT DOCUMENTS

| | | | |
|---|---|---|---|
| WO | WO 03/035065 A1 | | 5/2003 |
| WO | WO 03/035644 | | 5/2003 |
| WO | WO 2005/002552 A2 | | 1/2005 |
| WO | WO 2006/070202 A1 | | 7/2006 |
| WO | WO 2008001115 A2 | * | 1/2008 |

OTHER PUBLICATIONS

Vippagunta et al. Advanced Drug Delivery Reviews, 2001, vol. 48, pp. 3-26.*

* cited by examiner

*Primary Examiner* — Samira Jean-Louis
(74) *Attorney, Agent, or Firm* — Morrison & Foerster LLP

(57) ABSTRACT

The disclosure relates to compounds of formula (I):

(I)

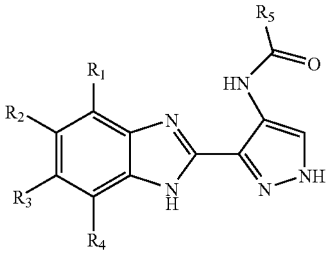

wherein $R_1$, $R_2$, $R_3$, $R_4$, and $R_5$ are as defined in the disclosure, to the compositions containing them and to the use thereof as medicaments, in particular as anticancer agents. The disclosure also relates to the process for preparing the compounds of formula (I) and to reaction intermediates.

14 Claims, No Drawings

PYRAZOLYLBENZIMIDAZOLE DERIVATIVES, COMPOSITIONS CONTAINING THEM AND USE THEREOF

This application is a continuation of International application No. PCT/FR2007/001126, filed Jul. 3, 2007, which is incorporated herein by reference in its entirety; which claims the benefit of priority of French Patent Application No. 0 606 064, filed Jul. 4, 2006.

The present invention relates to pyrazolylbenzimidazole derivatives, to the compositions containing them and to the use thereof as medicaments, in particular as an anticancer agent via the inhibition of tumor cell proliferation. The invention also relates to the process for preparing these derivatives and also to some of the reaction intermediates.

TECHNICAL FIELD

To date, most of the commercial products used in chemotherapy are cytotoxic compounds which pose significant problems of side effects and of tolerance by the patients. These effects could be limited insofar as the medicaments used act selectively on the cancerous cells, with the exclusion of the healthy cells. One of the solutions for limiting the adverse effects of chemotherapy may therefore comprise the use of medicaments that act on metabolic pathways or elements constituting these pathways, expressed predominantly in cancer cells and which are expressed little or not at all in healthy cells. It is also desired for the compounds, when they are administered in liquid form, to have sufficient solubility in an aqueous medium, in particular at a standard pH of 7.4.

A technical problem that the invention is intended to solve is therefore that of improving the enzyme and cell selectivity of chemical compounds while at the same time maintaining an acceptable anticancer activity on tumor cell lines.

PRIOR ART

International applications WO 03/035065 and WO 03/035644 describe very broadly benzimidazoles and analogs thereof as kinase inhibitors. International application WO 2005/002552 describes pyrazole compounds which, according to one particular embodiment, may be benzimidazoles that can be used as kinase inhibitors. However, the compounds disclosed in these documents do not appear to have an optimized medicament candidate profile: in fact, when they are tested, some of the compounds exhibit activities on certain kinases and/or certain cell lines that are unfavorable in terms of side effects that may result from this profile. Against all expectations, and this is what forms the subject matter of the present invention, it has been found that it is possible to improve the enzyme and cell selectivity of pyrazolylbenzimidazoles while at the same time maintaining an acceptable anticancer activity on tumor cell lines.

International application WO 2006/070202 describes benzimidazol-pyrazole compounds which act as kinase inhibitors, for which one of the substitutents on the benzimidazolering is —OMe or —$CH_2$-morpholine, —$CH_2$-piperazine or —$CH_2$-piperazine-Me. None of these applications describes the compounds of the present invention.

DESCRIPTION OF THE INVENTION

The present application claims the priority of prior French application No. 0606064 filed on 4 Jul. 2006, which is entirely incorporated herein by way of reference.

DEFINITIONS USED

Unless otherwise mentioned, the following definitions have been used in the present application:

- halogen: a fluorine, chlorine, bromine or iodine atom;
- alkyl: linear or branched, saturated aliphatic hydrocarbon-based group containing at most 12 carbon atoms. It is chosen, for example, from methyl, ethyl, propyl, isopropyl, butyl, isobutyl, sec-butyl, tert-butyl, pentyl, isopentyl, sec-pentyl, tert-pentyl, neopentyl, hexyl, isohexyl, sec-hexyl, tert-hexyl and also heptyl, octyl, nonyl, decyl, undecyl and dodecyl radicals, and also the linear or branched positional isomers thereof. Preferably, they contain at most six carbon atoms;
- alkyloxy: —O-alkyl radical, in which the alkyl radical has the meaning indicated above. It is chosen, for example, from methoxy, ethoxy, propoxy, isopropoxy, linear, secondary or tertiary butoxy, pentoxy, hexoxy and heptoxy radicals, and also the linear or branched positional isomers thereof;
- cycloalkyl: monocyclic or bicyclic carbocyclic radical containing from 3 to 10 ring members. For example, the cycloalkyl radicals are cyclopropyl (Cy), cyclobutyl, cyclopentyl and cyclohexyl radicals;
- aryl: an unsaturated carbocyclic radical which is monocyclic or comprises condensed rings. Mention may, for example, be made of phenyl or naphthyl radicals. Mention is more particularly made of the phenyl radical;
- aryloxy: an O-aryl radical in which the aryl radical has the meaning indicated above;
- heterocycloalkyl: a saturated carbocyclic radical comprising at most seven ring members interrupted with one or more heteroatoms, which may be identical or different, chosen from oxygen, nitrogen or sulfur atoms. As examples of heterocycloalkyl radicals, mention may in particular be made of dioxolane, dioxane, dithiolane, thiooxolane, thiooxane, oxiranyl, oxolanyl, dioxolanyl, piperazinyl, piperidinyl, pyrrolidinyl, imidazolidinyl, pyrazolidinyl, morpholinyl or else tetrahydrofuryl, tetrahydrothienyl, chromanyl, dihydrobenzofuranyl, indolinyl, piperidinyl, perhydropyranyl, pyrindolinyl, tetrahydro-quinolinyl, tetrahydroisoquinolinyl or thioazolidinyl radicals, all these radicals being optionally substituted. Among the heterocycloalkyl radicals, mention may more particularly be made of optionally substituted piperazinyl, optionally substituted piperidinyl, optionally substituted pyrrolidinyl, imidazolidinyl, pyrazolidinyl, morpholinyl or thioazolidinyl radicals;
- heteroaryl: a partially or completely unsaturated carbocyclic radical comprising at most seven ring members interrupted with one or more heteroatoms, which may be identical or different, chosen from oxygen, nitrogen or sulfur atoms. Among the five-membered heteroaryl radicals, mention may, for example, be made of the following radicals: furyl, such as 2-furyl, thienyl, such as 2-thienyl and 3-thienyl, pyrrolyl, diazolyl, thiazolyl, thiadiazolyl, thiatriazolyl, isothiazolyl, oxazolyl, oxadiazolyl, 3- or 4-isoxazolyl, imidazolyl, pyrazolyl and isoxazolyl. Among the six-membered heteroaryl radicals, mention may in particular be made of pyridyl, such as 2-, 3- and 4-pyridyl, pyrimidyl, pyrimidinyl, pyridazinyl, pyrazinyl and tetrazolyl radicals. As condensed heteroaryl radicals containing at least one heteroatom chosen from sulfur, nitrogen and oxygen, mention may, for example, be made of benzothienyl, such as 3-benzothienyl, benzofuryl, benzofuranyl, benzo-pyrrolyl, benzimidazolyl, benzoxazolyl, thio-naphthyl, indolyl, purinyl, quinolinyl, isoquinolinyl and naphthyridinyl. Among the condensed heteroaryl radicals, mention may more particularly be made of benzothienyl, benzofuranyl, indolyl or quinolinyl, benzimidazolyl, benzothiazolyl, furyl, imidazolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, 1,3,4-thiadiazolyl, thiazolyl and thienyl radicals and triazolyl groups, these radicals being optionally substituted as indicated for the heteroaryl radicals;

acyl: an R—C(═O)— radical containing at most 12 carbon atoms, in which the R radical is an alkyl, cycloalkyl, heterocycloalkyl, aryl or heteroaryl radical, these radicals having the meanings indicated above and being optionally substituted as indicated above. Formyl, acetyl, propionyl, butyryl or benzoyl, or alternatively valeryl, hexanoyl, acryloyl, crotonoyl or carbamoyl, radicals are, for example, mentioned;

substituted: refers to the presence of one or more conventional substituent(s) of organic chemistry which are known to those skilled in the art. They are, in particular, the following substituents: halogen, alkyl, cycloalkyl, hydroxyl, alkyloxy, aryloxy, amino, alkylamino, dialkylamino, acyl or phenyl.

Compounds of the Invention

The compounds of the present invention correspond to general formula (I) below:

(I)

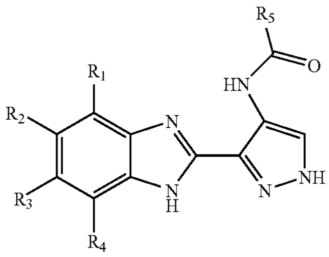

in which:

$R_1$ and $R_4$ are independently selected from the group comprising: H, Me, Et, $CO_2R_c$, $CH_2OR_c$, $OR_c$, F, Cl and $C(═O)NHR_d$; in which $R_c$ is chosen from H, $(C_1-C_6)$alkyl, substituted $(C_1-C_6)$alkyl, $(C_3-C_7)$-cycloalkyl, substituted $(C_3-C_7)$cycloalkyl, aryl, substituted aryl, heteroaryl and substituted heteroaryl; and in which $R_d$ is chosen from H, $(C_1-C_6)$alkyl, substituted $(C_1-C_6)$alkyl, $(C_3-C_7)$cycloalkyl, substituted $(C_3-C_7)$cycloalkyl, and optionally substituted $(C_3-C_7)$heterocycloalkyl comprising from 1 to 3 heteroatoms chosen from N, O and S;

$R_2$ and $R_3$ are selected from the group comprising H, F, $OR_e$ and $NR_eR_f$, with the exception of methoxy and ethoxy, in which:

(i) $R_e$ and $R_f$ are independently selected from the group comprising: H, $(C_1-C_6)$alkyl, $(C_1-C_6)$alkyl substituted with a substituent selected from the group comprising: $OR_g$, $NR_hR_j$, $(C_3-C_7)$cycloalkyl and substituted $(C_3-C_7)$cycloalkyl, in which:

(a) $R_g$, $R_h$ and $R_j$ are independently selected from the group comprising: H, $(C_1-C_6)$alkyl and substituted $(C_1-C_6)$alkyl, or (b) $R_g$ is selected from the group comprising: H, $(C_1-C_6)$alkyl and substituted $(C_1-C_6)$alkyl and $R_h$ and $R_j$ form a ring containing one to three heteroatoms chosen from N, O and S, or (ii) $R_e$ and $R_f$ form an optionally substituted heterocycle containing from one to three heteroatoms chosen from N, O and S;

$R_5$ is selected from the group comprising NMeEt, $NH(^iPr)$, $NEt_2$, $N(^iPr_2)$, $NEt(^iPr)$, pyrrolidinyl, piperidinyl, morpholinyl, N-methylpiperazinyl, NHCy, $NCy_2$, $NMe(^iPr)$, $NH(^tBu)$, $NH(^tBu)$, $N(^nBu)_2$, piperazinyl, NH(Et), $N(^nPr)_2$ and $NEt(^iPr)$.

In formula I, $R_5$ is therefore connected to the C═O group via a nitrogen atom. It is selected more particularly from the group comprising: NMeEt, $NH(^iPr)$, $NEt_2$, $N(^iPr)_2$, $NEt(^iPr)$, pyrrolidinyl, piperidinyl, morpholinyl, N-methylpiperazinyl, NHCy and $NCy_2$.

A subject of the invention is in particular the compounds of formula (I) for which:

either $R_2$ is H or F and $R_3$ is $OR_e$ or $NR_eR_f$, or $R_3$ is H or F and $R_2$ is $OR_e$ or $NR_eR_f$.

$R_2/R_3$ in the form $OR_e$ or $NR_eR_f$ may be one of those described in table I. Mention will, for example, be made of: morpholinyl, homomorpholinyl, $—O(CH_2)_m$piperidinyl with n=2, 3 or 4, $—O(CH_2)_nN(Me)_2$ with n=2, 3 or 4, —N-methylpiperazinyl and —N-methylhomopiperazinyl, $—NH(CH_2)_2NMe_2$. By virtue of the definition of $R_2$ and $R_3$, the following compounds, which are described in WO 03/035065, are therefore excluded from the present application:

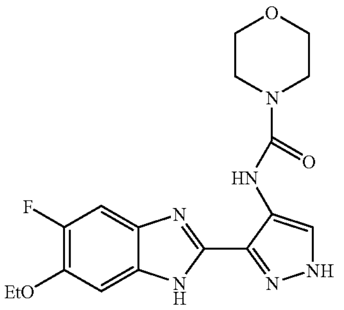

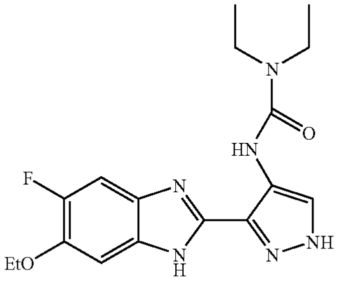

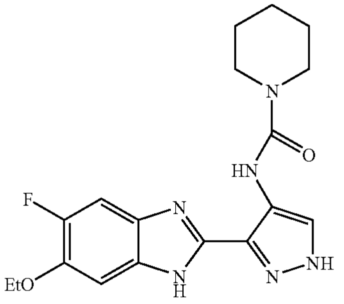

Preferably, a subject of the invention is the compounds of formula (I) in which:

when $R_2$ is F, $R_3$ is advantageously chosen from morpholinyl, homomorpholinyl, $O(CH_2)$ piperidinyl with n=2, 3 or 4, $O(CH_2)_nNMe_2$ with n=2, 3 or 4, N-methylpiperazinyl and N-methylhomopiperazinyl, and $R_5$ is NH($^i$Pr), NHEt, $NEt_2$, N($^i$Pr)$_2$, NEt($^i$Pr), pyrrolidinyl, piperidinyl or morpholinyl;

when $R_3$ is F, $R_2$ is advantageously chosen from morpholinyl, homomorpholinyl, $O(CH_2)$ piperidinyl with n=2, 3 or 4, $O(CH_2)_nNMe_2$ with n=2, 3 or 4, N-methylpiperazinyl and N-methylhomopiperazinyl, and $R_5$ is NH($^i$Pr), NHEt, $NEt_2$, N($^i$Pr)$_2$, NEt($^i$Pr), pyrrolidinyl, piperidinyl or morpholinyl.

More particularly, $R_1$ and $R_4$ both denote H.

A subject of the invention is also the compounds of formula (Ia):

(Ia)

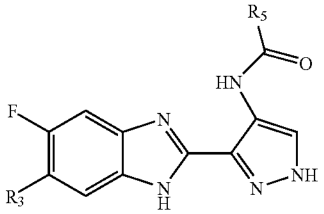

in which $R_3$ is as defined above, with the exception of OMe and OEt, and $R_5$ is NH($^i$Pr), NHEt, $NEt_2$, N($^i$Pr)$_2$, NEt($^i$Pr), pyrrolidinyl, piperidinyl or morpholinyl.

Most particularly, $R_3$ is morpholinyl, homomorpholinyl, —$O(CH_2)_n$piperidinyl with n=2, 3 or 4, —$O(CH_2)_nNMe_2$ with n=2, 3 or 4, N-methylpiperazinyl or N-methylhomopiperazinyl, and $R_5$ is $NEt_2$ or piperidinyl.

It is understood that a subject of the invention is also the compounds of formula (Ib):

(Ib)

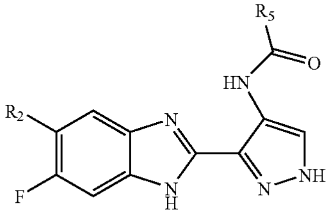

which corresponds to the compounds of formula (Ia) with a 180-degree rotation of the benzimidazole (and delocalization of the double bond). A subject of the invention is also the tautomeric forms of the pyrazole ring of the compounds of formula (Ia) or (Ib).

A subject of the invention is most particularly a compound of formula (Ia) or (Ib) in which $R_2$ or $R_3$ are chosen from —$O(CH_2)_nNMe_2$ with n=2, 3 or 4 (preferably 3), N-methylpiperazinyl, N-methylhomopiperazinyl, morpholin-4-yl and homomorpholinyl.

A subject of the invention is most particularly a compound of formula (Ia) or (Ib) in which $R_5$ is piperidin-1-yl.

The compounds according to the invention may be in a form which is: nonchiral, or racemic, or enriched in one stereoisomer, or enriched in one enantiomer; in all the tautomeric and optionally salified forms thereof.

The compounds of the invention may be optionally converted to addition salts with an inorganic or organic acid by the action of such an acid in an organic solvent such as an alcohol, a ketone, an ether or a chlorinated solvent. These salts are also part of the invention. As examples of pharmaceutically acceptable salts, the following salts may be mentioned: benzenesulfonate, hydrobromide, hydrochloride, citrate, ethanesulfonate, fumarate, gluconate, iodate, maleate, isethionate, methanesulfonate, methylenebis-b-oxynaphthoate, nitrate, oxalate, pamoate, phosphate, salicylate, succinate, sulfate, tartrate, theophylline acetate and p-toluenesulfonate.

According to a second aspect, the invention relates to a medicament, comprising a compound according to the invention, or an addition salt of this compound with a pharmaceutically acceptable acid, or else a hydrate or a solvate of said compound.

Pharmaceutical Composition

According to a third aspect, the invention also relates to a pharmaceutical composition comprising a compound according to the invention, in combination with a pharmaceutically acceptable excipient according to the method of administration chosen. The pharmaceutical composition may be in solid or liquid form or in the form of liposomes.

Among the solid compositions, mention may be made of powders, gel capsules and tablets. Among the oral forms, solid forms protected with respect to the acidic medium of the stomach may also be included. The carriers used for the solid forms in particular comprise inorganic carriers such as phosphates or carbonates, or organic carriers such as lactose, celluloses, starch or polymers. The liquid forms comprise solutions, suspensions or dispersions. They contain, as dispersive carrier, either water, or an organic solvent (ethanol, NMP, or the like) or mixtures of surfactants and of solvents or of complexing agents and of solvents. The liquid forms will preferably be injectable and, as a result, will have a formulation that is acceptable for such a use. Acceptable routes of administration by injection include intravenous, intraperitoneal, intramuscular and subcutaneous routes, the intravenous route being preferred.

The administered dose of the compounds of the invention will be adjusted by the practitioner according to the route of administration to the patient and the condition of the latter.

Use of the Compounds of the Invention

According to a fourth aspect, the invention relates to the use of a compound according to the invention, for the production of a medicament for use in treating a pathological condition, preferably cancer, or a pathological condition chosen from psoriasis, glaucoma, leukemias and solid tumors, inflammation, and diseases associated with a disturbance of protein kinases. The present invention thus relates to the use of the pyrazolylbenzimidazolederivatives as anticancer agents. It also relates to the use of said derivatives for the preparation of a medicament for use in the treatment of humans.

The compounds according to the invention may therefore be of use in the prevention and treatment of leukemias, solid tumors which are both primary and metastatic, carcinomas and cancers, in particular: breast cancer; lung cancer; cancer of the small intestine, colorectal cancer, cancer of the respiratory tracts, of the oropharynx and of the hypopharynx; oesophageal cancer, liver cancer, stomach cancer, cancer of the bile ducts, cancer of the gall bladder, pancreatic cancer; cancers of the urinary tracts, including kidney, urothelium and bladder; cancers of the female genital tract, including cancer of the uterus, cervical cancer, ovarian cancer, choriocarcinoma and trophoblastoma; cancers of the male genital tract, including prostate cancer, cancer of the seminal vesicles, testicular cancer, germinal cell tumors; cancers of the endocrine glands, including thyroid cancer, pituitary cancer, cancer of the adrenal glands; skin cancers, including hemangiomas, melanomas, sarcomas, including Kaposi's sarcoma; brain tumors, nerve tumors, eye tumors, meningeal tumors, including astrocytomas, gliomas, glioblastomas, retinoblastomas, neurinomas, neuroblastomas, schwannomas, meningiomas; malignant hematopoietic tumors; leukemias (Acute Lymphocytic Leukemia (ALL), Acute Myeloid Leukemia (AML), Chronic Myeloid Leukemia (CML), Chronic Lymphocytic Leukemia (CLL)), chloromas, plasmocytomas, T or B cell leukemias, non-hodgkins or hodgkins lymphomas, myelomas, various malignant hemopathies.

The compounds of the present invention may be administered alone or as a mixture with other anticancer agents. Among the possible combinations, mention may be made of:

- alkylating agents, and in particular cyclophosphamide, melphalan, ifosfamide, chlorambucil, busulfan, thiotepa, prednimustine, carmustine, lomustine, semustine, streptozotocin, decarbazine, temozolomide, procarbazine and hexamethylmelamine;
- platinum derivatives, such as in particular cisplatin, carboplatin or oxaliplatin;
- antibiotics such as, in particular, bleomycin, mitomycin or dactinomycin;
- antimicrotubule agents such as, in particular, vinblastine, vincristine, vindesine, vinorelbine, taxoids (paclitaxel and docetaxel);
- anthracyclines such as, in particular, doxorubicin, daunorubicin, idarubicin, epirubicin, mitoxantrone, losoxantrone;
- topoisomerase group I and II inhibitors, such as etoposide, teniposide, amsacrine, irinotecan, topotecan and tomudex;
- fluoropyrimidines, such as 5-fluorouracil, UFT or floxuridine;
- cytidine analogs, such as 5-azacytidine, cytarabine, gemcitabine, 6-mercaptomurine or 6-thioguanine;
- adenosine analogs, such as pentostatin, cytarabine or fludarabine phosphate;
- methotrexate and folinic acid;
- various enzymes and compounds, such as L-asparaginase, hydroxyurea, trans-retinoic acid, suramine, dexrazoxane, amifostine, herceptin and also oestrogenic and androgenic hormones;
- antivascular agents, such as combretastatin derivatives or colchicine derivatives and prodrugs thereof.

It is also possible to combine, with the compounds of the present invention, a treatment by radiation. These treatments may be administered simultaneously, separately or sequentially. The treatment will be adjusted by the practitioner according to the patient to be treated.

The products according to the invention exhibit a strong cellular activity in a tumor cell (HeLa line) viability/proliferation inhibition test and a high selectivity with respect to quiescent peripheral blood lymphocytes (PBLs), used as a quiescent cell model.

Process for Obtaining the Compounds According to the Invention

A process for preparing the compounds of general formula (Ia) or (Ib) may be shown schematically in the following general way:

Scheme 1

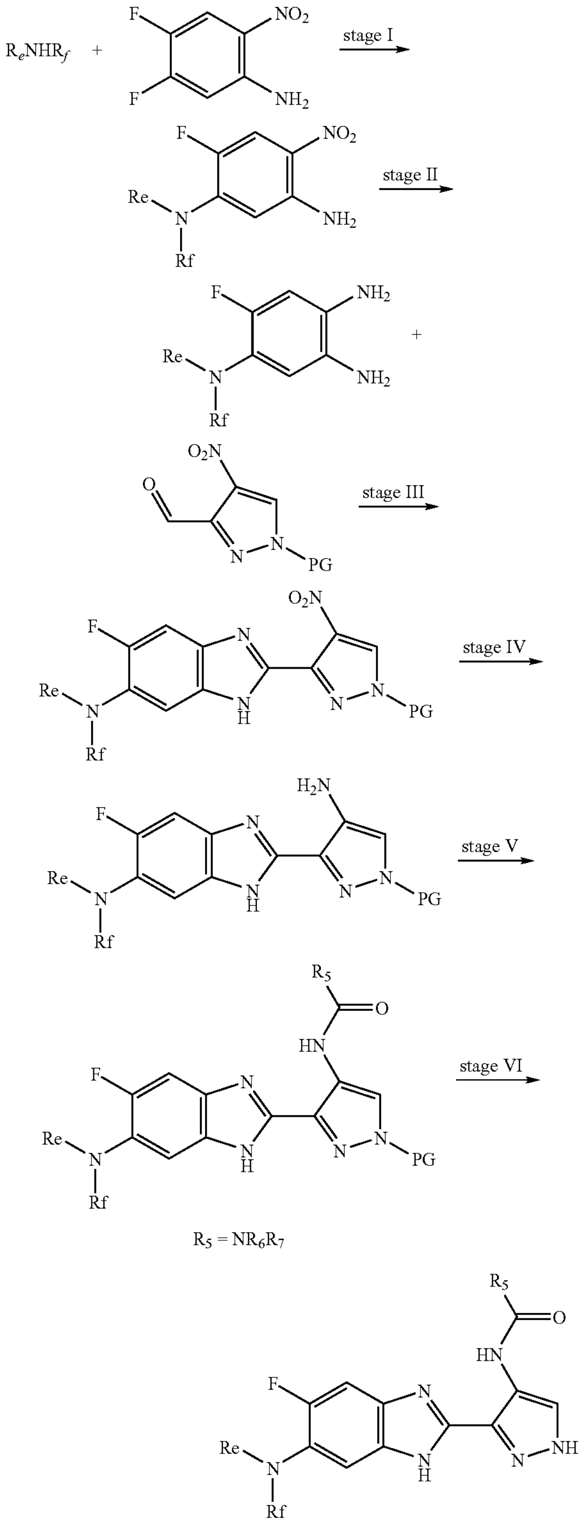

Stage I' as a replacement for stage I makes it possible to similarly prepare alkoxy derivatives by reaction of the fluoro derivative with an alkoxide $R_eO^-$. The latter may be prepared in situ by reaction with a base such as sodium hydride in a solvent such as DMF according to scheme 2:

Scheme 2

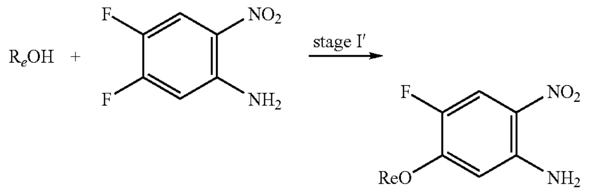

A subject of the invention is therefore also a process for preparing the compounds of formula (I) according to scheme 3 below:

optionally in the presence of a base (for example, N,N-diisopropylethylamine). Another pathway consists in forming a carbamate intermediate followed by displacement with an amine $R_6NHR_7$. Stage VI corresponds to a deprotection stage, the conditions of which depend on the nature of the protective group. In the presence of a tetrahydropyran, this stage may be carried out in a concentrated acidic medium.

A subject of the invention is therefore a preparation process in which the compound of formula (II) is subjected to a reduction reaction in order to obtain an aminated derivative of formula (III). This derivative is then acylated in the presence of carbamoyl chloride and, optionally, of a base (such as N,N-diisopropyl-ethylamine), or else by formation of a carbamate intermediate followed by displacement with an amine Scheme 3

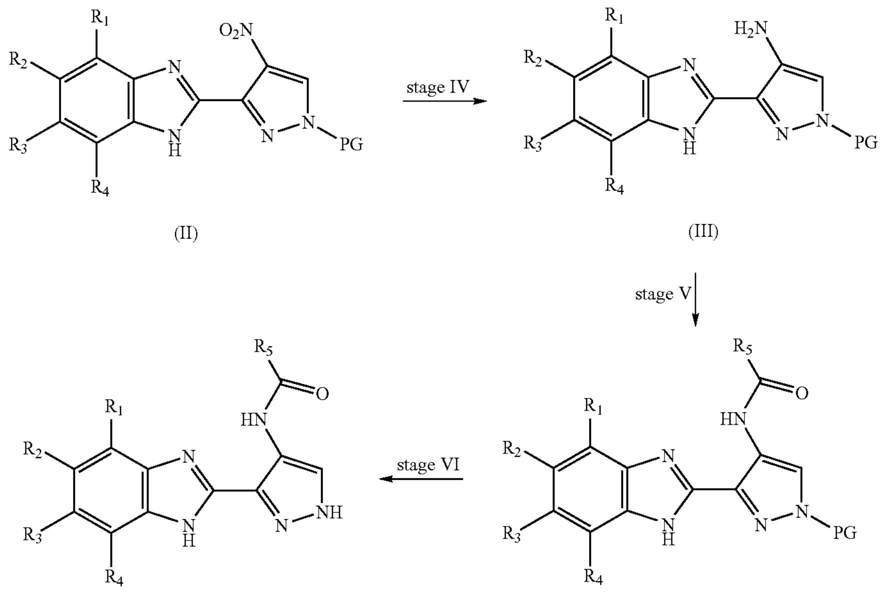

(II) (III) (I) (IV)

In schemes 1 and 3, PG denotes a protective group, the function of which is to prevent undesired reactions on the pyrazole ring during one or more of the reaction stage (s). Examples of protective groups will be found in T. W. Greene et al., in "Protective Groups in Organic Synthesis", third edition, 1999, Wiley-Interscience, or else in J. F. W. McOmie in "Protective Groups in Organic Chemistry", Plenum Press, 1973. Preferably, the protective group is the following:

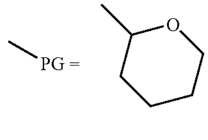

(tetrahydropyran).

In general, stage IV corresponds to the reduction of the nitro group carried by the pyrazole ring. It may be carried out by catalytic hydrogenation in a solvent such as, for example, ethyl acetate in the presence of a catalyst (for example, a palladium catalyst). The functionalization of this amine during stage V may be carried out in a solvent (such as THF), in the presence of an acylating agent for introducing the unit $R_5CO$—, for example a carbamoyl chloride $R_5COCl$, and in order to obtain the pyrazole of formula (IV). The subsequent deprotection stage makes it possible to recover the compound of formula (I), and is known to those skilled in the art. Thus, the deprotection may be carried out in a concentrated acidic medium in the case of a tetrahydropyran. The compound of formula (I) is then, where appropriate, salified.

The compound of formula (II) is obtained according to the following method. In general, in stage I, the precursor of the aromatic diamine required for the formation of the benzimidazolering is formed by selective nucleophilic substitution of a fluorine atom of 4,5-difluoro-2-nitroaniline with an amine $R_eNHR_f$ in a solvent such as DMF in the presence of a base such as sodium bicarbonate. In stage II, the aromatic nitro group is reduced. This reaction may be carried out in the presence of hydrogen and of a palladium catalyst. Stage III for formation of the benzimidazolering is carried out by condensation of the diamine obtained with a suitably functionalized aldehyde in a solvent such as DMF or methanol, optionally in the presence of a catalyst, such as, for example, iron trichloride.

The subject of the invention is also the intermediate compounds of formulae (II), (III) and (IV) as defined above, preferably with the tetrahydropyran protective group defined above and according to all the limitations described for $R_1$ to $R_5$ for the compounds of formula (I).

EXAMPLES

A subject of the invention is also the compounds as prepared in the examples below.

LC/MS Analyses

The LC/MS analyses are carried out on a Micromass model LCT machine connected to an HP 1100 machine. The abundance of the products was measured using an HP G1315A diode array detector over a wavelength range of 200-600 nm and a Sedex 65 light scattering detector. The mass spectra were acquired over a range from 180 to 800 nm. The data were analyzed using the Micromass MassLynx software. The separation was performed on a Hypersil BDS C18, 3 μm (50×4.6 mm) column, elution being carried out with a linear gradient of 5% to 90% of acetonitrile containing 0.05% (v/v) of formic acid in water containing 0.05% (v/v) of formic acid, over 3.5 min at a flow rate of 1 mL/min. The total analysis time, including the column reequilibration period, is 7 minutes.

Purification by flash chromatography: the crude products are purified by flash chromatography on cartridges of silica with a particle size of 50 μm. The fractions corresponding to the expected product are combined and concentrated under reduced pressure in a rotary evaporator.

$^1H$ NMR Analyses $^1H$ NMR spectrum at 400 MHz on a Bruker Avance DRx-400 spectrometer with chemical shifts (δ in ppm)—in DMSO-d6 referenced at 2.50 ppm at a temperature of 303K, where appropriate after addition of a drop of TFA-d1 ($CF_3COOD$-d1) and of a drop of acetic acid-d4-($CD_3OD$-d4).

$1^H$ NMR spectrum at 300 MHz on a Bruker Avance DRX-300 spectrometer with chemical shifts (δ in ppm)—in DMSO-d6 referenced at 2.50 ppm at a temperature of 303K, where appropriate after addition of a drop of TFA-d1 (trifluoroacetic acid $CF_3COOD$-d1) and of a drop of acetic acid-d4-($CD_3OD$-d4).

The mass spectra were realized by electron impact on a Finnigan SSQ 7000 spectrometer and by electrospray on a Micromass Platform II (best results obtained in positive or negative ionization mode according to the structures).

The compounds of the examples below are prepared according to scheme 1.

Example 1

N-[3-(5-fluoro-6-morpholin-4-yl-1H-benzimidazol-2-yl)-1H-pyrazol-4-yl]piperidine-1-carboxamide Hydrochloride

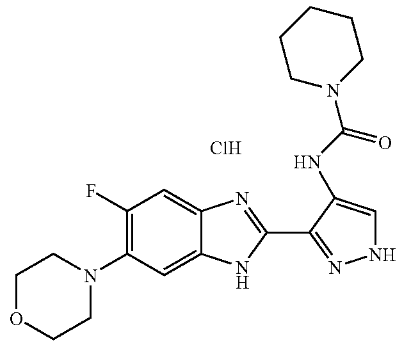 [SMILES: O=C(Nc1c[nH]nc1-c1nc2cc(F)c(N3CCOCC3)cc2[nH]1)N1CCCCC1 ; Cl]

Stage I

4-fluoro-5-morpholin-4-yl-2-nitrophenylamine

A solution of 26 g of 4,5-difluoroaniline in 500 mL of DMF is stirred at 22° C. 39 mL of morpholine and 61.3 g of sodium bicarbonate are added. The reaction medium is heated at 80° C. using an oil bath for one hour. A yellow solid precipitates. The medium is cooled to ambient temperature and then 800 mL of distilled water are added. The medium is cooled using an ice bath. The solid is filtered off, washed with water and then dried under vacuum in the presence of potassium hydroxide until the weight is constant. 35.1 g of 4-fluoro-5-morpholin-4-yl-2-nitrophenylamine are obtained in the form of a yellow solid. Melting point: 190-192° C. (Kofler bench). $^1H$ NMR (400 MHz, $(CD_3)_2SO$, δ in ppm): 3.15 (m: 4H); 3.73 (m:4H); 6.43 (d, J=8 Hz:1H), 7.37 (broad s: 2H); 7.66 (d, J=15 Hz: 1H).

Stage II

4-fluoro-5-morpholin-4ylbenzene-1,2-diamine 35 g of 4-fluoro-5-morpholin-4-yl-2-nitrophenylamine in solution in 618 mL of methanol are hydrogenated under 1 bar of hydrogen pressure in the presence of 3.4 g of palladium-on-charcoal at 22° C. for 16 hours. The reaction crude is filtered through celite and the filtrate is concentrated under vacuum in a rotary evaporator. 30 g of 4-fluoro-5-morpholin-4-ylbenzene-1,2-diamine in the form of a brown solid are isolated. $^1H$ NMR (400 MHz, $(CD_3)_2SO$, δ in ppm): 2.78 (m: 4H); 3.68 (m: 4H); 4.25 (broad s: 2H); 4.35 (broad s: 2H); 6.27 (d, J=8 Hz: 1H); 6.31 (d, J=14 Hz: 2H).

Stage III

6-fluoro-5-morpholin-4-yl-2-(4-nitro-1H-pyrazol-3-yl)-1H-benzimidazol 530 mg of 4-nitro-1-(tetrahydropyran-2-yl)-1H-pyrazole-3-carbaldehyde (the preparation of which is described in WO 03/035065, reference example 6m page 479) are added slowly to a solution of 500 mg of 4-fluoro-5-morpholin-4-ylbenzene-1,2-diamine in 50 mL of methanol, and then 19.5 mg of ferric chloride are added. The reaction medium is stirred at 22° C. for 18 hours. After evaporation, the reaction crude is purified by flash chromatography on an Intelliflash apparatus on an Analogix RS-90 cartridge. The elution is carried out as follows: 100% cyclohexane for 20 minutes, then 20 minutes with an 80:20 cyclohexane/ethyl acetate mixture and 120 minutes with a 20:80 cyclohexane/ethyl acetate mixture. 457 mg of 6-fluoro-5-morpholin-4-yl-2-(4-nitro-1H-pyrazol-3-yl)-1H-benzimidazoleare isolated. $^1H$ NMR (400 MHz, $(CD_3)_2SO$, δ in ppm): 1.42-1.80 (m: 3H); 1.91-2.06 (m: 2H); 2.18 (m: 1H); 3.02 (m: 4H); 3.70 (m: 1H); 3.78 (m: 4H); 4.00 (broad d J=10 Hz: 1H); 5.60 (dd, J=10 and 2 Hz: 1H); 7.18 (very broad s: 1H); 7.45 (very broad s: 1H); 9.18 (s: 1H); 12.85 (very broad s: 1H).

Stage IV

3-(5-fluoro-6-morpholin-4-yl-1H-benzimidazol-2-yl)-1-(tetrahydropyran-2-yl)-1H-pyrazol-4-ylamine (Gamma Intermediate)

A suspension of 12 g of 6-fluoro-5-morpholin-4-yl-2-(4-nitro-1H-pyrazol-3-yl)-1H-benzimidazolein 200 mL of methanol and 1 g of palladium-on-charcoal is hydrogenated under 1 bar of hydrogen pressure at ambient temperature for 18 hours. The reaction medium is filtered through celite and the filtrate is concentrated under reduced pressure in a rotary evaporator. 10.6 g of 3-(5-fluoro-6-morpholin-4-yl-1H-benzimidazol-2-yl)-1-(tetrahydro-pyran-2-yl)-1H-pyrazol-4-ylamine are obtained in the form of a black solid. Analytical LC/MS: Tr=4.79 min, $[M+H]^+$=387.12 DAD=38%.

Stage V

Piperidine-1-carboxylic acid [3-(5-fluoro-6-morpholin-4-yl-1H-benzimidazol-2-yl)-1-(tetrahydro-pyran-2-yl)-1H-pyrazol-4-yl]amide 10 mL of piperidinecarbonyl chloride and 13.55 mL of N,N-diisopropylethylamine are added to a solution of 10 g of 3-(5-fluoro-6-morpholin-4-yl-1H-benzimidazol-2-yl)-1-(tetrahydropyran-2-yl)-1H-pyrazol-4-ylamine in 200 mL of THF. The reaction mixture is refluxed for 3 hours and then left stirring at ambient temperature for 48 hours. After concentration of the medium vacuum in a rotary evaporator, the reaction crude is purified by flash chromatography on 1200 g of 40-63 μM silica, elution being carried out with a 90:10 mixture of dichloromethane/acetone. 10.4 g of piperidine-1-carboxylic acid [3-(5-fluoro-6-morpholin-4-yl-1H-benzimidazol-2-yl)-1-(tetrahydropyran-2-yl)-1H-pyrazol-4-yl]amide are isolated. $^1H$ NMR (300 MHz, $(CD_3)_2S$, δ in ppm): 1.50-1.79 (m: 10H); 1.91-2.04 (m: 2H); 3.00 (m: 4H); 3.50 (m: 4H); 3.66 (m: 1H); 3.77 (m: 4H); 3.96 (broad d J=11 Hz: 1H); 5.46 (dd, J=10 and 2 Hz: 1H); 7.10 (very broad s: 1H); 7.40 (very broad s: 1H); 8.13 (s: 1H); 9.96 (broad s: 1H); 13.00 (very broad s: 1H).

Stage VI

Piperidine-1-carboxylic acid [3-(5-fluoro-6-morpholin-4-yl-1H-benzimidazol-2-yl)-1H-pyrazol-4-yl] amide, in Hydrochloride Form A solution of 4 g of piperidine-1-carboxylic acid [3-(5-fluoro-6-morpholin-4-yl-1H-benzimidazol-2-yl)-1-(tetrahydropyran-2-yl)-1H-pyrazol-4-yl]amide in solution in 50 mL of a 4N solution of hydrochloric acid in dioxane is stirred at 22° C. for 4 hours. In order for the reaction to be complete, the reaction medium is concentrated and again dissolved in 50 mL of a 4N solution of hydrochloric acid in dioxane and left stirring at ambient temperature for 18 hours. The suspension is filtered over sintered glass and the solid is washed with dioxane. After spin-filter-drying, the solid is triturated in isopropyl ether. Since the solid obtained is hygroscopic, it is taken up in methanol and the solution is concentrated under vacuum. The oil obtained is purified by flash chromatography on an Intelliflash apparatus on an analogix RS-120 cartridge. The elution is carried out with dichloromethane then ethyl acetate at 100%, and then with a 95/5 mixture of dichloromethane/methanol. After concentration of the fractions containing the product, the latter is triturated in isopropyl ether and the solid obtained is filtered and dried under vacuum until the weight is constant. 3.2 g of piperidine-1-carboxylic acid [3-(5-fluoro-6-morpholin-4-yl-1H-benzimidazol-2-yl)-1H-pyrazol-4-yl]amide are obtained in hydrochloride form. $^1H$ NMR (300 MHz, $(CD_3)_2SO$, δ in ppm): 1.48-1.67 (m: 6H); 3.03 (m: 4H); 3.48 (m: 4H); 3.78 (m: 4H); 7.18 (d, J=8 Hz: 1H); 7.46 (d, J=12 Hz: 1H); 8.01 (s: 1H); 9.53 (broad s: 1H); 12.50 (very broad s: 1H).

Example 2

1,1-diethyl-3-[3-(5-fluoro-6-morpholin-4-yl-1H-benzimidazol-2-yl)-1H-pyrazol-4-yl]urea Trifluoroacetate

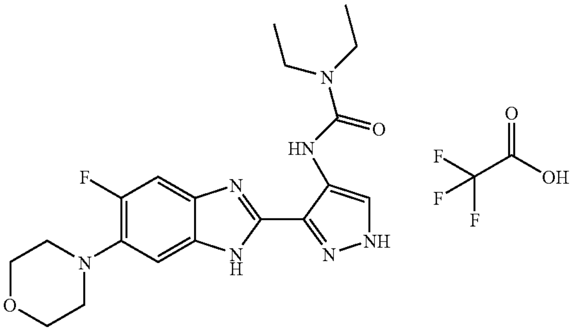 [SMILES: CCN(CC)C(=O)Nc1c[nH]nc1-c1nc2cc(F)c(N3CCOCC3)cc2[nH]1 ; O=C(O)C(F)(F)F]

Stage V 1,1-diethyl-3-[3-(5-fluoro-6-morpholin-4-yl-1H-benzimidazol-2-yl)-1-(tetrahydropyran-2-yl)-1H-pyrazol-4-yl]urea 100 mg of gamma intermediate are solubilized in 10 mL of tetrahydrofuran and then 214 μL of N,N-diisopropylethylamine and 1.2 mL of diethylcarbamoyl chloride are added. The reaction medium is stirred at 50° C. overnight. The organic phase is washed with 2×10 mL of a saturated solution of sodium bicarbonate. The aqueous phases are extracted with 3×15 mL of ethyl acetate. The combined organic phases are dried over magnesium sulfate, filtered and concentrated under vacuum in a rotary evaporator. The reaction crude is purified on a 10 g silica cartridge, eluent: 1/1 AcOEt/cyclohexane. 95 mg of 1,1-diethyl-3-[3-(5-fluoro-6-morpholin-4-yl-1H-benzimidazol-2-yl)-1-(tetrahydropyran-2-yl)-1H-pyrazol-4-yl]urea are isolated in the form of a yellow foam. $^1H$ NMR (400 MHz, DMSO-d6, δ in ppm): 1.23 (t, J=7.0 Hz, 6H); from 1.51 to 1.81 (m, 3H); 1.98 (m, 2H); 2.13 (m, 1H); 3.00 (m, 4H); 3.41 (q, J=7.0 Hz, 4H); 3.66 (m, 1H); 3.77 (m, 4H); 3.96 (m, 1H); 5.46 (dd, J=2.0 and 10.0 Hz, 1H); from 6.96 to 7.47 (broad m, 2H); 8.12 (s, 1H); 9.88 (broad m, 1H); 13.0 (broad m, 1H).

Stage VI 1,1-diethyl-3-[3-(5-fluoro-6-morpholin-4-yl-1H-benzimidazol-2-yl)-1H-pyrazol-4-yl]urea

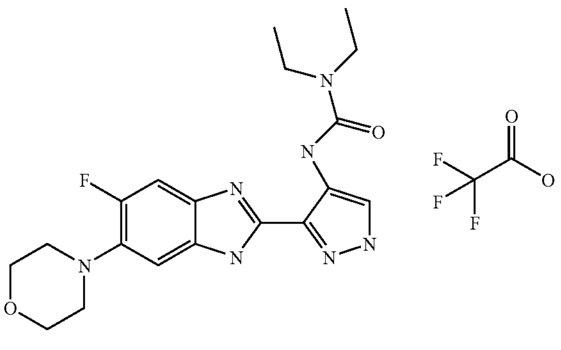 [SMILES: CCN(CC)C(=O)Nc1c[nH]nc1-c1nc2cc(F)c(N3CCOCC3)cc2[nH]1 ; O=C(O)C(F)(F)F]

A solution of 95 mg of 1,1-diethyl-3-[3-(5-fluoro-6-morpholin-4-yl-1H-benzimidazol-2-yl)-1-(tetrahydropyran-2-yl)-1H-pyrazol-4-yl]urea in 3 mL of dichloromethane, to which 750 μL of trifluoroacetic acid are added, is stirred at ambient temperature for 48 hours. The reaction medium is concentrated to dryness and then purified by preparative LC/MS: injection of the product in 2.5 mL of DMSO, elution with a gradient of 5% to 95% of acetonitrile in water, containing respectively 0.07% of TFA, in 12 minutes. 49 mg of 1,1-diethyl-3-[3-(5-fluoro-6-morpholin-4-yl-1H-benzimidazol-2-yl)-1H-pyrazol-4-yl]urea are isolated in the form of a trifluoroacetate salt. $^1$H NMR (300 MHz, DMSO-d6, δ in ppm): 1.23 (t, J=7.0 Hz, 6H); 3.00 (m, 4H); 3.41 (m partially masked, 4H); 3.78 (m, 4H); 7.11 (broad d, J=8.0 Hz, 1H); 7.33 (broad d, J=12.0 Hz, 1H); 7.99 (s, 1H); 9.78 (s, 1H); 13.0 (broad m, 2H).

Example 3

N-{3-[5-fluoro-6-(2-piperidin-1-ylethoxy)-1H-benzimidazol-2-yl]-1H-pyrazol-4-yl}piperidine-1-carboxamide Hydrochloride

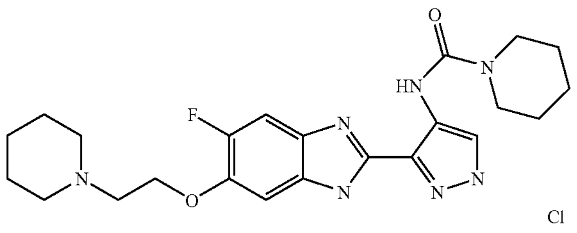 [SMILES: O=C(Nc1c[nH]nc1-c1nc2cc(F)c(OCCN3CCCCC3)cc2[nH]1)N1CCCCC1 ; Cl]

Stage I 4-fluoro-2-nitro-5-(2-piperidin-1-ylethoxy)-phenylamine

A solution of 1.11 g of 2-piperidin-1-ylethanol in 20 mL of N,N-dimethylformamide (DMF) is cooled to 0° C. with an ice bath. 689 mg of sodium hydride (60% in suspension in oil) are added in small portions. The suspension obtained is added dropwise to a suspension containing 500 mg of 4,5-difluoro-2-nitrophenylamine and 724 mg of sodium bicarbonate in 15 mL of DMF. The reaction medium is stirred at ambient temperature (22° C.) for 2 hours and then heated at 90° C. for 1 hour. The solvent is concentrated to dryness, then the reaction crude is taken up in 30 mL of ethyl acetate and the organic phase is washed with 2×30 mL of distilled water and 1×30 mL of a saturated aqueous solution of sodium chloride. The organic phase is dried over magnesium sulfate and the solvent is evaporated off under vacuum in a rotary evaporator. The crude is triturated in ethyl ether and the solid is filtered through sintered glass and rinsed with ethyl ether. 443 mg of 4-fluoro-2-nitro-5-(2-piperidin-1-ylethoxy)-phenylamine in the form of a red solid are isolated. $^1$H NMR (300 MHz, DMSO-d6, δ in ppm): 1.37 (m, 2H); 1.48 (m, 4H); 2.43 (m, 4H); 2.69 (t, J=6.5 Hz, 2H); 4.13 (t, J=6.5 Hz, 2H); 6.65 (d, J=8.0 Hz, 1H); 7.48 (broad s, 2H); 7.75 (d, J=12.0 Hz, 1H).

Stage II 4-fluoro-5-(2-piperidin-1-ylethoxy)benzene-1,2-diamine 443 mg of 4-fluoro-2-nitro-5-(2-piperidin-1-ylethoxy)-phenylamine in solution in 20 mL of methanol are hydrogenated under 1 bar of hydrogen pressure in the presence of 44 mg of palladium-on-charcoal at 25° C. for 10 hours. The reaction crude is filtered through celite and the filtrate is concentrated under vacuum in a rotary evaporator. 380 mg of 4-fluoro-5-(2-piperidin-1-ylethoxy)benzene-1,2-diamine are obtained in the form of a black lake. The compound is used without any other purification.

Stage III 5-fluoro-2-[4-nitro-1-(tetrahydropyran-2-yl)-1H-pyrazol-3-yl]-6-(2-piperidin-1-ylethoxy)-1H-benzimidazol A solution of 248 mg of 4-nitro-1-(tetrahydropyran-2-yl)-1H-pyrazole-3-carbaldehyde and 278.9 mg of 4-fluoro-5-(2-piperidin-1-ylethoxy)benzene-1,2-diamine in 12 mL of methanol is stirred at ambient temperature overnight. In order for the reaction to be complete, heating is carried out for a further half an hour at reflux and then overnight at ambient temperature. After concentration under vacuum in a rotary evaporator, 515 mg of 5-fluoro-2-[4-nitro-1-(tetrahydropyran-2-yl)-1H-pyrazol-3-yl]-6-(2-piperidin-1-ylethoxy)-1H-benzimidazoleare isolated in the form of a dark solid. $^1$H NMR (300 MHz, DMSO-d6, δ in ppm): for this batch, we observe a 60%-40% resolution of tautomers with: from 1.31 to 1.78 (m, 9H); from 1.87 to 2.30 (m, 3H); 2.46 (m partially masked, 4H); 2.72 (t, J=6.0 Hz, 2H); 3.69 (m, 1H); 4.00 (m, 1H); 4.19 (t, J=6.0 Hz, 2H); 5.60 (dd, J=2.0 and 9.0 Hz, 1H); 7.26 (d, J=7.5 Hz, 0.6H); 7.41 (d, J=11.5 Hz, 0.4H); 7.45 (d, J=7.5 Hz, 0.4H); 7.53 (d, J=11.5 Hz, 0.6H); 9.18 (s, 1H); 12.85 (broad m, 1H).

Stage IV

3-[5-fluoro-6-(2-piperidin-1-ylethoxy)-1H-benzimidazol-2-yl]-1-(tetrahydropyran-2-yl)-1H-pyrazol-4-ylamine (Alpha Intermediate)

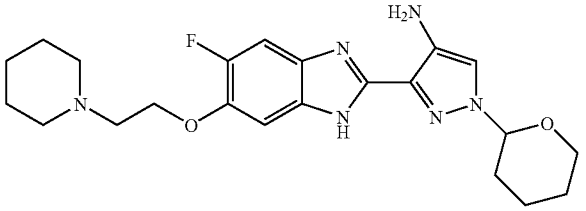 [SMILES: Nc1cn(C2CCCCO2)nc1-c1nc2cc(F)c(OCCN3CCCCC3)cc2[nH]1]

A suspension of 160 mg of 5-fluoro-2-[4-nitro-1-(tetrahydropyran-2-yl)-1H-pyrazol-3-yl]-6-(2-piperidin-1-ylethoxy)-1H-benzimidazolein 10 mL of ethyl acetate and 16 mg of palladium-on-charcoal is hydrogenated under 1 bar of hydrogen pressure at ambient temperature for 16 hours. The reaction medium is filtered through celite and the filtrate is concentrated under reduced pressure in a rotary evaporator. 150 mg of 3-[5-fluoro-6-(2-piperidin-1-ylethoxy)-1H-benzimidazol-2-yl]-1-(tetrahydropyran-2-yl)-1H-pyrazol-4-ylamine are isolated in the form of a red oil. Analytical LC/MS: Tr=2.04 min, $[M+H]^+$=429.05 DAD=70%.

Stage V

Piperidine-1-carboxylic acid [3-[5-fluoro-6-(2-piperidin-1-ylethoxy)-1H-benzimidazol-2-yl]-1-(tetrahydropyran-2-yl)-1H-pyrazol-4-yl]amide A solution of 155 μl of piperidine-1-carbonyl chloride, 60 mg of alpha intermediate and 200 μl of N,N-diisopropylamine in 6 mL of tetrahydrofuran is heated at 50° C. for 18 hours. The reaction medium is concentrated to dryness and the crude is purified by flash chromatography on a silica cartridge, eluent: 100/0 to 90/10 dichloromethane/methanol. 30 mg of piperidine-1-carboxylic acid [3-[5-fluoro-6-(2-piperidin-1-ylethoxy)-1H-benzimidazol-2-yl]-1-(tetrahydropyran-2-yl)-1H-pyrazol-4-yl]amide are obtained in the form of a yellowish oil. Analytical LC/MS: Tr=2.94 min, $[M+H]^+$=540.38 DAD=95%.

Stage VI

N-{3-[5-fluoro-6-(2-piperidin-1-ylethoxy)-1H-benzimidazol-2-yl]-1H-pyrazol-4-yl}piperidine-1-carboxamide Hydrochloride A solution of 30 mg of piperidine-1-carboxylic acid [3-[5-fluoro-6-(2-piperidin-1-ylethoxy)-1H-benzimidazol-2-yl]-1-(tetrahydropyran-2-yl)-1H-pyrazol-4-yl]amide in 3 mL of a 3N solution of hydrochloric acid in dioxane is stirred at 22° C. for 18 hours. The reaction medium is concentrated to dryness and the crude is purified by flash chromatography on a 2 g silica cartridge, eluent: 90/10 to 70/30 dichloromethane/methanol. 20 mg of N-{3-[5-fluoro-6-(2-piperidin-1-ylethoxy)-1H-benzimidazol-2-yl]-1H-pyrazol-2-yl}piperidine-1-carboxamide hydrochloride are obtained in the form of an ochre solid. $^1$H NMR (400 MHz, DMSO-d6, δ in ppm) after addition of a drop of acetic acid-d4-($CD_3OD$-d4) and of a drop of TFA-d1 (trifluoroacetic acid $CF_3COOD$-d1): from 1.32 to 1.88 (m, 12H); 3.05 (m, 2H); 3.43 (m, 4H); 3.57 (m, 4H); 4.50 (m, 2H); 7.44 (d, J=8.0 Hz, 1H); 7.61 (d, J=11.0 Hz, 1H); 8.00 (s, 1H). Analytical LC/MS: Tr=2.66 min, $[M+H]^+$=456.32 DAD=100%.

Example 4

1,1-diethyl-3-{3-[5-fluoro-6-(2-piperidin-1-ylethoxy)-1H-benzimidazol-2-yl]-1H-pyrazol-4-yl}urea Trifluoroacetate

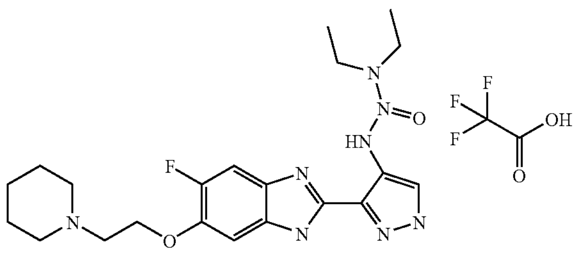

Stage V 1,1-diethyl-3-[3-[5-fluoro-6-(2-piperidin-1-ylethoxy)-1H-benzimidazol-2-yl]-1-(tetrahydropyran-2-yl)-1H-pyrazol-4-yl]urea 140 mg of alpha intermediate are solubilized in 10 mL of tetrahydrofuran and then 414 μL of diethylcarbamoyl chloride and 542 μL of N,N-diisopropylethylamine are added. The reaction medium is stirred for 48 hours at 56° C. The organic phase is washed with 2×15 mL of a saturated aqueous solution of sodium bicarbonate. The aqueous phase is extracted with 3×15 mL of ethyl acetate. The combined organic phases are dried over magnesium sulfate and filtered, and the solvent is evaporated off under vacuum in a rotary evaporator. The reaction crude is purified by flash chromatography on a 40 g silica cartridge, eluent: 100/0 to 85/15 dichloromethane/methanol. The fractions containing the products are combined and concentrated under vacuum in a rotary evaporator. 38 mg of 1,1-diethyl-3-[3-[5-fluoro-6-(2-piperidin-1-ylethoxy)-1H-benzimidazol-2-yl]-1-(tetrahydropyran-2-yl)-1H-pyrazol-4-yl]urea are isolated. $^1$H NMR (400 MHz, DMSO-d6, δ in ppm), for this batch, we observe the expected structure of the salt with a 60%-40% resolution of tautomers: 1.23 (m, 6H); from 1.31 to 2.18 (m, 12H); from 2.99 to 3.75 (broad m, 6H); 3.42 (m, 4H); 3.66 (m, 1H); 3.96 (m, 1H); from 4.12 to 4.58 (broad m, 2H); 5.46 (broad d, J=10.0 Hz, 1H); from 7.10 to 7.55 (m, 2H); 8.14 (s, 1H); 9.69 (broad m, 1H); 9.79 (s, 0.4H); 9.82 (s, 0.6H); 13.1 (broad m, 1H).

Stage VI 1,1-diethyl-3-{3-[5-fluoro-6-(2-piperidin-1-ylethoxy)-1H-benzimidazol-2-yl]-1H-pyrazol-4-yl}urea Trifluoroacetate A solution of 38 mg of 1,1-diethyl-3-{3-[5-fluoro-6-(2-piperidin-1-ylethoxy)-1H-benzimidazol-2-yl]-1-(tetrahydropyran-2-yl)-1H-pyrazol-4-yl}urea is solubilized in 2 mL of dichloromethane and then 500 μl of trifluoroacetic acid are added. The reaction medium is stirred at ambient temperature overnight. The solvent is evaporated off under vacuum in a rotary evaporator and the crude is reacted again in 500 μL of dichloromethane and 500 μL of trifluoroacetic acid at ambient temperature for one hour. After concentration of the solvent in a rotary evaporator, the reaction crude is purified by flash chromatography on a 4 g silica cartridge, eluent: 100/0 to 90/10 dichloromethane/-methanol. 20 mg of 1,1-diethyl-3-{3-[5-fluoro-6-(2-piperidin-1-ylethoxy)-1H-benzimidazol-2-yl]-1H-pyrazol-4-yl}urea trifluoroacetate are isolated in the form of a yellow solid. $^1$H NMR (400 MHz, DMSO-d6, δ in ppm), for this batch, we observe a 60%-40% resolution of tautomers with: 1.24 (m, 6H); from 1.32 to 1.93 (m, 6H); 3.06 (broad m, 2H); from 3.23 to 3.68 (broad m, 4H); 3.41 (m, 4H); 4.44 (broad m, 2H); 7.21 (d, J=8.0 Hz, 0.6H); 7.32 (d, J=11.0 Hz, 0.4H); 7.38 (d, J=8.0 Hz, 0.4H); 7.49 (d, J=11.0 Hz, 0.6H); 8.01 (s, 1H); 9.32 (broad m, 1H); 9.74 (s, 0.4H); 9.77 (s, 0.6H); 13.0 (s, 1.6H); 13.05 (s, 0.4H).

Example 5

3-{3-[6-(3-dimethylaminopropoxy)-5-fluoro-1H-benzimidazol-2-yl]-1H-pyrazol-4-yl}-1,1-diethylurea Trifluoroacetate

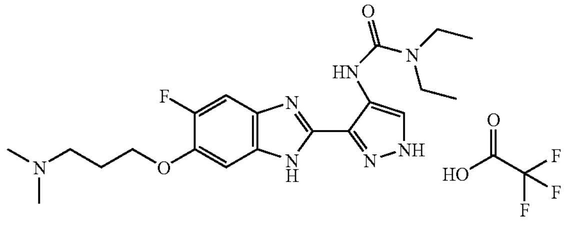

Stage I

Preparation of 5-(3-dimethylaminopropoxy)-4-fluoro-2-nitrophenylamine

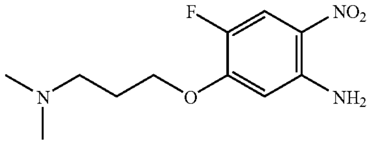 [SMILES: CN(C)CCCOc1cc(N)c([N+](=O)[O-])cc1F]

A solution of 6.1 mL of 3-dimethylamino-1-propanol in 100 mL of anhydrous THF is cooled using an ice bath. Under argon, 1.1 g of NaH are added in small portions (solution A). The reaction medium is left stirring for 1 hour at 0° C. A solution of 3 g of 4,5-difluoroaniline in 100 mL of anhydrous THF is stirred at 22° C. 4.3 g of sodium bicarbonate are added. The solution containing the alkoxide (solution A) is added dropwise. The reaction medium is heated at 80° C. using an oil bath for 30 minutes. The reaction medium is cooled to ambient temperature and 100 mL of water are added. The aqueous phase is extracted with three times 100 mL of EtOAc. The organic phases are dried over $MgSO_4$, filtered and concentrated under vacuum in a rotary evaporator. The orangey-yellow solid is taken up in pentane, triturated, filtered, rinsed with pentane and dried. 3.5 g of 5-(3-dimethylaminopropoxy)-4-fluoro-2-nitrophenylamine are obtained in the form of a brown solid. Analytical LC/MS: $t_r$=2.16 min; $[M+H]^+$=258.27; ELSD=100%. $^1H$ NMR (400 MHz, DMSO-d6, δ in ppm): 1.9 (m, J=6.0 Hz, 2H); 2.13 (s, 6H); 2.35 (t, J=6.0 Hz, 2H); 4.08 (t, J=6.0 Hz, 2H); 6.64 (d, J=8.0 Hz, 1H); 7.47 (s, 2H); 7.73 (d, J=11.0 Hz, 1H).

Stage II 4-(3-dimethylaminopropoxy)-5-fluorobenzene-1,2,-diamine

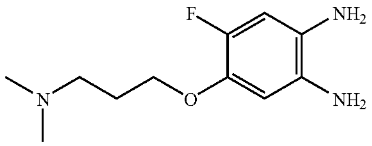

3.8 g of 5-(3-dimethylaminopropoxy)-4-fluoro-2-nitrophenylamine in solution in 100 mL of methanol are hydrogenated under 1 bar of hydrogen pressure in the presence of 400 mg of palladium-on-charcoal at 25° C. for 16 hours. The reaction crude is filtered through celite and the filtrate is concentrated under vacuum in a rotary evaporator. 3.5 g of 4-(3-dimethylaminopropoxy)-5-fluorobenzene-1,2-diamine are isolated in the form of a black oil. $^1H$ NMR (400 MHz, DMSO-d6, δ in ppm): 1.75 (m, 2H); 2.13 (m, 6H); 2.32 (m, 2H); 3.84 (m, 2H); 4.3 (m, 4H); 6.32 (m, 2H).

Stage III

Preparation of (3-{6-fluoro-2-[4-nitro-1-(tetrahydro-pyran-2-yl)-1H-pyrazol-3-yl]-3H-benzimidazol-5-yloxy}propyl)dimethylamine

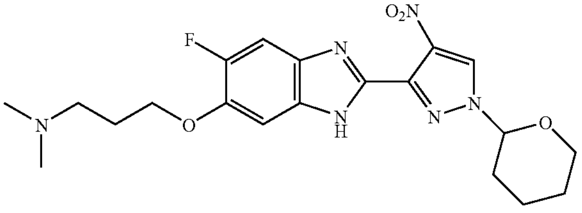 [SMILES: CN(C)CCCOc1cc2[nH]c(-c3nn(C4CCCCO4)cc3[N+](=O)[O-])nc2cc1F]

3.4 g of 4-nitro-1-(tetrahydropyran-2-yl)-1H-pyrazole-3-carbaldehyde are added to a solution of 3.5 g of 4-(3-dimethylaminopropoxy)-5-fluorobenzene-1,2-diamine in 150 mL of methanol. The reaction medium is stirred at 22° C. for 18 hours. After evaporation, the reaction crude is purified by flash chromatography on an Intelliflash apparatus on an Analogix RS-330 cartridge. The elution is carried out in dichloromethane with 10% of methanol. 2.3 g of (3-{6-fluoro-2-[4-nitro-1-(tetrahydropyran-2-yl)-1H-pyrazol-3-yl]-3H-benzimidazol-5-yloxy}-propyl)dimethylamine are isolated. $^1H$ NMR (300 MHz, DMSO-d6, δ in ppm): 1.50 to 2.23 (m, 8H); 2.80 (s, 6H); 3.23 (m, 2H); 3.68 (m, 1H); 3.98 (m, 1H); 4.17 (t, J=6.0 Hz, 2H); 5.58 (dd, J=2.5 and 9.5 Hz, 1H); 7.34 (d, J=8.0 Hz, 1H); 7.49 (d, J=11.0 Hz, 1H) 9.11 (s, 1H).

Stage IV

3-[6-(3-dimethylaminopropoxy)-5-fluoro-1H-benzimidazol-2-yl]-1-(tetrahydropyran-2-yl)-1H-pyrazol-4-ylamine (Intermediate 1)

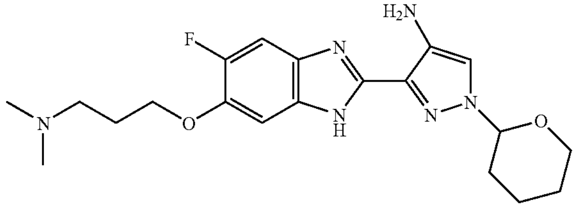 [SMILES: CN(C)CCCOc1cc2[nH]c(-c3nn(C4CCCCO4)cc3N)nc2cc1F]

A suspension of 2.3 g of (3-{6-fluoro-2-[4-nitro-1-(tetrahydropyran-2-yl)-1H-pyrazol-3-yl]-3H-benzimidazol-5-yloxy}propyl)dimethylamine in 40 mL of methanol and 0.2 g of palladium-on-charcoal is hydrogenated under 1 bar of hydrogen pressure at ambient temperature for 18 hours. The reaction medium is filtered through celite and the filtrate is concentrated under reduced pressure in a rotary evaporator. 2.0 g of 3-[6-(3-dimethylaminopropoxy)-5-fluoro-1H-benzimidazol-2-yl]-1-(tetrahydropyran-2-yl)-1H-pyrazol-4-ylamine are obtained in the form of a brown solid. $^1H$ NMR (300 MHz, DMSO-d6, δ in ppm): 1.46 to 2.21 (m, 8H); 2.17 (s, 6H); 2.40 (t, J=7.0 Hz, 2H); 3.63 (m, 1H); 3.95 (m, 1H); 4.08 (m, 2H); 4.92 (broad s, 2H); 5.32 (dd, J=2.5 and 10.0 Hz, 1H); from 7.01 to 7.47 (m, 2H); 7.31 (s, 1H); 12.55 (m, 1H).

Stage V

Preparation of 3-[3-[6-(3-dimethylaminopropoxy)-5-fluoro-1H-benzimidazol-2-yl]-1-(tetrahydro-pyran-2-yl)-1H-pyrazol-4-yl]-1,1-diethylurea

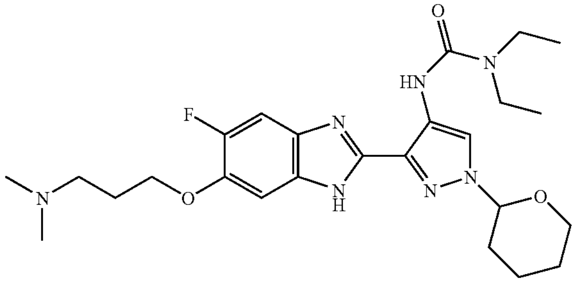 [SMILES: CCN(CC)C(=O)Nc1cn(C2CCCCO2)nc1-c1nc2cc(F)c(OCCCN(C)C)cc2[nH]1]

1.4 mL of diethylcarbonyl chloride and 1.8 mL of N,N-diisopropylethylamine are added to a solution of 0.9 g of intermediate 1 in 30 mL of THF. The reaction mixture is heated at 52° C. for 24 hours. The reaction medium is cooled to ambient temperature and washed with 30 mL of a saturated solution of sodium bicarbonate. The aqueous phase is extracted with three times 30 mL of EtOAc. The organic phases are dried over $MgSO_4$, filtered and concentrated under vacuum in a rotary evaporator. 1.4 g of 3-[3-[6-(3-dimethylaminopropoxy)-5-fluoro-1H-benzimidazol-2-yl]-1-(tetrahydropyran-2-yl)-1H-pyrazol-4-yl]-1,1-diethylurea are obtained in the form of a brown oil. $^1$H NMR (300 MHz, DMSO-d6, δ in ppm): 1.22 (t, J=7.5 Hz, 6H); from 1.50 to 2.22 (m, 8H); 2.85 (s, 6H); 3.27 (m, 2H); from 3.31 to 3.48 (m, 4H); 3.67 (m, 1H); 3.97 (m, 1H); 4.17 (t, J=6.0 Hz, 2H); 5.47 (dd, J=2.5 and 10.0 Hz, 1H); 7.22 (d, J=8.0 Hz, 1H); 7.44 (d, J=11.0 Hz, 1H); 8.14 (s, 1H).

Stage VI

3-{3-[6-(3-dimethylaminopropoxy)-5-fluoro-1H-benzimidazol-2-yl]-1H-pyrazol-4-yl}-1,1-diethylurea trifluoroacetate

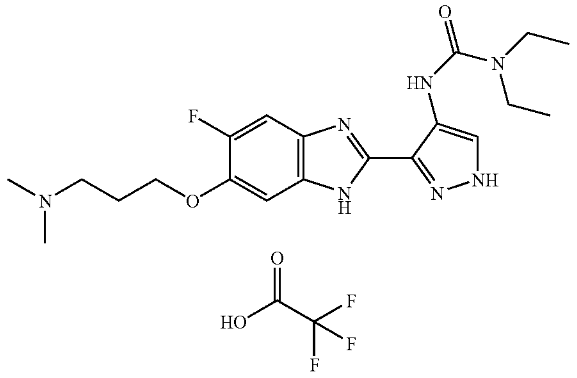

A solution of 1.5 g of 3-[3-[6-(3-dimethylaminopropoxy)-5-fluoro-1H-benzimidazol-2-yl]-1-(tetrahydro-pyran-2-yl)-1H-pyrazol-4-yl]-1,1-diethylurea in solution in 30 mL of a 4N solution of hydrochloric acid in dioxane is stirred at 22° C. for 4 hours. A solid precipitates. The solid is filtered off, washed with dioxane and then dried in an oven under vacuum at 40° C. until the weight is constant. The precipitate obtained is purified by a preparative HPLC using eluents containing respectively 0.05% of acetic acid. After concentration of the fractions containing the product, the latter is dried under vacuum until the weight is constant. 420 mg of 3-[3-[6-(3-dimethylaminopropoxy)-5-fluoro-1H-benzimidazol-2-yl]-1-(tetrahydropyran-2-yl)-1H-pyrazol-4-yl]-1,1-diethylurea are obtained in the form of a 60% acetate and 40% hydrochloride mixed salt.

For this batch, we have a partial salification with respect to acetate, i.e. 2 mol of expected product per mol of acetate insofar as we localize: $^1$H NMR (300 MHz, DMSO-d6, δ in ppm): 1.19 (t, J=7.0 Hz, 6H); 1.90 (s, 1.5H); 2.17 (m, 2H); 2.84 (s, 6H); 3.27 (m, 2H); 3.39 (q, J=7.0 Hz, 4H); 4.18 (t, J=6.0 Hz, 2H); 7.27 (d, J=8.0 Hz, 1H); 7.48 (d, J=11.0 Hz, 1H); 8.00 (s, 1H).

Example 6

1,1-diethyl-3-{3-[5-fluoro-6-(3-piperidin-1-ylpropoxy)-1H-benzimidazol-2-yl]-1H-pyrazol-4-yl}urea Hydrochloride

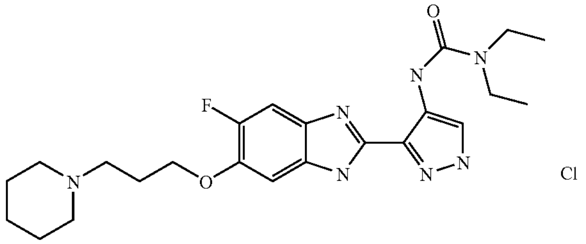 [SMILES: CCN(CC)C(=O)Nc1c[nH]nc1-c1nc2cc(F)c(OCCCN3CCCCC3)cc2[nH]1 ; Cl]

Stage I

Preparation of 4-fluoro-2-nitro-5-(3-piperidin-1-ylpropoxy)phenylamine

A solution of 1.3 mL of 3-piperidin-1-ylpropan-1-ol in 16 mL of N,N-dimethylformamide (DMF) is cooled to 0° C. with an ice bath. 345 mg of sodium hydride (60% in suspension in oil) are added in small portions. The suspension obtained is added dropwise to a suspension containing 500 mg of 4,5-difluoro-2-nitrophenylamine and 724 mg of sodium bicarbonate in 15 mL of DMF. The reaction medium is stirred for one hour at ambient temperature and then heated for 1 hour at 90° C. The cooled reaction medium is treated with 70 mL of ethyl acetate and 70 mL of distilled water. The aqueous phase is extracted with 70 mL of ethyl acetate. The combined organic phases are washed with 100 mL of distilled water and 100 mL of a saturated aqueous solution of sodium chloride and dried over magnesium sulfate. The solvent is concentrated to dryness in a rotary evaporator and the crude is then purified by chromatography on a 50 g silica cartridge, eluent: 100/0 to 80/20 dichloromethane/methanol. 300 mg of 4-fluoro-2-nitro-5-(3-piperidin-1-ylpropoxy)phenylamine are isolated in the form of a yellow oil which crystallizes. Analytical LC/MS: Tr=2.26 min, $[M+H]^+$=298.04 DAD=87%.

Stage II

Preparation of 4-fluoro-5-(3-piperidin-1-ylpropoxy) benzene-1,2-diamine 200 mg of 4-fluoro-2-nitro-5-(3-piperidin-1-ylpropoxy)-phenylamine in solution in 15 mL of methanol are hydrogenated under 1 bar of hydrogen pressure in the presence of 20 mg of palladium-on-charcoal at 25° C. for 10 hours. The reaction crude is filtered through celite and the filtrate is concentrated under vacuum in a rotary evaporator. 180 mg of 4-fluoro-5-(3-piperidin-1-ylpropoxy)benzene-1,2-diamine are obtained in the form of a black oil. The product is used without any other purification.

Stage III

Preparation of 5-fluoro-2-[4-nitro-1-(tetrahydropyran-2-yl)-1H-pyrazol-3-yl]-6-(3-piperidin-1-ylpropoxy)-1H-benzimidazol A solution of 200 mg of 4-fluoro-5-(3-piperidin-1-ylpropoxy)benzene-1,2-diamine and 181 mg of 4-nitro-1-(tetrahydropyran-2-yl)-1H-pyrazole-3-carbaldehyde in 15 mL of methanol is stirred at ambient temperature over night. The reaction medium is concentrated to dryness under vacuum in a rotary evaporator. The reaction crude is purified by flash chromatography on a 20 g silica cartridge, eluent: 100/0 to 80/20 dichloromethane/methanol. 280 mg of 5-fluoro-2-[4-nitro-1-(tetrahydropyran-2-yl)-1H-pyrazol-3-yl]-6-(3-piperidin-1-ylpropoxy)-1H-benzimidazoleare isolated in the form of a red lake. Analytical LC/MS: Tr=2.51 min, $[M+H]^+$=472.97 DAD=36%.

Stage IV

Preparation of 3-[5-fluoro-6-(3-piperidin-1-ylpropoxy)-1H-benzimidazol-2-yl]-1-(tetrahydropyran-2-yl)-1H-pyrazol-4-ylamine A suspension of 280 mg of 5-fluoro-2-[4-nitro-1-(tetrahydropyran-2-yl)-1H-pyrazol-3-yl]-6-(3-piperidin-1-ylpropoxy)-1H-benzimidazolein 22 mL of ethyl acetate and 30 mg of palladium-on-charcoal is hydrogenated under 1 bar of hydrogen pressure at 25° C. for 13 hours. The reaction medium is filtered through celite and the filtrate is concentrated under reduced pressure in a rotary evaporator. 260 mg of 3-[5-fluoro-6-(3-piperidin-1-ylpropoxy)-1H-benzimidazol-2-yl]-1-(tetrahydropyran-2-yl)-1H-pyrazol-4-ylamine are obtained in the form of a chestnut-brown foam. The compound is used without any other purification for the subsequent stage. Analytical LC/MS: Tr=2.30 min, $[M+H]^+$=443.34 DAD=64%.

Stage V

Preparation of 1,1-diethyl-3-[3-[5-fluoro-6-(3-piperidin-1-ylpropoxy)-1H-benzimidazol-2-yl]-1-(tetrahydropyran-2-yl)-1H-pyrazol-4-yl]urea 130 mg of 3-[5-fluoro-6-(3-piperidin-1-ylpropoxy)-1H-benzimidazol-2-yl]-1-(tetrahydropyran-2-yl)-1H-pyrazol-4-ylamine are solubilized in 10 mL of tetrahydrofuran and then 372 μl of diethylcarbamoyl chloride and 487 μL of N,N-diisopropylethylamine are added. The reaction medium is heated at 50° C. over night. The solvent is evaporated off under vacuum in a rotary evaporator and the reaction crude is purified by flash chromatography on a 4 g silica cartridge, eluent: 100/0 to 80/20 dichloromethane/methanol. 70 mg of 1,1-diethyl-3-[3-[5-fluoro-6-(3-piperidin-1-ylpropoxy)-1H-benzimidazol-2-yl]-1-(tetrahydropyran-2-yl)-1H-pyrazol-4-yl]urea are isolated in the form of a chestnut-brown oil. Analytical LC/MS: Tr=2.91 min, $[M+H]^+$=542.00 DAD=95%.

Stage VI 1,1-diethyl-3-{3-[5-fluoro-6-(3-piperidin-1-ylpropoxy)-1H-benzimidazol-2-yl]-1H-pyrazol-4-yl}urea Hydrochloride 70 mg of 1,1-diethyl-3-[3-[5-fluoro-6-(3-piperidin-1-ylpropoxy)-1H-benzimidazol-2-yl]-1-(tetrahydropyran-2-yl)-1H-pyrazol-4-yl]urea are suspended in 3 mL of a 3N solution of HCl in dioxane. The medium is stirred at ambient temperature for 48 hours. The solvent is evaporated off under vacuum in a rotary evaporator. The reaction crude is purified by flash chromatography on a 4 g silica cartridge, eluent: 100/0 to 80/20 dichloromethane/methanol. The fractions containing the expected product are concentrated and the solid obtained is triturated in isopropyl ether. After filtration and rinsing of the solid, 26.2 mg of 1,1-diethyl-3-{3-[5-fluoro-6-(3-piperidin-1-ylpropoxy)-1H-benzimidazol-2-yl]-1H-pyrazol-4-yl}urea hydrochloride are isolated in the form of a sand-colored solid. $^1$H NMR (400 MHz, DMSO-d6, δ in ppm) after addition of a drop of TFA-d1 (CF3COOD-d1): 1.15 (t, J=7.0 Hz, 6H); 1.39 (m, 1H); from 1.57 to 1.76 (m, 3H); 1.83 (m, 2H); 2.22 (m, 2H); 2.93 (m, 2H); 3.25 (m, 2H); 3.37 (q, J=7.0 Hz, 4H); 3.51 (m, 2H); 4.21 (t, J=6.0 Hz, 2H); 7.34 (d, J=7.5 Hz, 1H); 7.56 (d, J=11.0 Hz, 1H); 8.00 (s, 1H).

Example 7

N-{3-[6-(3-dimethylaminopropoxy)-5-fluoro-1H-benzimidazol-2-yl]-1H-pyrazol-4-yl}-piperidine-1-carboxamide Trifluoroacetate

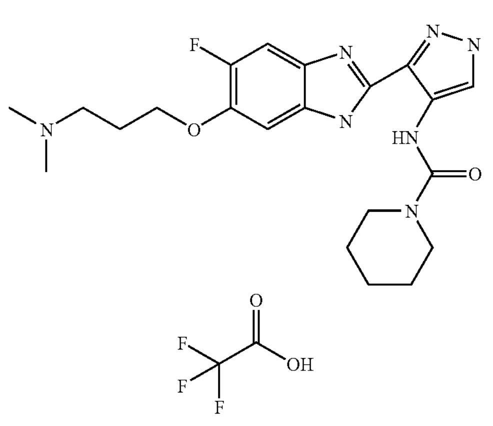

Stage V

Preparation of piperidine-1-carboxylic acid [3-[6-(3-dimethylaminopropoxy)-5-fluoro-1H-benzimidazol-2-yl]-1-(tetrahydropyran-2-yl)-1H-pyrazol-4-yl] amide

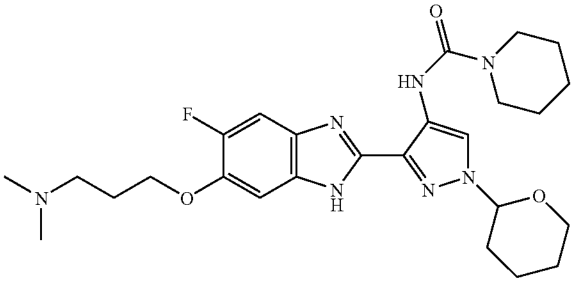 [SMILES: CN(C)CCCOc1cc2[nH]c(-c3nn(C4CCCCO4)cc3NC(=O)N3CCCCC3)nc2cc1F]

171.3 μL of piperidylcarbonyl chloride and 200 μL of N,N-diisopropylethylamine are added to a solution of 100 mg of intermediate 1 in 10 mL of THF. The reaction mixture is heated at 52° C. for 48 hours. The reaction medium is cooled to ambient temperature and then 20 mL of a saturated solution of sodium bicarbonate are added. The aqueous phase is extracted with 3 times 10 mL of EtOAc. The organic phases are dried over $MgSO_4$, filtered and concentrated under vacuum in a rotary evaporator. The reaction crude is purified by flash chromatography on an Intelliflash apparatus on an Analogix RS-4 cartridge. Elution is carried out with a dichloromethane/methanol mixture. 28 mg of piperidine-1-carboxylic acid [3-[6-(3-dimethylaminopropoxy)-5-fluoro-1H-benzimidazol-2-yl]-1-(tetrahydropyran-2-yl)-1H-pyrazol-4-yl]amide are obtained in the form of a brown resin. $^1$H NMR (300 MHz, DMSO-d6, δ in ppm): 1.50 to 2.36 (m, 14H); 2.29 (broad s, 6H); 2.55 (m partially masked, 2H); 3.50 (m, 4H); 3.66 (m, 1H); 3.96 (m, 1H); 4.11 (m, 2H); 5.46 (broad d, J=10.0 Hz, 1H); from 7.08 to 7.55 (m, 2H); 8.14 (broad s, 1H); from 9.66 to 9.93 (m, 1H); 13.05 (m, 1H).

Stage VI

N-{3-[6-(3-dimethylaminopropoxy-5-fluoro-1H-benzimidazol-2-yl]-1H-pyrazol-4-yl}-piperidine-1-carboxamide Trifluoroacetate

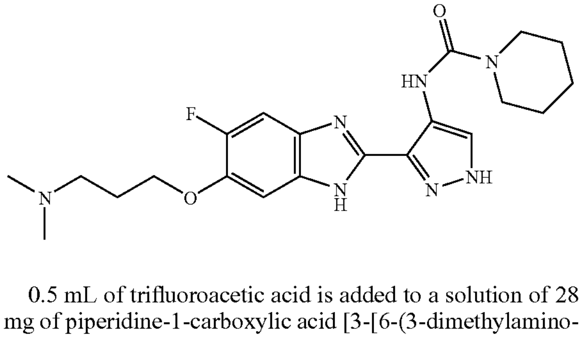

0.5 mL of trifluoroacetic acid is added to a solution of 28 mg of piperidine-1-carboxylic acid [3-[6-(3-dimethylaminopropoxy)-5-fluoro-1H-benzimidazol-2-yl]-1-(tetrahydropyran-2-yl)-1H-pyrazol-4-yl]amide in solution in 1.5 mL of dichloromethane. The reaction medium is stirred at 22° C. for 16 hours. The reaction medium is concentrated under reduced pressure in a rotary evaporator, taken up several times with isopropyl ether and concentrated under reduced pressure in a rotary evaporator each time. 40 mg of N-{3-[6-(3-dimethylaminopropoxy)-5-fluoro-1H-benzimidazol-2-yl]-1H-pyrazol-4-yl}piperidine-1-carboxamide are obtained in the form of trifluoroacetic acid salt. $^1$H NMR (300 MHz, DMSO-d6, δ in ppm): 1.47 to 1.72 (m, 6H); 2.19 (m, 2H); 2.84 (s, 6H); 3.27 (m, 2H); 3.42 (m, 4H); 4.22 (t, J=6.0 Hz, 2H); 7.40 (d, J=7.5 Hz, 1H); 7.65 (d, J=10.0 Hz, 1H); 8.00 (s, 1H).

Example 8

3-[3-(5-fluoro-6-perhydro-1,4-oxazepan-4-yl-1H-benzimidazol-2-yl)-1H-pyrazol-4-yl]-1,1-diisopropylurea

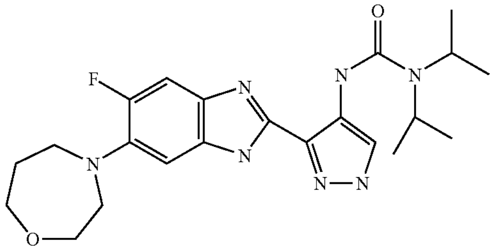 [SMILES: CC(C)N(C(=O)Nc1c[nH]nc1-c1nc2cc(F)c(N3CCCOCC3)cc2[nH]1)C(C)C]

Stage V

3-[3-(5-fluoro-6-perhydro-1,4-oxazepin-4-yl-1H-benzimidazol-2-yl)-1-(tetrahydropyran-2-yl)-1H-pyrazol-4-yl]-1,1-diisopropylurea

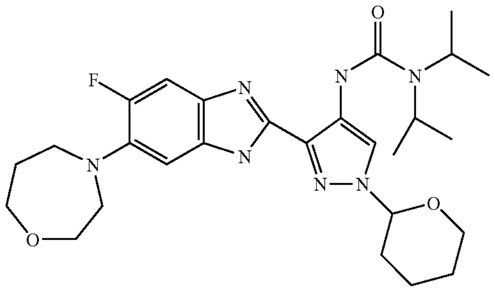 [SMILES: CC(C)N(C(=O)Nc1cn(C2CCCCO2)nc1-c1nc2cc(F)c(N3CCCOCC3)cc2[nH]1)C(C)C]

257.4 mg of diisopropylcarbamoyl chloride and 1.4 L of N,N-diisopropylethylamine are added to a solution of 630 mg of intermediate 6 in 66.6 mL of THF. The reaction mixture is heated at 66° C. for 7.5 hours, then stirred for 16 hours at ambient temperature, then heated at 66° C. for 7.75 hours, then stirred for 16 hours at ambient temperature. The reaction medium is washed with 20 mL of saturated $NaHCO_3$ solution water. The aqueous phase is extracted with three times 60 mL of EtOAc. The organic phases are dried over $MgSO_4$, filtered and concentrated under vacuum in a rotary evaporator. The reaction crude is purified by flash chromatography, elution being carried out with a dichloromethane/methanol mixture: 600 mg of 3-[3-(5-fluoro-6-perhydro-1,4-oxazepin-4-yl-1H-benzimidazol-2-yl)-1-(tetrahydropyran-2-yl)-1H-pyrazol-4-yl]-1,1-diisopropylurea are obtained. Analytical LC/MS: Tr=4.57 min; $[M+H]^+$=528.51; ELSD=59%; DAD=59%.

Stage VI

3-[3-(5-fluoro-6-perhydro-1,4-oxazepin-4-yl-1H-benzimidazol-2-yl)-1H-pyrazol-4-yl]-1,1-diisopropylurea A solution of 600 mg of 3-[3-(5-fluoro-6-perhydro-1,4-oxazepin-4-yl-1H-benzimidazol-2-yl)-1-(tetrahydropyran-2-yl)-1H-pyrazol-4-yl]-1,1-diisopropylurea in solution in 5 mL of a 4N solution of hydrochloric acid in dioxane is stirred at 22° C. for 4 hours. After evaporation, the reaction crude is purified by preparative HPLC and then by preparative LC/MS, with, as eluent, a gradient of water, with acetonitrile, containing respectively 0.07% of trifluoroacetic acid. 48 mg of 3-[3-(5-fluoro-6-perhydro-1,4-oxazepin-4-yl-1H-benzimidazol-2-yl)-1H-pyrazol-4-yl]-1,1-diisopropylurea are obtained in the form of a brown solid. $^1$H NMR (400 MHz, DMSO-d6, δ in ppm): 1.35 (d, J=7.0 Hz, 12H); 1.98 (m, 2H); 3.33 (m, 4H); 3.78 (m, 4H); 4.06 (m, 2H); 7.08 (broad d J=8.0 Hz, 1H); 7.28 (broad d, J=12.0 Hz, 1H); 8.01 (s, 1H); 9.56 (s, 1H); 12.85 (broad m, 2H).

Example 9

1,1-diethyl-3-{3-[6-fluoro-5-(4-piperidin-1-ylbutoxy)-1H-benzimidazol-2-yl]-1H-pyrazol-4-yl}urea Trifluoroacetate

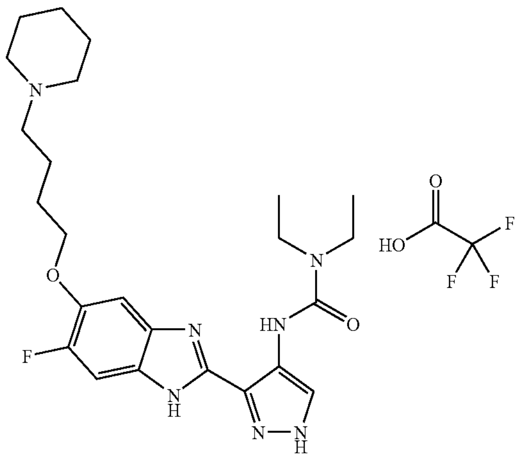

Preparation of 4-piperidin-1-ylbutan-1-ol: 11.68 mL of a 1M solution of lithium aluminum hydride in ether are added to 10 mL of tetrahydrofuran, and then 1 g of 4-piperidin-1-ylbutyric acid hydrochloride (synthesized according to a method described in the literature) is added. The medium is brought to boiling for approximately 10 minutes. After a return to ambient temperature and cooling to 0° C., a mixture of 1 mL of distilled water-30 mL of tetrahydrofuran is added dropwise. A large amount of gas is given off and strong exothermia is observed. After a return to ambient temperature, the medium is evaporated to dryness under reduced pressure in a rotary evaporator. The reaction crude is triturated in 150 mL of ethyl acetate and filtered, and the filtrate is washed with 2×20 mL of distilled water. The organic phase is dried over magnesium sulfate, filtered and then concentrated under vacuum in a rotary evaporator. 646 mg of 4-piperidin-1-ylbutan-1-ol are isolated in the form of a colorless oil. $^1$H NMR (300 MHz, DMSO-d6, δ in ppm): from 1.30 to 1.53 (m, 10H); 2.20 (t, J=6.5 Hz, 2H); 2.28 (m, 4H); 3.37 (broad t, J=6.5 Hz, 2H); 4.57 (broad s, 1H).

Stage I 4-fluoro-2-nitro-5-(4-piperidin-1-ylbutoxy)-phenylamine 382 mg of sodium hydride (60% in suspension in oil) are added in small portions, over two hours, to a solution of 4-piperidin-1-ylbutan-1-ol in 10 mL of DMF, cooled to 0° C. with an ice bath. A solution of 4,5-difluoro-2-nitroaniline in 5 mL of N,N-dimethylformamide is then added dropwise. The medium is stirred at ambient temperature for 24 hours. 60 mL of distilled water are added and the reaction medium is extracted with 3×30 mL of ethyl acetate. The combined organic phases are dried over magnesium sulfate, filtered and concentrated under vacuum in a rotary evaporator. The reaction crude is purified by flash chromatography on an Intelliflash apparatus with an Analogix RS-12 silica cartridge, with a 100% to 85/15 dichloromethane/-methanol elution gradient. 700 mg of 4-fluoro-2-nitro-5-(4-piperidin-1-ylbutoxy)phenylamine are isolated in the form of a red oil. $^1$H NMR (300 MHz, DMSO-d6, δ in ppm): from 1.29 to 1.62 (m, 8H); 1.75 (m, 2H); 2.28 (m, 6H); 4.07 (t, J=6.5 Hz, 2H); 6.62 (d, J=7.5 Hz, 1H); 7.48 (broad s, 2H); 7.74 (d, J=12.0 Hz, 1H).

Stage II 4-fluoro-5-(4-piperidin-1-ylbutoxy)benzene-1,2-diamine 758 mg of 4-fluoro-2-nitro-5-(4-piperidin-1-ylbutoxy)-phenylamine in solution in 40 mL of methanol are hydrogenated under 1 bar of hydrogen pressure in the presence of 75 mg of palladium-on-charcoal at 25° C. for 16 hours. The reaction crude is filtered through celite and the filtrate is concentrated under vacuum in a rotary evaporator. 670 mg of 4-fluoro-5-(4-piperidin-1-ylbutoxy)benzene-1,2-diamine are isolated in the form of a black oil. $^1$H NMR (300 MHz, DMSO-d6, δ in ppm): from 1.29 to 1.56 (m, 8H); 1.62 (m, 2H); from 2.20 to 2.32 (m, 6H); 3.82 (t, J=6.5 Hz, 2H); 4.27 (broad m, 4H); 6.32 (d, J=9.0 Hz, 1H); 6.34 (d, J=13.0 Hz, 1H).

Stage III 6-fluoro-2-[4-nitro-1-(tetrahydropyran-2-yl)-1H-pyrazol-3-yl]-5-(4-piperidin-1-ylbutoxy)-1H-benzimidazol A solution of 74 mg of 4-fluoro-5-(4-piperidin-1-ylbutoxy)benzene-1,2-diamine and 50.7 mg of 4-nitro-1-(tetrahydropyran-2-yl)-1H-pyrazole-3-carbaldehyde in 4 mL of methanol is stirred at ambient temperature for 18 hours. After evaporation of the solvent under reduced pressure in a rotary evaporator, the reaction crude is purified by flash chromatography on an Intelliflash apparatus on an Analogix RS-4 cartridge with a dichloromethane/methanol eluent of 100% to 82/18. 77 mg of 6-fluoro-2-[4-nitro-1-(tetrahydropyran-2-yl)-1H-pyrazol-3-yl]-5-(4-piperidin-1-ylbutoxy)-1H-benzimidazoleare isolated in the form of a yellow foam. $^1$H NMR (300 MHz, DMSO-d6, δ in ppm) for this batch, we observe a 60%-40% resolution of tautomers with: from 1.29 to 2.44 (m, 22H); 3.70 (m, 1H); 4.00 (m, 1H) 4.10 (t, J=6.0 Hz, 2H); 5.60 (dd, J=3.0 and 10.0 Hz, 1H); 7.21 (d, J=8.5 Hz, 0.6H); from 7.36 to 7.46 (m, 0.8H); 7.53 (d, J=11.0 Hz, 0.6H); 9.17 (s, 1H); 12.8 (broad s, 0.6H); 12.9 (broad s, 0.4H).

Stage IV

Preparation of 3-[6-fluoro-5-(4-piperidin-1-ylbutoxy)-1H-benzimidazol-2-yl]-1-(tetrahydropyran-2-yl)-1H-pyrazol-4-ylamine (Beta Intermediate)

470 mg of 6-fluoro-2-[4-nitro-1-(tetrahydropyran-2-yl)-1H-pyrazol-3-yl]-5-(4-piperidin-1-ylbutoxy)-1H-benzimidazolein 30 mL of ethyl acetate and 40 mg of palladium-on-charcoal are hydrogenated under 1 bar of hydrogen pressure at 25° C. for 16 hours. The reaction medium is filtered through celite and the filtrate is concentrated under reduced pressure in a rotary evaporator. 380 mg of 3-[6-fluoro-5-(4-piperidin-1-ylbutoxy)-1H-benzimidazol-2-yl]-1-(tetrahydropyran-2-yl)-1H-pyrazol-4-ylamine are obtained. The compound is used without any other purification for the subsequent stage. $^1$H NMR (400 MHz, DMSO-d6, δ in ppm) for this batch, we observe a 60%-40% resolution of tautomers with: from 1.31 to 2.40 (m, 16H); 2.33 (m, 6H); 3.63 (m, 1H); 3.92 (m, 1H); 4.07 (m, 2H); 4.92 (broad m, 2H); 5.32 (dd, J=2.5 and 10.0 Hz, 1H); 7.06 (d, J=6.0 Hz, 0.6H); 7.19 (d, J=11.0 Hz, 0.4H); 7.32 (s, 1H); 7.37 (d, J=8.0 Hz, 0.4H); 7.43 (d, J=11.0 Hz, 0.6H); 12.55 (broad s, 0.4H); 12.6 (broad s, 0.6H).

Stage V 1,1-diethyl-3-[3-[6-fluoro-5-(4-piperidin-1-ylbutoxy)-1H-benzimidazol-2-yl]-1-(tetrahydropyran-2-yl)-1H-pyrazol-4-yl]urea A solution of 110 mg of beta intermediate, 305 µl of diethylcarbamoyl chloride and 400 µL of triethylamine in 6 mL of tetrahydrofuran is stirred for 72 hours at 52° C. After a return to ambient temperature, the medium is treated with 20 mL of distilled water and the aqueous phase is extracted with 3×10 mL of ethyl acetate. The combined organic phases are dried over magnesium sulfate and filtered, and the solvent is evaporated off under reduced pressure in a rotary evaporator. The reaction crude is purified by flash chromatography on an Intelliflash apparatus on an Analogix RS-12 cartridge with a dichloromethane/-methanol eluent of 100% to 90/10. 100 mg of 1,1-diethyl-3-[3-[6-fluoro-5-(4-piperidin-1-ylbutoxy)-1H-benzimidazol-2-yl]-1-(tetrahydropyran-2-yl)-1H-pyrazol-4-yl]urea are isolated in the form of a brown foam. $^1$H NMR (400 MHz, DMSO-d6, δ in ppm) after addition of a drop of TFA-d1 (trifluoroacetic acid CF3COOD-d1): 1.14 (t, J=7.0 Hz, 6H); from 1.35 to 2.28 (m, 16H); from 2.80 to 2.94 (m, 2H); 3.12 (m, 2H); 3.35 (q, J=7.0 Hz, 4H); 3.44 (m, 2H); 3.65 (m, 1H); 3.96 (m, 1H); 4.15 (m, 2H); 5.49 (dd, J=2.5 and 10.0 Hz, 1H); 7.31 (d, J=7.5 Hz, 1H); 7.54 (d, J=10.5 Hz, 1H); 8.13 (s, 1H).

Stage VI 1,1-diethyl-3-{3-[6-fluoro-5-(4-piperidin-1-ylbutoxy)-1H-benzimidazol-2-yl]-1H-pyrazol-4-yl}urea Trifluoroacetate 100 mg of 1,1-diethyl-3-[3-[6-fluoro-5-(4-piperidin-1-ylbutoxy)-1H-benzimidazol-2-yl]-1-(tetrahydropyran-2-yl)-1H-pyrazol-4-yl}urea in solution in 2 mL of dichloromethane with 1 mL of trifluoroacetic acid are stirred at ambient temperature for 18 hours. The solvent is evaporated off under vacuum by flash chromatography on an Intelliflash apparatus on an Analogix RS-12 cartridge with an eluent of 100% dichloromethane to 85/15 dichloromethane/methanol. 72 mg of 1,1-diethyl-3-{3-[6-fluoro-5-(4-piperidin-1-ylbutoxy)-1H-benzimidazol-2-yl]-1H-pyrazol-4-yl}urea in the form of a trifluoroacetate salt are isolated in the form of a yellow solid. $^1$H NMR (400 MHz, DMSO-d6, δ in ppm). For this batch, we observe a 60%-40% resolution of tautomers with: 1.23 (m, 6H); from 1.30 to 1.91 (broad m, 10H); 2.70 to 3.53 (very broad m, 6H); 3.41 (m, 4H); 4.12 (m, 2H); 7.11 (d, J=8.0 Hz, 0.6H); from 7.24 to 7.30 (m, 0.8H); 7.44 (d, J=11.0 Hz, 0.6H); 8.00 (s, 1H); 8.94 (broad m, 1H); 9.77 (s, 0.4H); 9.79 (s, 0.6H); 12.9 (broad s, 0.4H); 12.95 (broad s, 0.6H); 13.0 (broad s, 1H).

Example 10

N-{3-[6-fluoro-5-(4-piperidin-1-ylbutoxy)-1H-benzimidazol-2-yl]-1H-pyrazol-4-yl}piperidin-1-carboxamide Trifluoroacetate

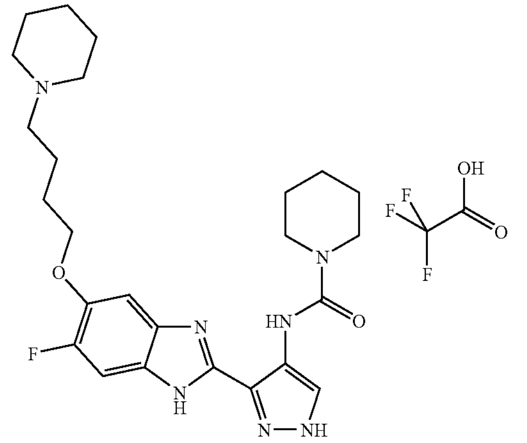

Stage V

N-{3-[6-fluoro-5-(4-piperidin-1-ylbutoxy)-1H-benzimidazol-2-yl]-1-(tetrahydropyran-2-yl)-1H-pyrazol-4-yl}piperidine-1-carboxamide 130 g of beta intermediate are solubilized in 7 mL of tetrahydrofuran with 356 µL of piperidinecarbonyl chloride and 472 µL of N,N-diisopropylamine, and stirred at ambient temperature for 18 hours. After evaporation of the solvent under vacuum in a rotary evaporator, the reaction crude is purified by flash chromatography on an Analogix RS-12 cartridge, with an eluent of 100% dichloromethane to 90/10 dichloromethane/methanol. 130 mg of piperidine-1-carboxylic acid [3-[6-fluoro-5(4-piperidin-1-ylbutoxy)-1H-benzimidazol-2-yl]-1-(tetrahydropyran-2-yl)-1H-pyrazol-4-yl)-amide are isolated in the form of a yellow foam. $^1$H NMR (300 MHz, DMSO-d6, δ in ppm): for this batch, we observe a 60%-40% resolution of tautomers with: from 1.33 to 2.21 (broad m, 22H); from 2.65 to 3.35 (very broad m, 6H); 3.49 (m, 4H); 3.65 (m, 1H); 3.98 (m, 1H); 4.12 (m, 2H); 5.46 (broad d, J=10.0 Hz, 1H); 7.11 (d, J=7.5 Hz, 0.6H); 7.27 (d, J=11.0 Hz, 0.4H); 7.36 (d, J=7.5 Hz, 0.4H); 7.52 (d, J=11.0 Hz, 0.6H); 8.14 (s, 1H); 9.86 (s, 0.4H); 9.91 (s, 0.6H); 13.0 (broad s, 0.4H); 13.05 (broad s, 0.6H).

Stage VI

N-{3-[6-fluoro-5-(4-piperidin-1-ylbutoxy)-1H-benzimidazol-2-yl]-1H-pyrazol-4-yl}piperidine-1-carboxamide Trifluoroacetate A solution of 130 mg of piperidine-1-carboxylic acid [3-[6-fluoro-5-(4-piperidin-1-ylbutoxy)-1H-benzimidazol-2-yl]-1-(tetrahydropyran-2-yl)-1H-pyrazol-4-yl]amide in 2 mL of dichloromethane and 500 μL of trifluoroacetic acid are stirred for 72 hours at ambient temperature. After evaporation of the solvent under vacuum in a rotary evaporator, the reaction crude is purified by flash chromatography on an Analogix RS-12 cartridge with an eluent of 100% dichloromethane to 90/10 dichloromethane/methanol. 86 mg of N-{3-[6-fluoro-5-(4-piperidin-1-ylbutoxy)-1H-benzimidazol-2-yl]-1H-pyrazol-4-yl}piperidine-1-carboxamide in the form of a trifluoroacetate salt are obtained in the form of a yellow solid. $^1$H NMR (300 MHz, DMSO-d6, δ in ppm): for this batch, we observe a 60%-40% resolution of tautomers with: from 1.20 to 1.94 (broad m, 16H); from 2.70 to 3.43 (m partially masked, 6H); 3.50 (m, 4H); 4.11 (m, 2H); 7.11 (d, J=7.5 Hz, 0.6H); 7.27 (d, J=11.0 Hz, 0.4H); 7.37 (d, J=7.5 Hz, 0.4H); 7.51 (d, J=11.0 Hz, 0.6H); 8.01 (broad s, 1H); 8.94 (broad m, 1H); 9.83 (s, 0.4H); 9.87 (s, 0.6H); 12.95 (s, 0.4H); 13.0 (s, 0.6H); 13.05 (s, 1H).

Example 11

1,1-diethyl-3[3-(5-fluoro-6-perhydro-1,4-oxazepin-4-yl-1H-benzimidazol-2-yl)-1H-pyrazol-4-yl]urea

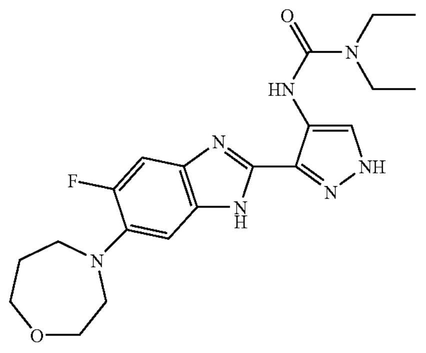 [SMILES: CCN(CC)C(=O)Nc1c[nH]nc1-c1nc2cc(F)c(N3CCCOCC3)cc2[nH]1]

Stage I 4-fluoro-2-nitro-5-perhydro-1,4-oxazepin-4-ylphenylamine

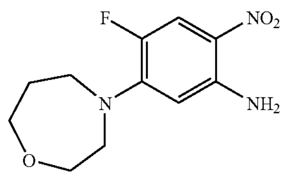 [SMILES: Nc1cc(N2CCCOCC2)c(F)cc1[N+](=O)[O-]]

19.4 g of potassium carbonate and 11.9 g of homomorpholine hydrochloride are added to a solution of 5 g of 4,5-difluoro-2-nitroaniline in 98 mL of anhydrous DMF. The reaction medium is heated at 80° C. using an oil bath for 2 hours. The reaction medium is cooled to ambient temperature, then 300 mL of water are added thereto, and precipitation occurs. The precipitate is filtered through sintered glass. The yellow solid is rinsed with 3 times 100 mL of water. The solid is dried in an oven at 70° C. 6.5 g of 4-fluoro-2-nitro-5-perhydro-1,4-oxazepin-4-ylphenylamine are obtained in the form of an orange solid. $^1$H NMR (400 MHz, DMSO-d6, δ in ppm): 1.91 (m, 2H); from 3.52 to 3.61 (m, 4H); 3.66 (m, 2H); 3.74 (m, 2H); 6.28 (d, J=8.5 Hz, 1H); 7.24 (broad s, 2H); 7.61 (d, J=15.5 Hz, 1H).

Stage II 4-fluoro-5-perhydro-1,4-oxazepin-4-ylbenzene-1,2-diamine

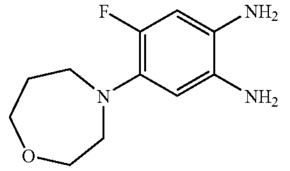 [SMILES: Nc1cc(F)c(N2CCCOCC2)cc1N]

7 g of 4-fluoro-2-nitro-5-perhydro-1,4-oxazepin-4-ylphenylamine in solution in 170 mL of methanol are hydrogenated under 1 bar of hydrogen pressure in the presence of 700 mg of palladium-on-charcoal at 22° C. for 10 hours. The reaction crude is filtered through celite and the filtrate is concentrated under vacuum in a rotary evaporator. After evaporation, the reaction crude is purified by flash chromatography (elution dichloromethane/methanol). 3 g of 4-fluoro-5-perhydro-1,4-oxazepin-4-ylbenzene-1,2-diamine are isolated. $^1$H NMR spectrum (400 MHz, DMSO-d6, δ in ppm): 1.88 (m, 2H); 3.11 (m, 4H); from 3.64 to 3.74 (m, 4H); 4.20 (broad s, 2H); 4.26 (broad s, 2H); from 6.25 to 6.31 (m, 2H).

Stage III 5-fluoro-2-[4-nitro-1-(tetrahydropyran-2-yl)-1H-pyrazol-3-yl]-6-perhydro-1,4-oxazepin-4-yl-1H-benzimidazol

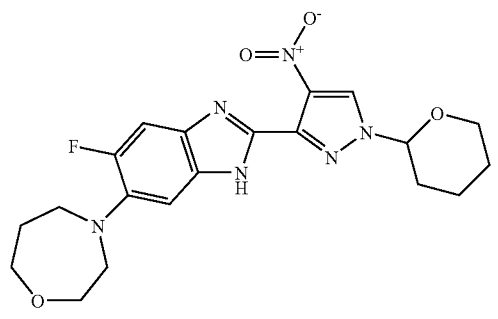 [SMILES: O=[N+]([O-])c1cn(C2CCCCO2)nc1-c1nc2cc(F)c(N3CCCOCC3)cc2[nH]1]

3 g of 4-nitro-1-(tetrahydropyran-2-yl)-1H-pyrazole-3-carbaldehyde and 43 mg of ferric chloride are added to a solution of 3 g of 4-fluoro-5-perhydro-1,4-oxazepin-4-ylbenzene-1,2-diamine in 60 mL of DMF. The reaction medium is stirred at 22° C. for 16 hours. After evaporation, the reaction crude is purified by flash chromatography. The elution is carried out in a 1/1 mixture of cyclohexane/ethyl acetate. 3 g of 5-fluoro-2-[4-nitro-1-(tetrahydropyran-2-yl)-1H-pyrazol-3-yl]-6-perhydro-1,4-oxazepin-4-yl-1H-benzimidazoleare isolated in the form of a red oil. $^1$H NMR (400 MHz, DMSO-d6, δ in ppm): from 1.40 to 2.25 (m, 8H); from 3.25 to 3.39 (m partially masked, 4H); 3.70 (m, 1H); 3.78 (m, 4H); 3.99 (m, 1H); 5.59 (dd, J=2.5 and 9.5 Hz, 1H); 7.16 (broad m, 1H); 7.39 (broad d, J=11.5 Hz, 1H); 9.17 (s, 1H); 12.75 (broad m, 1H).

Stage IV 3-(5-fluoro-6-perhydro-1,4-oxazepin-4-yl-1H-benzimidazol-2-yl)-1-(tetrahydropyran-2-yl)-1H-pyrazol-4-ylamine (Intermediate 6)

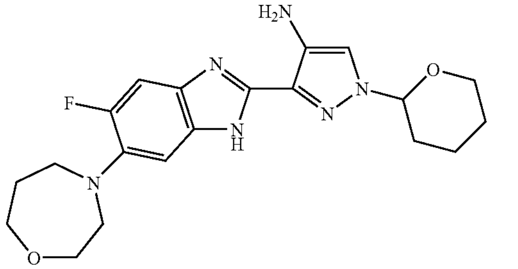 [SMILES: Nc1cn(C2CCCCO2)nc1-c1nc2cc(F)c(N3CCCOCC3)cc2[nH]1]

A suspension of 2.9 g of 5-fluoro-2-[4-nitro-1-(tetrahydropyran-2-yl)-1H-pyrazol-3-yl]-6-perhydro-1,4-oxazepin-4-yl-1H-benzimidazolein 100 mL of methanol and 497 mg of palladium-on-charcoal is hydrogenated under 1 bar of hydrogen pressure at ambient temperature for 16 hours. The reaction medium is filtered through celite and the filtrate is concentrated under reduced pressure in a rotary evaporator. 2.2 g of 3-(5-fluoro-6-perhydro-1,4-oxazepin-4-yl-1H-benzimidazol-2-yl)-1-(tetrahydropyran-2-yl)-1H-pyrazol-4-ylamine are obtained in the form of a black resin. $^1$H NMR (400 MHz, DMSO-d6, δ in ppm): from 1.26 to 2.24 (m, 8H); 3.55 (m, 4H); 3.68 (m, 1H); 3.78 (m, 2H); 3.84 (m, 2H); 3.97 (m, 1H); 5.55 (dd, J=2.5 and 10.5 Hz, 1H); 7.38 (broad d, J=8.0 Hz, 1H); 7.52 (d, J=12.5 Hz, 1H); 8.17 (s, 1H).

Stage V 1,1-diethyl-3-[3-(5-fluoro-6-perhydro-1,4-oxazepin-4-yl-1H-benzimidazol-2-yl)-1-(tetrahydropyran-2-yl)-1H-pyrazol-4-yl]urea

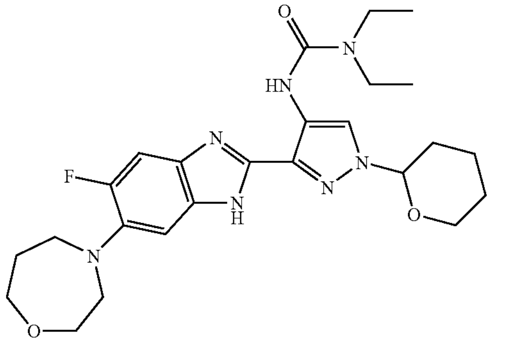 [SMILES: CCN(CC)C(=O)Nc1cn(C2CCCCO2)nc1-c1nc2cc(F)c(N3CCCOCC3)cc2[nH]1]

2.8 mL of diethylcarbamoyl chloride and 4 mL of N,N-diisopropylethylamine are added to a solution of 1.8 g of intermediate 6 in 36 mL of THF. The reaction mixture is heated at 80° C. for 16 hours. The reaction medium is concentrated under vacuum in a rotary evaporator, and then purified by flash chromatography (elution dichloromethane/methanol). The mixture containing the expected product is concentrated and then repurified on 200 g of silica (0.2-0.045 μm), under 0.5 bar of pressure, elution being carried out with a 30/40 then 80/20 mixture of cyclohexane/ethyl acetate. 380 mg of 1,1-diethyl-3-[3-(5-fluoro-6-perhydro-1,4-oxazepin-4-yl-1H-benzimidazol-2-yl)-1-(tetrahydropyran-2-yl)-1H-pyrazol-4-yl]urea are obtained in the form of a beige foam. $^1$H NMR (300 MHz, DMSO-d6, δ in ppm): 1.14 (t, J=7.0 Hz, 6H); from 1.48 to 2.22 (m, 8H); 3.36 (q, J=7.0 Hz, 4H); 3.54 (m, 4H); 3.65 (m, 1H); 3.77 (m, 2H); 3.85 (m, 2H); 3.96 (m, 1H); 5.49 (dd, J=2.0 and 9.5 Hz, 1H); 7.42 (d, J=7.5 Hz, 1H); 7.52 (d, J=12.0 Hz, 1H); 8.13 (s, 1H).

Stage VI 1,1-diethyl-3-[3-(5-fluoro-6-perhydro-1,4-oxazepin-4-yl-1H-benzimidazol-2-yl)-1H-pyrazol-4-yl]urea

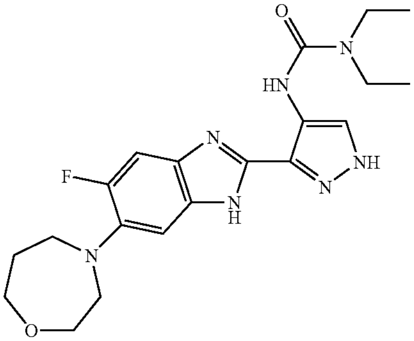 [SMILES: CCN(CC)C(=O)Nc1c[nH]nc1-c1nc2cc(F)c(N3CCCOCC3)cc2[nH]1]

A solution of 380 mg of 1,1-diethyl-3-[3-(5-fluoro-6-perhydro-1,4-oxazepin-4-yl-1H-benzimidazol-2-yl)-1-(tetrahydropyran-2-yl)-1H-pyrazol-4-yl]urea in solution in 5 mL of a 4N solution of hydrochloric acid in dioxane is stirred at 22° C. for 2 hours. The reaction medium is concentrated under vacuum in a rotary evaporator, and then again reacted at 22° C. for 16 hours with 5 mL of a 4N solution of hydrochloric acid in dioxane is stirred at 22° C. The reaction medium is concentrated under vacuum in a rotary evaporator. The product is diluted in ethyl acetate, and washed with 2 times 20 mL of a 2N aqueous solution of sodium hydroxide. The aqueous phases are extracted with 3 times 20 mL of ethyl acetate. The organic phases are dried over $MgSO_4$, filtered and concentrated under vacuum in a rotary evaporator. The yellow foam obtained is made into a paste in isopropyl ether, triturated, filtered and dried under vacuum at 40° C. 230 mg of 1,1-diethyl-3-[3-(5-fluoro-6-perhydro-1,4-oxazepin-4-yl-1H-benzimidazol-2-yl)-1H-pyrazol-4-yl]urea are obtained in the form of a pale yellow solid. $^1$H NMR (500 MHz, DMSO-d6, δ in ppm): 1.23 (t, J=7.0 Hz, 6H); 1.96 (m, 2H); 3.35 (m masked, 4H); 3.39 (q partially masked, J=7.0 Hz, 4H); 3.79 (m, 4H); from 6.98 to 7.39 (broad m, 2H); 7.98 (s, 1H); 9.87 (broad s, 1H).

Example 12

N-{3-[5-fluoro-6-(4-methylpiperazin-1-yl)-1H-benzimidazol-2-yl]-1H-pyrazol-4-yl}piperidine-1-carboxamide Trifluoroacetate

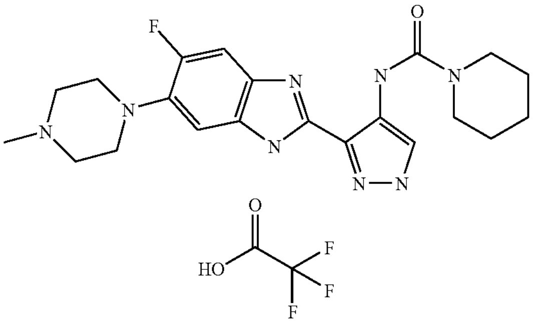

Stage I 4-fluoro-5-(4-methylpiperazin-1-yl)-2-nitrophenylamine

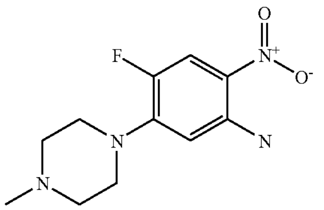 [SMILES: CN1CCN(c2cc(N)c([N+](=O)[O-])cc2F)CC1]

36.2 g of sodium bicarbonate and 28.7 mL of N-methylhomopiperazine are added to a solution of 15 g of 4,5-difluoro-2-nitroaniline in 120 mL of anhydrous DMF. The reaction medium is heated to 80° C. using an oil bath for 2H30. The reaction medium is cooled to ambient temperature, then poured into 500 mL of water. The mixture is cooled using an ice bath and stirred, and precipitation occurs. The precipitate is filtered through sintered glass. The yellow solid is rinsed with water. The solid is dried in an oven at 40° C. 21.2 g of 4-fluoro-5-(4-methylpiperazin-1-yl)-2-nitrophenylamine are obtained in the form of a yellow solid. $^{1}H$ NMR (300 MHz, DMSO-d6, δ in ppm): 2.22 (s, 3H); 2.45 (m, 4H); 3.17 (m, 4H); 6.42 (d, J=8.0 Hz, 1H); 7.34 (broad s, 2H); 7.63 (d, J=14.5 Hz, 1H). EI mass spectrum: m/z=254: M+. (base peak)—m/z=239: $(M-CH_3)+$—m/z=234: (M−HF)+.−m/z=183: $(M-C_4H_9N)+$—m/z=70: $C_4H_8N+$—m/z=43: $C_2H_5N+$.

Stage II 4-fluoro-5-(4-methylpiperazin-1-yl)benzene-1,2-diamine

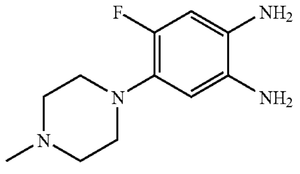 [SMILES: CN1CCN(c2cc(N)c(N)cc2F)CC1]

21.2 g of 4-fluoro-5-(4-methylpiperazin-1-yl)-2-nitrophenylamine in solution in 800 mL of methanol are hydrogenated under 1 bar of hydrogen pressure in the presence of 2.1 g of palladium-on-charcoal at 25° C. for 16 hours. The reaction crude is filtered through celite and the filtrate is concentrated under vacuum in a rotary evaporator. 18.7 g of 4-fluoro-5-(4-methylpiperazin-1-yl)benzene-1,2-diamine in the form of a black oil are isolated. $^{1}H$ NMR (400 MHz, DMSO-d6, δ in ppm), for this batch, all the signals are broad with: 2.19 (s, 3H); 2.40 (m, 4H); 2.79 (m, 4H); 4.22 (s, 2H); 4.31 (s, 2H); from 6.24 to 6.33 (m, 2H). EI mass spectrum: m/z=224: M+. (base peak)—m/z=209: $(M—CH_3)+$—m/z=153: $(M-C_4H_9N)+$—m/z=70: $C_4H_8N+$—m/z=43: $C_2H_5N+$.

Stage III 5-fluoro-6-(4-methylpiperazin-1-yl)-2-([4-nitro-1-(tetrahydropyran-2-yl)-1H-pyrazol-3-yl]-1H-benzimidazol

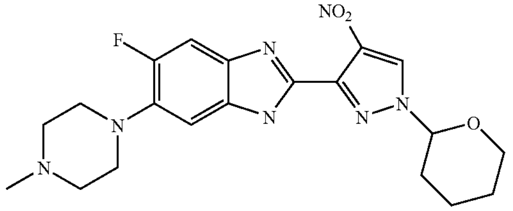 [SMILES: CN1CCN(c2cc3[nH]c(-c4nn(C5CCCCO5)cc4[N+](=O)[O-])nc3cc2F)CC1]

25.4 g of 4-nitro-1-(tetrahydropyran-2-yl)-1H-pyrazole-3-carbaldehyde are added to a solution of 25.3 g of 4-fluoro-5-(4-methylpiperazin-1-yl)benzene-1,2-diamine in 320 mL of methanol. The reaction medium is stirred at 22° C. for 16 hours. After evaporation, the reaction crude is purified on a column 8 cm in diameter, with 3.5 kg of silica having a porosity of 0.063-0.2 mm. The elution is carried out with 2 L of pure dichloromethane and then 5 L of dichloromethane containing 5% of methanol, and then with dichloromethane containing 10% of methanol. 18.1 g of 5-fluoro-6-(4-methylpiperazin-1-yl)-2-[4-nitro-1-(tetrahydropyran-2-yl)-1H-pyrazol-3-yl]-1H-benzimidazoleare isolated. $^{1}H$ NMR (400 MHz, DMSO-d6, δ in ppm): from 1.36 to 2.29 (m, 6H); 2.92 (s, 3H); 3.10 (m, 2H); 3.31 (m, 2H); 3.58 (m, 4H); 3.72 (m, 1H); 4.00 (m, 1H); 5.68 (dd, J=2.0 and 10.0 Hz, 1H); 7.48 (d, J=7.5 Hz, 1H); 7.75 (d, J=11.5 Hz, 1H); 9.38 (s, 1H). ES mass spectrum: m/z=857: (2M−H) base peak—m/z=428: (M−H)−

Stage IV 3-(5-fluoro-6-morpholin-4-yl-1H-benzimidazol-2-yl)-1-(tetrahydropyran-2-yl)-1H-pyrazol-4-ylamine (Intermediate 5)

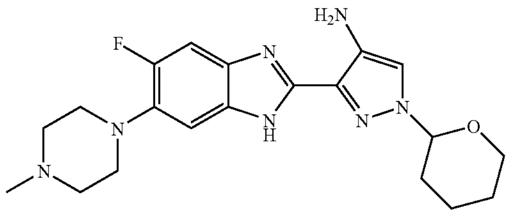 [SMILES: CN1CCN(c2cc3[nH]c(-c4nn(C5CCCCO5)cc4N)nc3cc2F)CC1]

A suspension of 18.1 g of 5-fluoro-6-(4-methylpiperazin-1-yl)-2-[4-nitro-1-(tetrahydropyran-2-yl)-1H-pyrazol-3-yl)-1H-benzimidazolein 425 mL of methanol and 1.8 g of palladium-on-charcoal is hydrogenated under 1 bar of hydrogen pressure at ambient temperature for 18 hours. The reaction medium is filtered through celite and the filtrate is concentrated under reduced pressure in a rotary evaporator. 15.9 g of 3-(5-fluoro-6-morpholin-4-yl-1H-benzimidazol-2-yl)-1-

(tetrahydropyran-2-yl)-1H-pyrazol-4-ylamine are obtained in the form of a brown powder. The compound will be used as it is for the subsequent stage. $^1$H NMR (300 MHz, DMSO-d6, δ in ppm): from 1.48 to 2.24 (m, 6H); 2.91 (s, 3H); 3.05 (m, 2H); 3.28 (m, 2H); 3.54 (m, 4H); 3.67 (m, 1H); 3.97 (m, 1H); 5.55 (dd, J=2.0 and 10.5 Hz, 1H); 7.22 (d, J=8.0 Hz, 1H); 7.48 (d, J=12.0 Hz, 1H); 8.18 (s, 1H). EI mass spectrum: m/z=399: M+. (base peak)—m/z=315: $(M-C_5H_8O)+$—m/z=85: $C_5H_9O+$—m/z=43: $C_2H_5N+$.

Stage V

N-{3-[5-fluoro-6-(4-methylpiperazin-1-yl)-1H-benzimidazol-2-yl]-1-(tetrahydropyran-2-yl)-1H-pyrazol-4-yl}piperidine-1-carboxamide

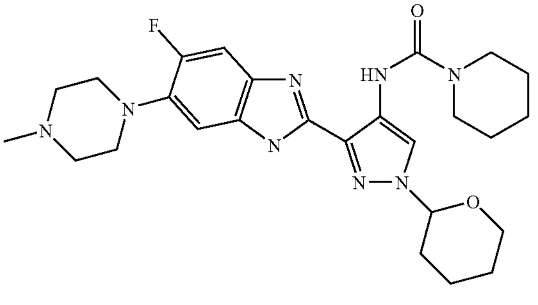 [SMILES: CN1CCN(c2cc3[nH]c(-c4nn(C5CCCCO5)cc4NC(=O)N4CCCCC4)nc3cc2F)CC1]

12.5 mL of 1-piperidinecarbonyl chloride and 17.4 mL of N,N-diisopropylethylamine are added to a solution of 8 g of intermediate 5 in 268 mL of THF. The reaction mixture is heated at 66° C. for 5 hours and then stirred for 16 hours at 22° C. The reaction medium is washed with 115 mL of water. The aqueous phase is extracted with 3 times 215 mL of EtOAc. The organic phases are dried over $MgSO_4$, filtered and concentrated under vacuum in a rotary evaporator. The reaction crude is purified by flash chromatography (elution dichloromethane/-methanol): 8.22 g of piperidine-1-carboxylic acid [3-[5-fluoro-6-(4-methylpiperazin-1-yl)-1H-benzimidazol-2-yl]-1-(tetrahydropyran-2-yl)-1H-pyrazol-4-yl] amide are obtained in the form of a pale yellow powder. It is the TFA salt of the expected structure insofar as we observe: $^1$H NMR (400 MHz, DMSO-d6, δ in ppm): from 1.40 to 2.26 (m, 12H); 2.89 (s, 3H); 3.09 (m, 2H); 3.28 (m, 2H); 3.42 (m, 4H); 3.55 (m, 4H); 3.67 (m, 1H); 3.96 (m, 1H); 5.50 (dd, J=2.5 and 10.5 Hz, 1H); 7.33 (d, J=7.5 Hz, 1H); 7.57 (d, J=11.5 Hz, 1H); 8.15 (s, 1H). EI mass spectrum: m/z=510 (M+); m/z=425 $(M—C_5H_{11}N)+$; m/z=341 $(m/z=425—C_5H_8O)+$. m/z=85 $C_5H_9O+$.; m/z=84 $(C_5H_{10}N+)$; m/z=43 $(C_2H_5N)+$.; m/z=41 $C_3H_5+$ base peak.

Stage VI

N-{3-[5-fluoro-6-(4-methylpiperazin-1-yl)-1H-benzimidazol-2-yl]-1H-pyrazol-4-yl}piperidine-1-carboxamide trifluoroacetate

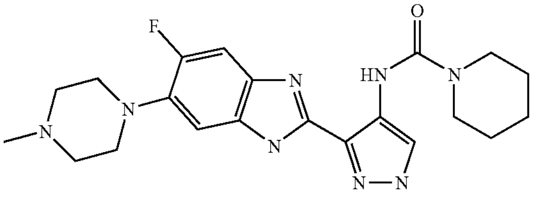

-continued

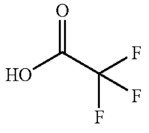

0.6 mL of trifluoroacetic acid is added to a solution of 260 mg of piperidine-1-carboxylic acid [3-[5-fluoro-6-(4-methylpiperazin-1-yl)-1H-benzimidazol-2-yl]-1-(tetrahydropyran-2-yl)-1H-pyrazol-4-yl]amide in solution in 1.5 mL of dichloromethane. The reaction medium is stirred at 22° C. for 48 hours. The reaction medium is concentrated under vacuum in a rotary evaporator. After evaporation, the reaction crude is purified by flash chromatography in an Intelliflash apparatus on an Analogix RS-12 cartridge. The elution is carried out in pure dichloromethane for 20 min and then in dichloromethane containing 10% of ammoniacal methanol. 120 mg of N-{3-[5-fluoro-6-(4-methylpiperazin-1-yl)-1H-benzimidazol-2-yl]-1H-pyrazol-4-yl}piperidine-1-carboxamide are obtained in the form of a beige solid. $^1$H NMR (400 MHz, DMSO-d6, δ in ppm): from 1.45 to 1.70 (m, 6H); 2.90 (s, 3H); 3.07 (m, 2H); 3.29 (m, 2H); 3.45 (m, 4H); 3.55 (m, 4H); 7.31 (d, J=8.0 Hz, 1H); 7.57 (d, J=11.5 Hz, 1H); 8.02 (s, 1H). EI mass spectrum: m/z=426, M+., m/z=341 $(M-C_5H_{11}N)+$; m/z=114 $CF_3CO_2H+$. relative to TFA; m/z=84 $C_5H_{10}N+$; m/z=69 $CF_3+$ relative to TFA; m/z=45 $CO_2H+$ relative to TFA base peak, m/z=43 $C_2H_5N+$.; m/z=41 $C_3H_5+$ Example 13

1,1-diethyl-3-{3-[5-fluoro-6-(4-methylpiperazin-1-yl)-1H-benzimidazol-2-yl]-1H-pyrazol-4-yl}urea Stage V 1,1-diethyl-3-[3-[5-fluoro-6-(4-methylpiperazin-1-yl)-1H-benzimidazol-2-yl]-1-(tetrahydropyran-2-yl)-1H-pyrazol-4-yl]urea

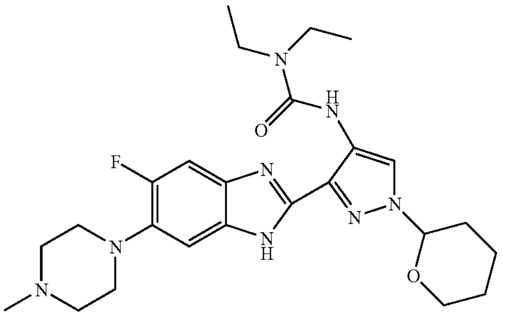 [SMILES: CCN(CC)C(=O)Nc1cn(C2CCCCO2)nc1-c1nc2cc(F)c(N3CCN(C)CC3)cc2[nH]1]

506 μL of diethylcarbamoyl chloride and 662 μL of N,N-diisopropylethylamine are added to a solution of 166 mg of intermediate 5 in 10 mL of THF. The reaction mixture is heated at 55° C. for 40 hours, and then for 2 hours at 80° C. The reaction medium is cooled to ambient temperature and concentrated under vacuum in a rotary evaporator. The reaction crude is purified by flash chromatography (elution dichloromethane/methanol): 250 mg of 1,1-diethyl-3-[3-[5-fluoro-6-(4-methylpiperazin-1-yl)-1H-benzimidazol-2-yl]-1-(tetrahydropyran-2-yl)-1H-pyrazol-4-yl]urea are obtained in the form of a yellow oil. $^1$H NMR (300 MHz, DMSO-d6, δ in ppm): 1.18 (t, J=7.0 Hz, 6H); from 1.50 to 2.21 (m, 6H); 2.90 (s, 3H); 3.05 (m, 2H); 3.28 (m, 2H); 3.38 (q, J=7.0 Hz, 4H); 3.54 (m, 4H); 3.68 (m, 1H); 3.98 (m, 1H); 5.48 (dd, J=2.0 and 10.0 Hz, 1H); 7.23 (d, J=8.0 Hz, 1H); 7.46 (d, J=11.5 Hz, 1H); 8.14 (s. 1H). ES mass spectrum: m/z=497 (M−H) (base peak).

Stage VI 1,1-diethyl-3-{3-[5-fluoro-6-(4-methylpiperazin-1-yl)-1H-benzimidazol-2-yl]-1H-pyrazol-4-yl}urea Trifluoroacetate

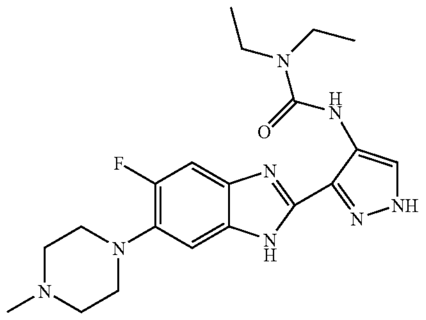 [SMILES: CCN(CC)C(=O)Nc1c[nH]nc1-c1nc2cc(F)c(N3CCN(C)CC3)cc2[nH]1]

0.7 mL of trifluoroacetic acid is added to a solution of 250 mg of 1,1-diethyl-3-[3-[5-fluoro-6-(4-methylpiperazin-1-yl)-1H-benzimidazol-2-yl]-1-(tetrahydro-pyran-2-yl)-1H-pyrazol-4-yl]urea in solution in 2 mL of dichloromethane. The reaction medium is stirred at 22° C. for 72 hours. The reaction medium is concentrated under vacuum in a rotary evaporator. After evaporation, the reaction crude is purified by flash chromatography on an Intelliflash apparatus on an Analogix RS-12 cartridge. The elution is carried out in pure dichloromethane for 15 min and then in dichloromethane containing 10% of ammoniacal methanol. 100 mg of 1,1-diethyl-3-{3-[5-fluoro-6-(4-methylpiperazin-1-yl)-1H-benzimidazol-2-yl]-1H-pyrazol-4-yl}urea are obtained in the form of a beige solid. $^1$H NMR (300 MHz, DMSO-d6, δ in ppm): 1.18 (t, J=7.0 Hz, 6H); 2.90 (s, 3H); 3.05 (m, 2H); 3.28 (m, 2H); 3.38 (q, J=7.0 Hz, 4H); 3.54 (m, 4H); 7.24 (d, J=8.0 Hz, 1H); 7.46 (d, J=11.5 Hz, 1H); 8.00 (s, 1H). EI mass spectrum: m/z=414 (M)+.; m/z=341 $(M-C_4H_{11}N)+$; m/z=114 $CF_3CO_2H+$. relative to TFA; m/z=72 $C_4H_{10}N+$; m/z=69 $CF_3+$ relative to TFA; m/z=45 $CO_2H+$ relative to TFA, base peak; m/z=43 $C_2H_5N+$.

Example 14

1-{2-[4-(3,3-diethylureido)-1H-pyrazol-3-yl]-6-fluoro-3H-benzimidazol-5-yl}-1-(2-dimethylaminoethyl)-3,3-diethylurea Trifluoroacetate

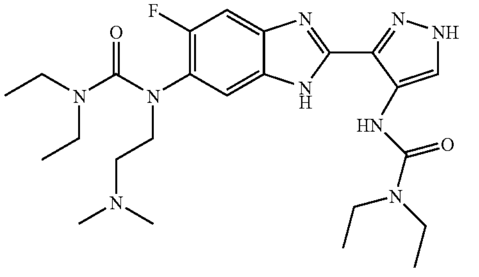

-continued

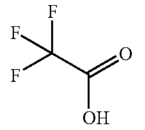

In the same manner as for step V1 of example 15 (see below), 100 mg of 1-{2-[4-(3,3-diethylureido)-1-(tetrahydropyran-2-yl)-1H-pyrazol-3-yl]-6-fluoro-3H-benzimidazol-5-yl}-1-(2-dimethylaminoethyl)-3,3-diethylurea (stage 5, example 15) are deprotected, and 54 mg of 1-{2-[4-(3,3-diethylureido)-1H-pyrazol-3-yl]-6-fluoro-3H-benzimidazol-5-yl}-1-(2-dimethylaminoethyl)-3,3-diethylurea are isolated in the form of a trifluoroacetate salt. $^1$H NMR (300 MHz, DMSO-d6, δ in ppm), for this batch, we observe a 60%-40% resolution of tautomers with: 0.75 (m, 6H); 1.22 (m, 6H); from 2.30 to 2.86 (broad m partially masked, 8H); 3.02 (q, J=7.0 Hz, 4H); 3.42 (q, J=7.0 Hz, 4H); 3.64 (broad m, 2H); 7.36 (m, 1H); 7.52 (m, 1H); 8.02 (s, 1H); 9.35 (broad m, 1H); 9.71 (s, 0.4H); 9.74 (s, 0.6H); 13.1 (broad s, 1H); 13.15 (broad s, 0.4H); 13.2 (broad s, 0.6H). ES mass spectrum: 502(+)=(M+H)(+)

Example 15

3-{3-[6-(2-dimethylaminoethylamino)-5-fluoro-1H-benzimidazol-2-yl]-1H-pyrazol-4-yl}-1,1-diethylurea Trifluoroacetate

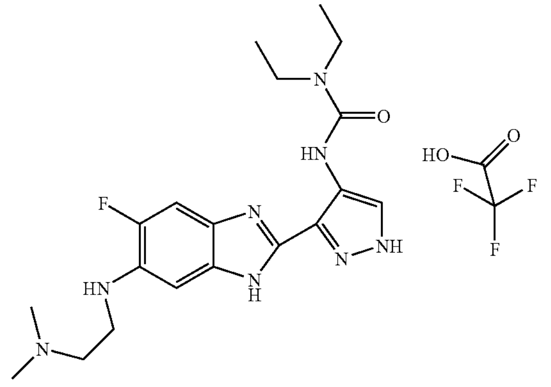 [SMILES: CCN(CC)C(=O)Nc1c[nH]nc1-c1nc2cc(F)c(NCCN(C)C)cc2[nH]1 ; O=C(O)C(F)(F)F]

Stage I

N3-(2-dimethylaminoethyl)-4-fluoro-6-nitrobenzene-1,3-diamine

A solution of 4,5-difluoro-2-nitroaniline in 10 mL of DMF is stirred at ambient temperature and 2.53 g of sodium bicarbonate and 1.67 g of N,N-dimethylenediamine are added. The reaction medium is refluxed for two hours. 30 mL of water are added and the aqueous phase is then extracted with 4×15 mL of ethyl acetate. The organic phases are dried over magnesium sulfate, filtered and concentrated under vacuum in a rotary evaporator. The reaction crude is taken up in isopropyl ether and the solid is triturated, and then filtered through sintered glass. The solid is dried under vacuum at 40° C. until the weight is constant. 1.23 g of N3-(2-dimethylaminoethyl)-4-fluoro-6-nitrobenzene-1,3-diamine are recovered in the form of a yellow solid. $^1$H NMR (300 MHz, DMSO-d6, δ in ppm): 2.19 (s, 6H); 2.45 (t, J=6.5 Hz, 2H); 3.19 (m, 2H); 6.03 (d, J=8.0 Hz, 1H); 6.58 (broad t, J=5.5 Hz, 1H); 7.37 (broad s, 2H); 7.58 (d, J=13.0 Hz, 1H).

Stage II

N4-(2-dimethylaminoethyl)-5-fluorobenzene-1,2,4-triamine 1.29 g of N3-(2-dimethylaminoethyl)-4-fluoro-6-nitrobenzene-1,3-diamine in solution in 30 mL of methanol are hydrogenated under 1 bar of hydrogen pressure in the presence of 130 mg of palladium-on-charcoal at 25° C. for 16 hours. The reaction crude is filtered through celite and the filtrate is concentrated under vacuum in a rotary evaporator. 1 g of N4-(2-dimethylaminoethyl)-5-fluorobenzene-1,2,4-triamine are recovered in the form of a black resin. The product is used as it is for the subsequent stage.

Stage III

N1-{6-fluoro-2-[4-nitro-1-(tetrahydropyran-2-yl)-1H-pyrazol-3-yl]-3H-benzimidazol-5-yl}-N2,N2-dimethylethane-1,2-diamine A solution of 1 g of N4-(2-dimethylaminoethyl)-5-fluorobenzene-1,2,4-triamine in 30 mL of methanol with 1.06 g of 4-nitro-1-(tetrahydropyran-2-yl)-1H-pyrazole-3-carbaldehyde is stirred at ambient temperature for 72 hours. After evaporation of the solvent under vacuum in a rotary evaporator, the reaction crude is purified by flash chromatography on an Intelliflash apparatus on an Analogix RS-90 cartridge with an eluent of 100% dichloromethane to 85/15 dichloromethane/methanol. 350 mg of N1-{6-fluoro-2-[4-nitro-1-(tetrahydropyran-2-yl)-1H-pyrazol-3-yl]-3H-benzimidazol-5-yl}-N2,N2-dimethylethane-1,2-diamine are isolated in the form of an orange foam. ES mass spectrum: 418(+)=(M+H)(+); 334(+)=(M+H)(+)-THP+H, 209.6=(M+2H)(2+)

Stage IV

N1-{2-[4-amino-1-(tetrahydropyran-2-yl)-1H-pyrazol-3-yl]-6-fluoro-3H-benzimidazol-5-yl}-N2,N2-dimethylethane-1,2-diamine 350 mg of N1-{6-fluoro-2-[4-nitro-1-(tetrahydropyran-2-yl)-1H-pyrazol-3-yl]-3H-benzimidazol-5-yl}-N2,N2-dimethylethane-1,2-diamine in 15 mL of methanol and 40 mg of palladium-on-charcoal are hydrogenated under 1 bar of hydrogen pressure at 22° C. for 16 hours. The reaction medium is filtered through celite and the filtrate is concentrated under reduced pressure in a rotary evaporator. 300 mg of N1-{2-[4-amino-1-(tetrahydropyran-2-yl)-1H-pyrazol-3-yl]-6-fluoro-3H-benzimidazol-5-yl}-N2,N2-dimethylethane-1,2-diamine are obtained. The compound is used as it is for the subsequent stage.

Stage V

3-[3-[6-(2-dimethylaminoethylamino)-5-fluoro-1H-benzimidazol-2-yl]-1-(tetrahydropyran-2-yl)-1H-pyrazol-4-yl]-1,1-diethylurea

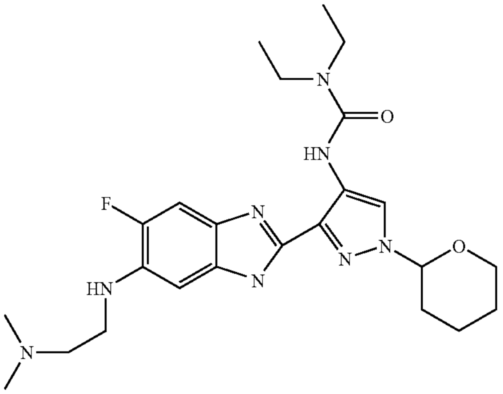 [SMILES: CCN(CC)C(=O)Nc1cn(C2CCCCO2)nc1-c1nc2cc(F)c(NCCN(C)C)cc2[nH]1]

A solution of 132 mg of N1-{2-[4-amino-1-(tetrahydropyran-2-yl)-1H-pyrazol-3-yl]-6-fluoro-3H-benzimidazol-5-yl}-N2,N2-dimethylethane-1,2-diamine in 8 mL of tetrahydrofuran with 428 μL of diethylcarbamoyl chloride and 560 μL of N,N-diisopropylethylamine is heated at 55° C. for 48 hours. 15 mL of water are added and then the aqueous phase is extracted with 3×15 mL of ethyl acetate. The organic phases are washed with 2×15 mL of distilled water, dried over magnesium sulfate, filtered and concentrated under vacuum in a rotary evaporator. The reaction crude is purified by flash chromatography on an Intelliflash apparatus on an Analogix RS-12 cartridge, with a 95/5 dichloromethane/-methanol eluent. 18 mg of 3-[3-[6-(2-dimethylaminoethylamino)-5-fluoro-1H-benzimidazol-2-yl]-1-(tetrahydropyran-2-yl)-1H-pyrazol-4-yl]-1,1-diethylurea are isolated in the form of a yellow resin. $^1$H NMR (400 MHz, DMSO-d6, δ in ppm), after addition of a drop of TFA-d1 (trifluoroacetic acid $CF_3COOD$-d1) and of a drop of acetic acid-d4-($CD_3OD$-d4): 1.16 (t, J=7.5 Hz, 6H); 1.56 (m, 2H); 1.70 (m, 1H); 1.97 (m, 2H); 2.14 (m, 1H); 2.86 (s, 6H); 3.37 (m, 6H); 3.50 (t, J=6.5 Hz, 2H); 3.68 (m, 1H); 3.96 (m, 1H); 5.48 (broad d, J=10.0 Hz, 1H); 6.88 (d, J=7.5 Hz, 1H); 7.42 (d, J=11.0 Hz, 1H); 8.11 (s, 1H).

100 mg of 1-{2-[4-(3,3-diethylureido)-1-(tetrahydro-pyran-2-yl)-1H-pyrazol-3-yl]-6-fluoro-3H-benzimidazol-5-yl}-1-(2-dimethylaminoethyl)-3,3-diethylurea

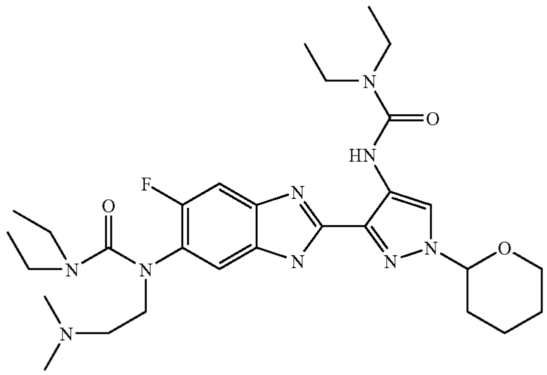 [SMILES: CCN(CC)C(=O)Nc1cn(C2CCCCO2)nc1-c1nc2cc(F)c(N(CCN(C)C)C(=O)N(CC)CC)cc2[nH]1]

are also recovered, this compound being used for example 14. $^1$H NMR (400 MHz, DMSO-d6, δ in ppm), after addition of a drop of TFA-d1 ($CF_3COOD$-d1) and of a drop of acetic acid-d4-($CD_3OD$-d4): 0.73 (t, J=7.0 Hz, 6H); 1.21 (t, J=7.0 Hz, 6H); 1.56 (m, 2H); 1.70 (m, 1H); 1.97 (m, 2H); 2.14 (m, 1H); 2.83 (s, 6H); 3.04 (q, J=7.0 Hz, 4H); 3.21 (t, J=6.5 Hz, 2H); 3.40 (q, J=7.0 Hz, 4H); 3.66 (m, 1H); 3.78 (t, J=6.5 Hz, 2H); 3.95 (m, 1H); 5.47 (dd, J=2.0 and 10.0 Hz, 1H); 7.49 (d, J=10.5 Hz, 1H); 7.51 (d, J=7.0 Hz, 1H); 8.16 (s, 1H).

Stage VI

3-{3-[6-(2-dimethylaminoethylamino)-5-fluoro-1H-benzimidazol-2-yl]-1H-pyrazol-4-yl}-1,1-diethylurea A solution of 18 mg of 3-[3-[6-(2-dimethylaminoethylamino)-5-fluoro-1H-benzimidazol-2-yl]-1-(tetrahydro-pyran-2-yl)-1H-pyrazol-4-yl]-1,1-diethylurea in 1 mL of dichloromethane and 500 μL of trifluoroacetic acid are stirred for 72 hours at ambient temperature. After evaporation of the solvent under vacuum in a rotary evaporator, the reaction crude is purified by flash chromatography on an Analogix RS-4 cartridge with an eluent of 100% dichloromethane to 90/10 dichloromethane/ammoniacal methanol. 10 mg of 3-{3-[6-(2-dimethylaminoethylamino)-5-fluoro-1H-benzimidazol-2-yl]-1H-pyrazol-4-yl}-1,1-diethylurea in the form of trifluoroacetate are isolated. $^1$H NMR (300 MHz, DMSO-d6, δ in ppm), after addition of a drop of TFA-d1 ($CF_3COOD$-d1) and of a drop of acetic acid-d4-($CD_3OD$-d4): 1.16 (t, J=7.0 Hz, 6H); 2.87 (s, 6H); 3.38 (m, 6H); 3.51 (t, J=6.0 Hz, 2H); 6.89 (d, J=7.5 Hz, 1H); 7.44 (d, J=11.0 Hz, 1H); 7.98 (s, 1H).

Example 16

3-[3-(5-fluoro-6-morpholin-4-yl-1H-benzimidazol-2-yl)-1H-pyrazol-4-yl]-1,1-diisopropylurea in the Form of a Trifluoroacetate Salt

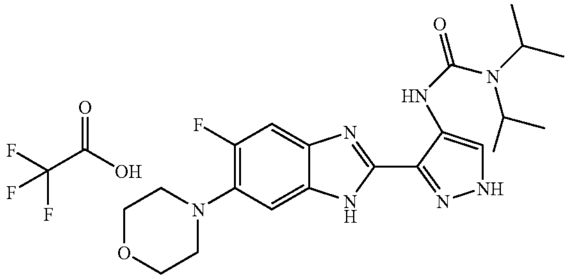

Stage V

3-[3-(5-fluoro-6-morpholin-4-yl-1H-benzimidazol-2-yl)-1-(tetrahydropyran-2-yl)-1H-pyrazol-4-yl]-1,1-diisopropylurea A solution of 300 mg of gamma intermediate in 33 mL of tetrahydrofuran is stirred at ambient temperature, and then 676 μL of N,N-diisopropylethylamine and 127 mg of diisopropylcarbamoyl chloride are added. The solution is refluxed. Diisopropylcarbamoyl chloride is added until the reaction is complete. The reaction medium is treated with 20 mL of a saturated solution of sodium chloride and then the aqueous phase is extracted with 3×30 mL of ethyl acetate. The organic phases are dried over magnesium sulfate and concentrated under vacuum in a rotary evaporator. 550 mg of 3-[3-(5-fluoro-6-morpholin-4-yl-1H-benzimidazol-2-yl)-1-(tetrahydro-pyran-2-yl)-1H-pyrazol-4-yl]-1,1-diisopropylurea are isolated in the form of a brown solid. LC/MS: Tr=4.53 min, $[M+H]^+$=514.24, UV254 nm=59%.

Stage VI

3-[3-(5-fluoro-6-morpholin-4-yl-1H-benzimidazol-2-yl)-1H-pyrazol-4-yl]-1,1-diisopropylurea in the Form of a Trifluoroacetate Salt A solution of 550 mg of 3-[3-(5-fluoro-6-morpholin-4-yl-1H-benzimidazol-2-yl)-1-(tetrahydropyran-2-yl)-1H-pyrazol-4-yl]-1,1-diisopropylurea in 8.5 mL of concentrated hydrochloric acid is stirred at ambient temperature for 12 hours and the medium is concentrated under vacuum in a rotary evaporator. The reaction crude is purified by preparative LC/MS, elution being carried out with a mixture of water and acetonitrile containing respectively 0.07% of trifluoroacetic acid. 183 mg of 3-[3-(5-fluoro-6-morpholin-4-yl-1H-benzimidazol-2-yl)-1H-pyrazol-4-yl]-1,1-diisopropylurea in the form of a trifluoroacetate salt are isolated. $^1$H NMR (400 MHz, DMSO-d6, δ in ppm): 1.35 (d, J=7.0 Hz, 12H); 3.00 (m, 4H); 3.78 (m, 4H); 4.07 (m, 2H); 7.08 (broad d, J=7.5 Hz, 1H); 7.32 (broad d, J=12.0 Hz, 1H); 8.03 (s, 1H); 9.57 (s, 1H); 12.95 (broad m, 2H).

Example 17

N-{3-[5-fluoro-6-(4-methylperhydro-1,4-diazepin-1-yl)-1H-benzimidazol-2-yl]-1H-pyrazol-4-yl}-piperidine-1-carboxamide Trifluoroacetate

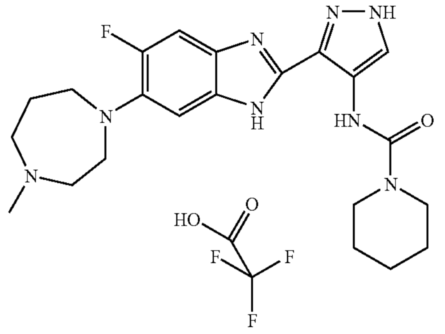 [SMILES: CN1CCCN(c2cc3[nH]c(-c4n[nH]cc4NC(=O)N4CCCCC4)nc3cc2F)CC1 ; O=C(O)C(F)(F)F]

Stage I 4-fluoro-5-(4-methylperhydro-1,4-diazepin-1-yl)-2-nitrophenylamine

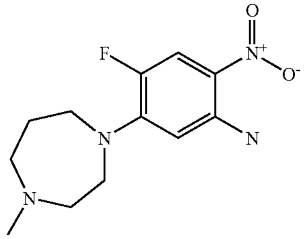 [SMILES: CN1CCCN(c2cc(N)c([N+](=O)[O-])cc2F)CC1]

36.2 g of sodium bicarbonate and 29.5 g of N-methylhomopiperazine are added to a solution of 15 g of 4,5-difluoro-2-nitroaniline in 120 mL of anhydrous DMF. The reaction medium is heated at 80° C. using an oil bath for 2H30. The reaction medium is cooled to ambient temperature, and then poured into 400 mL of water. The mixture is cooled using an ice bath and stirred, and precipitation occurs. The precipitate is filtered off through sintered glass. The yellow solid is rinsed with water. The solid is dried in an oven at 40° C. 21 g of 4-fluoro-5-(4-methylperhydro-1,4-diazepin-1-yl)-2-nitrophenylamine are obtained in the form of a yellow solid. $^{1}H$ NMR (300 MHz, DMSO-d6, δ in ppm): 1.90 (m, 2H); 2.27 (s, 3H); 2.50 (m masked, 2H); 2.64 (m, 2H); 3.46 (m, 2H); 3.52 (m, 2H); 6.21 (d, J=9.0 Hz, 1H); 7.24 (broad s, 2H); 7.59 (d, J=16.0 Hz, 1H). EI mass spectrum: m/z=268: M+. (base peak)—m/z=253: $(M-CH_3)+$—m/z=198: $(M-C_4H_8N)+$—m/z=70: $C_4H_8N+$—m/z=57: $C_3H_7N+$.

Stage II 4-fluoro-5-(4-methylperhydro-1,4-diazepin-1-yl)benzene-1,2-diamine

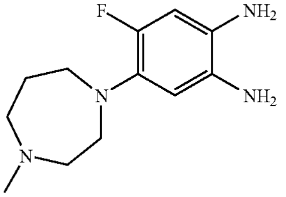 [SMILES: CN1CCCN(c2cc(N)c(N)cc2F)CC1]

20.9 g of 4-fluoro-5-(4-methylperhydro-1,4-diazepin-1-yl)-2-nitrophenylamine in solution in 750 mL of methanol are hydrogenated under 1 bar of hydrogen pressure in the presence of 2 g of palladium-on-charcoal at 25° C. for 16 hours. The reaction crude is filtered through celite and the filtrate is concentrated under vacuum in a rotary evaporator. 19.1 g of 4-fluoro-5-(4-methylperhydro-1,4-diazepin-1-yl)benzene-1,2-diamine in the form of a black oil are isolated. $^{1}H$ NMR (300 MHz, DMSO-d6, δ in ppm): 1.82 (m, 2H); 2.26 (s, 3H); 2.56 (m, 4H); 3.11 (m, 4H); 4.19 (broad m, 4H); from 6.22 to 6.31 (m, 2H). EI m/z=238: M+. (base peak)—m/z=223: $(M-CH_3)+$—m/z=168: $(M-C_4H_8N)+$—m/z=70: $C_4H_8N+$—m/z=57: $C_3H_7N+$.

Stage III 5-fluoro-6-(4-methylperhydro-1,4-diazepin-1-yl)-2-[4-nitro-1-(tetrahydropyran-2-yl)-1H-pyrazol-3-yl]-1H-benzimidazole

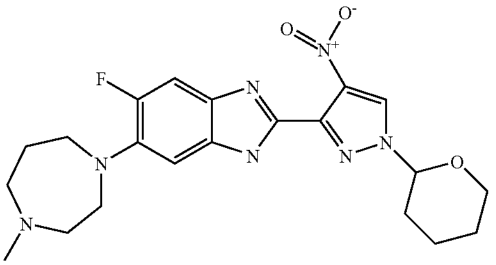 [SMILES: CN1CCCN(c2cc3[nH]c(-c4nn(C5CCCCO5)cc4[N+](=O)[O-])nc3cc2F)CC1]

18 g of 4-nitro-1-(tetrahydropyran-2-yl)-1H-pyrazole-3-carbaldehyde and 664 mg of ferric chloride are added to a solution of 19.1 g of 4-fluoro-5-(4-methylperhydro-1,4-diazepin-1-yl)benzene-1,2-diamine in 406 mL of DMF. The reaction medium is stirred at 22° C. for 4 hours. After evaporation, the reaction crude is purified on a column 8 cm in diameter, with 3 kg of silica having a porosity of 0.063-0.2 mm. The elution is carried out with 2 L of pure dichloromethane and then 4 L of dichloromethane containing 10% of methanol, and then with dichloromethane containing 15% of methanol. 12 g of 5-fluoro-6-(4-methylperhydro-1,4-diazepin-1-yl)-2-[4-nitro-1-(tetrahydropyran-2-yl)-1H-pyrazol-3-yl]-1H-benzimidazole are isolated. $^{1}H$ NMR (400 MHz, DMSO-d6, δ in ppm): 1.41 to 2.31 (m, 8H); 2.91 (s, 3H); from 3.22 to 3.67 (m, 8H); 3.72 (m, 1H); 3.99 (m, 1H); 5.69 (dd, J=2.5 and 9.5 Hz, 1H); 7.32 (d, J=8.0 Hz, 1H); 7.75 (d, J=12.0 Hz, 1H); 9.40 (s, 1H). EI mass spectrum: m/z=443: M+. —m/z=373: $(M-C_4H_8N)+$—m/z=289: $(m/z=373—C_5H_8O)+$—m/z=84: $C_5H_8O+$. (base peak)—m/z=57: $C_3H_7N+$.

Stage IV

3-[5-fluoro-6-(4-methylperhydro-1,4-diazepin-1-yl)-1H-benzimidazol-2-yl]-1-(tetrahydropyran-2-yl)-1H-pyrazol-4-ylamine (Intermediate 4)

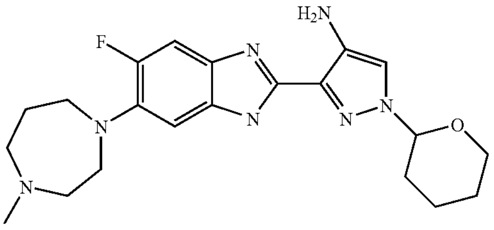 [SMILES: CN1CCCN(c2cc3[nH]c(-c4nn(C5CCCCO5)cc4N)nc3cc2F)CC1]

A suspension of 11.9 g of 5-fluoro-6-(4-methylperhydro-1,4-diazepin-1-yl)-2-[4-nitro-1-(tetrahydropyran-2-yl)-1H-pyrazol-3-yl]-1H-benzimidazole in 260 mL of methanol and 1.2 g of palladium-on-charcoal is hydrogenated under 1 bar of hydrogen pressure at ambient temperature for 18 hours. The reaction medium is filtered through celite and the filtrate is concentrated under reduced pressure in a rotary evaporator. 10.9 g of 3-[5-fluoro-6-(4-methylperhydro-1,4-diazepin-1-yl)-1H-benzimidazol-2-yl]-1-(tetrahydropyran-2-yl)-1H-pyrazol-4-ylamine are obtained in the form of a brown powder. $^{1}H$ NMR (300 MHz, DMSO-d6, δ in ppm): 1.43 to 2.17 (m, 8H); 2.33 (s, 3H); 2.64 (m, 2H); 2.73 (m, 2H); from 3.20 to 3.40 (m masked, 4H); 3.62 (m, 1H); 3.95 (m, 1H); 4.92 (broad s, 2H); 5.31 (dd, J=2.5 and 10.0 Hz, 1H); from 6.91 to 7.36 (m, 2H); 7.31 (s, 1H); 12.4 (broad m, 1H). ES mass spectrum: m/z=414: MH+ (base peak)—m/z=330: $(MH-C_5H_8O)+$ Stage V N-[3-[5-fluoro-6-(4-methylperhydro-1,4-diazepin-1-yl)-1H-benzimidazol-2-yl]-1-(tetrahydro-pyran-2-yl)-1H-pyrazol-4-yl]piperidine 1-carboxamide

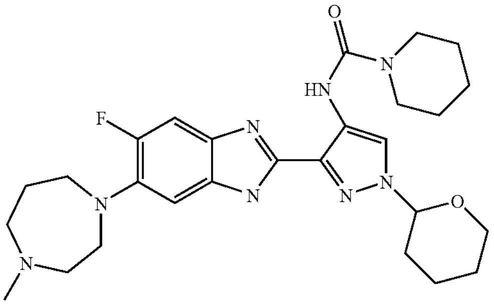 [SMILES: CN1CCCN(c2cc3[nH]c(-c4nn(C5CCCCO5)cc4NC(=O)N4CCCCC4)nc3cc2F)CC1]

12.1 mL of 1-piperidinecarbonyl chloride and 16.8 mL of N,N-diisopropylethylamine are added to a solution of 8 g of intermediate 4 in 260 mL of THF. The reaction mixture is heated at 66° C. for 5 hours. The reaction medium is cooled to ambient temperature and 100 mL of water are added. The aqueous phase is extracted with 3 times 250 mL of EtOAc. The organic phases are dried over $MgSO_4$, filtered and concentrated under vacuum in a rotary evaporator. The reaction crude is purified by flash chromatography, elution being carried out with a mixture of dichloromethane/methanol: 5.6 g of piperidine-1-carboxylic acid [3-[5-fluoro-6-(4-methylperhydro-1,4-diazepin-1-yl)-1H-benzimidazol-2-yl]-1-(tetrahydropyran-2-yl)-1H-pyrazol-4-yl]amide are obtained in the form of a yellow resin. $^{1}$H NMR (400 MHz, DMSO-d6, δ in ppm): 1.43 to 2.17 (m, 14H); 2.30 (s, 3H); 2.60 (m, 2H); 2.70 (m, 2H); 3.30 (m masked, 4H); 3.49 (m, 4H); 3.66 (m, 1H); 3.93 (m, 1H); 5.46 (dd, J=2.5 and 10.0 Hz, 1H); from 6.92 to 7.42 (broad m, 2H); 8.12 (s, 1H); 9.96 (s, 1H); 12.85 (broad m, 1H). ES mass spectrum: m/z=525: MH+—m/z=441: $(MH–C_5H_8O)$+—m/z=85: $C_5H_9O$+ (base peak).

Stage VI

N-{3-[5-fluoro-6-(4-methylperhydro-1,4-diazepin-1-yl)-1H-benzimidazol-2-yl]-1H-pyrazol-4-yl}-piperidine-1-carboxamide Trifluoroacetate

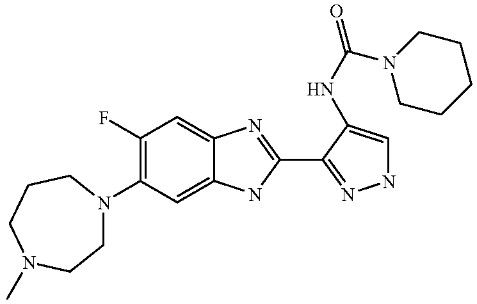 [SMILES: CN1CCCN(c2cc3[nH]c(-c4n[nH]cc4NC(=O)N4CCCCC4)nc3cc2F)CC1]

0.5 mL of trifluoroacetic acid is added to a solution of 60 mg of N-[3-[5-fluoro-6-(4-methylperhydro-1,4-diazepin-1-yl)-1H-benzimidazol-2-yl]-1-(tetrahydro-pyran-2-yl)-1H-pyrazol-4-yl]piperidine-1-carboxamide in solution in 1 mL of dichloromethane. The reaction medium is stirred at 22° C. for 16 hours. The reaction medium is concentrated under vacuum in a rotary evaporator. After evaporation, the reaction crude is purified by flash chromatography. The elution is carried out with pure dichloromethane and then with a mixture of dichloromethane containing 5% of ammoniacal methanol. 29 mg of N-{3-[5-fluoro-6-(4-methylperhydro-1,4-diazepin-1-yl)-1H-benzimidazol-2-yl]-1H-pyrazol-4-yl}piperidine-1-carboxamide are obtained in the form of a yellow solid. $^{1}$H NMR (400 MHz, DMSO-d6, δ in ppm): 1.42 to 2.27 (m, 8H); 2.90 (s, 3H); from 3.18 to 3.65 (m, 12H); 7.20 (d, J=7.0 Hz, 1H); 7.56 (d, J=12.0 Hz, 1H); 8.00 (s, 1H). ES mass spectrum: m/z=439 (M–H)—base peak.

Example 18

1,1-diethyl-3-{3-[5-fluoro-6-(4-methylperhydro-1,4-diazepin-1-yl)-1H-benzimidazol-2-yl]-1H-pyrazol-4-yl}urea (2 Stages Starting from Intermediate 4)

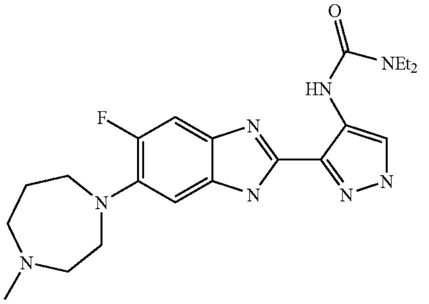

$CF_3COOH$

Stage V 1,1-diethyl-3-[3-[5-fluoro-6-(4-methylperhydro-1,4-diazepin-1-yl)-1H-benzimidazol-2-yl]-1-(tetrahydro-pyran-2-yl)-1H-pyrazol-4-yl]urea

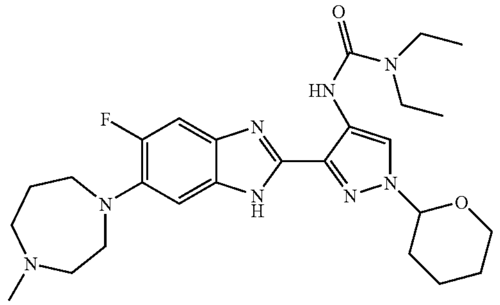 [SMILES: CCN(CC)C(=O)Nc1cn(C2CCCCO2)nc1-c1nc2cc(F)c(N3CCCN(C)CC3)cc2[nH]1]

362 μL of diethylcarbamoyl chloride and 500 μL of N,N-diisopropylethylamine are added to a solution of 118 mg of intermediate 4 in 7 mL of THF. The reaction mixture is heated at 55° C. for 16 hours and then at 80° C. for 2 hours. The reaction medium is cooled to ambient temperature and 20 mL of distilled water are added. The aqueous phase is extracted with 3 times 10 mL of EtOAc. The organic phases are dried over $MgSO_4$, filtered and concentrated under vacuum in a rotary evaporator. The reaction crude is purified by flash chromatography, elution being carried out with a mixture of dichloromethane/methanol. 39 mg of 1,1-diethyl-3-[3-[5-fluoro-6-(4-methylperhydro-1,4-diazepin-1-yl)-1H-benzimidazol-2-yl]-1-(tetrahydropyran-2-yl)-1H-pyrazol-4-yl]urea are obtained in the form of a yellow resin. $^{1}$H NMR (400 MHz, DMSO-d6, δ in ppm): 1.12 (t, J=7.0 Hz, 6H); from 1.50 to 2.26 (m, 8H); 2.90 (s, 3H); from 3.18 to 3.63 (m, 8H); 3.34 (q, J=7.0 Hz, 4H); 3.68 (m, 1H); 3.96 (m, 1H); 5.49 (dd, J=2.5 and 10.0 Hz, 1H); 7.19 (d, J=7.5 Hz, 1H); 7.52 (d, J=12.0 Hz, 1H); 8.12 (s, 1H). ES mass spectrum: m/z=513: MH+—m/z=429 $(MH–C_5H_8O)$+(base peak)—m/z=356: (m/z=429—$C_4H_{11}N$)+—m/z=85: $C_5H_9O$+.

Stage VI 1,1-diethyl-3-{3-[5-fluoro-6-(4-methylperhydro-1,4-diazepin-1-yl)-1H-benzimidazol-2-yl]-1H-pyrazol-4-yl}urea in the Form of a Trifluoroacetate Salt 0.5 mL of trifluoroacetic acid is added to a solution of 39 mg of 1,1-diethyl-3-[3-[5-fluoro-6-(4-methylperhydro-1,4-diazepin-1-yl)-1H-benzimidazol-2-yl]-1-(tetrahydropyran-2-yl)-1H-pyrazol-4-yl}urea in solution in 1 mL of dichloromethane. The reaction medium is stirred at 22° C. for 16 hours. The reaction medium is concentrated under vacuum in a rotary evaporator. After evaporation, the reaction crude is purified by flash chromatography on an Intelliflash apparatus on an Analogix RS-4 cartridge. The elution is carried out with pure dichloromethane and then with dichloromethane containing 5% of ammoniacal methanol. 12 mg of 1,1-diethyl-3-{3-[5-fluoro-6-(4-methylperhydro-1,4-diazepin-1-yl)-1H-benzimidazol-2-yl]-1H-pyrazol-4-yl}urea trifluoroacetate salt are obtained in the form of a black resin. $^{1}$H NMR (300 MHz, DMSO-d6, δ in ppm): 1.10 (t, J=7.0 Hz, 6H); 2.20 (broad m, 2H); 2.89 (s, 3H); from 3.07 to 3.68 (m, 8H); 3.34 (q, J=7.0 Hz, 4H); 7.22 (d, J=7.5 Hz, 1H); 7.55 (d, J=12.0 Hz, 1H); 7.96 (s, 1H). EI mass spectrum: m/z=428 M+., m/z=355

$(M-C_4H_{11}N)+$, m/z=69 $CF_3+$ (relative to TFA), m/z=58 $C_3H_8N+$ (base peak), m/z=45 $CO_2H+$ (relative to TFA).

Example 19

1,1-diethyl-3-{3-[6-(4-methylpiperazin-1-yl)-1H-benzimidazol-2-yl]-1H-pyrazol-4-yl}urea

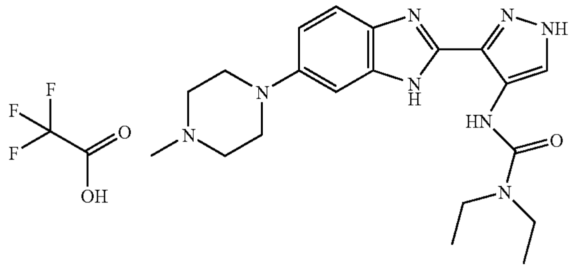

Stage I 6-(4-methylpiperazin-1-yl)-2-[4-nitro-1-(tetrahydro-pyran-2-yl)-1H-pyrazol-3-yl]-1H-benzimidazole

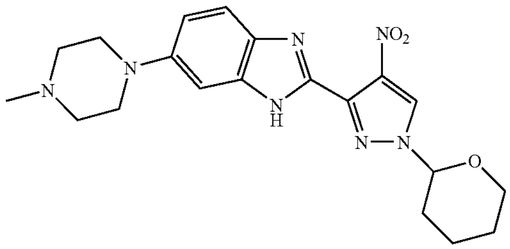 [SMILES: CN1CCN(c2ccc3nc(-c4nn(C5CCCCO5)cc4[N+](=O)[O-])[nH]c3c2)CC1]

742 mg of 4-nitro-1-(tetrahydropyran-2-yl)-1H-pyrazole-3-carbaldehyde are added to a solution of 680 mg of 4-(4-methylpiperazino)-1,2-benzenediamine in 30 mL of methanol. The reaction medium is stirred at 22° C. for 3 hours. The reaction medium is heated at 60° C. using an oil bath for 1H30, and then stirred at 22° C. for 64 hours. After evaporation, the reaction crude is purified by flash chromatography on an Intelliflash apparatus on an Analogix RS-12 cartridge. The elution is carried out in dichloromethane containing 10% methanol. 370 mg of 6-(4-methylpiperazin-1-yl)-2-[4-nitro-1-(tetrahydropyran-2-yl)-1H-pyrazol-3-yl]-1H-benzimidazole are isolated. Analytical LC/MS: tr=1.88 min; $[M+H]^+$ =412.32; ELSD=97%; DAD=93%. $^1H$ NMR (400 MHz, DMSO-d6, δ in ppm): 1.50 to 2.23 (m, 6H); 2.25 (s, 3H); 2.50 (m masked, 4H); 3.14 (m, 4H); 3.70 (m, 1H); 4.00 (m, 1H); 5.59 (broad d, J=9.5 Hz, 1H); from 6.90 to 7.15 (m, 2H); from 7.39 to 7.54 (m, 1H); 9.17 (s, 1H); from 12.5 to 12.7 (m, 1H).

Stage II

Preparation of 3-[6-(4-methylpiperazin-1-yl)-1H-benzimidazol-2-yl]-1-(tetrahydropyran-2-yl)-1H-pyrazol-4-ylamine (Intermediate 3)

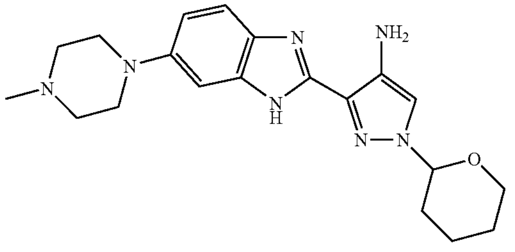

A suspension of 370 mg of 6-(4-methylpiperazin-1-yl)-2-[4-nitro-1-(tetrahydropyran-2-yl)-1H-pyrazol-3-yl]-1H-benzimidazole in 10 mL of methanol and 37 mg of palladium-on-charcoal is hydrogenated under 1 bar of hydrogen pressure at ambient temperature for 18 hours. The reaction medium is filtered through celite and the filtrate is concentrated under reduced pressure in a rotary evaporator. 360 mg of 3-[6-(4-methylpiperazin-1-yl)-1H-benzimidazol-2-yl]-1-(tetrahydropyran-2-yl)-1H-pyrazol-4-ylamine are obtained in the form of a black oil. $^1H$ NMR (300 MHz, DMSO-d6, δ in ppm): 1.50 to 2.21 (m, 6H); 2.23 (s, 3H); 2.50 (m masked, 4H); 3.08 (m, 4H); 3.61 (m, 1H); 3.94 (m, 1H); from 4.89 to 4.98 (m, 2H); 5.30 (broad d, J=10.0 Hz, 1H); from 6.85 to 7.12 (m, 2H); from 7.25 to 7.46 (m, 2H); from 12.2 to 12.35 (m, 1H).

Procedure A for Preparing the Urea Derivatives of the Type Described Below

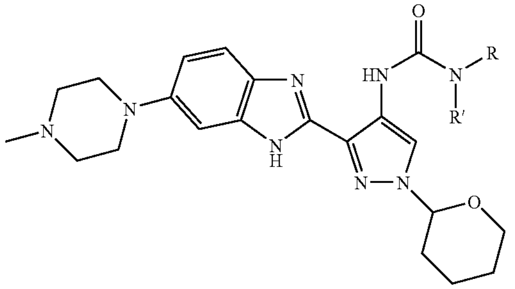

5 eq of carbamoyl chloride and 5 eq of N,N-diisopropylethylamine are added to a solution of 180 mg of intermediate 3 in 10 mL of THF. The reaction mixture is heated at 52° C. for 48 hours in a Radley tube. The reaction medium is cooled to ambient temperature and mL of a saturated solution of sodium bicarbonate are added. The aqueous phase is extracted with 3 times 10 mL of EtOAc. The organic phases are dried over $MgSO_4$, filtered and concentrated under vacuum in a rotary evaporator. The concentrate is used immediately in the subsequent stage.

Stage III

Preparation of 1,1-diethyl-3-[3-[6-(4-methylpiperazin-1-yl)-1H-benzimidazol-2-yl]-1-(tetrahydropyran-2-yl)-1H-pyrazol-4-yl]urea According to procedure A, in the presence of diethylcarbamoyl chloride, 210 mg of 1-diethyl-3-[3-[6-(4-methylpiperazin-1-yl)-1H-benzimidazol-2-yl]-1-(tetrahydropyran-2-yl)-1H-pyrazol-4-yl]urea are obtained.

Stage IV

Preparation of 1,1-diethyl-3-{3-[6-(4-methylpiperazin-1-yl)-1H-benzimidazol-2-yl]-1H-pyrazol-4-yl}urea 742 μL of trifluoroacetic acid and 100 μL of water are added to a solution of 210 mg of 1-diethyl-3-[3-[6-(4-methylpiperazin-1-yl)-1H-benzimidazol-2-yl]-1-(tetrahydropyran-2-yl)-1H-pyrazol-4-yl]urea in solution in 2.22 mL of dichloromethane. The reaction medium is stirred at 22° C. for 48 hours. The reaction mixture is heated at 50° C. for 10 minutes. After evaporation, the reaction crude is purified by flash chromatography. The elution is carried out in dichloromethane containing 15% of methanol. 80 mg of 1,1-diethyl-3-{3-[6-(4-methylpiperazin-1-yl)-1H-benzimidazol-2-yl]-1H-pyrazol-4-yl}urea are isolated. 61 mg of 1,1-diethyl-3-[3-[6-(4-methylpiperazin-1-yl)-1H-benzimidazol-2-yl]-1-(tetrahydropyran-2-yl)-1H-pyrazol-4-yl}urea are isolated and reacted again with 2.2 mL of TFA and 550 μL of water. The reaction medium is stirred at 22° C. for 120 hours. After evaporation, the reaction crude is purified by flash chromatography on an Intelliflash apparatus on an Analogix RS-4 cartridge. The elution is carried out in dichloromethane containing 15% of methanol. 17 mg of 1,1-diethyl-3-{3-[6-(4-methylpiperazin-1-yl)-1H-benzimidazol-2-yl]-1H-pyrazol-4-yl}-urea are isolated. That is to say, 92 mg of 1,1-diethyl-3-{3-[6-(4-methylpiperazin-1-yl)-1H-benzimidazol-2-yl]-1H-pyrazol-4-yl}urea are isolated in total.

$^1$H NMR (400 MHz, DMSO-d6, δ in ppm): 1.16 (t, J=7.0 Hz, 6H); 2.93 (s, 3H); 3.11 (m, 2H); 3.26 (m, 2H); 3.39 (q, J=7.0 Hz, 4H); 3.60 (m, 2H); 3.89 (m, 2H); 7.20 (d, J=1.5 Hz, 1H); 7.31 (dd, J=1.5 and 9.0 Hz, 1H); 7.66 (d, J=9.0 Hz, 1H); 7.89 (s, 1H).

Example 20

N-{3-[6-(4-methylpiperazin-1-yl)-1H-benzimidazol-2-yl]-1H-pyrazol-4-yl}piperidine-1-carboxamide (In 2 Stages Starting from Intermediate 3)

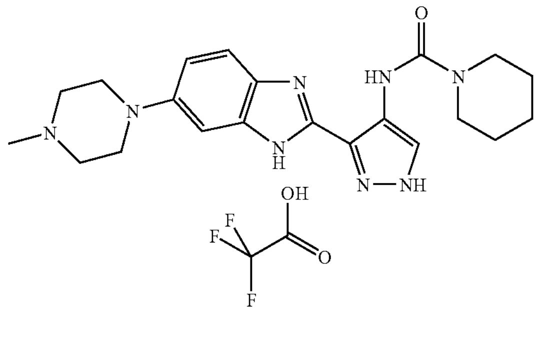

Stage III

Preparation of N-[3-[6-(4-methylpiperazin-1-yl)-1H-benzimidazol-2-yl]-1-(tetrahydropyran-1-yl)-1H-pyrazol-4-yl]piperidine-1-carboxamide According to procedure A, in the presence of piperidine-1-carbonyl chloride, 290 mg of N-[3-[6-(4-methylpiperazin-1-yl)-1H-benzimidazol-2-yl]-1-(tetrahydropyran-2-yl)-1H-pyrazol-4-yl]piperidine-1-carboxamide are obtained.

Stage IV

Preparation of N-{3-[6-(4-methylpiperazin-1-yl)-1H-benzimidazol-2-yl]-1H-pyrazol-4-yl}piperidine-1-carboxamide 1 mL of trifluoroacetic acid and 100 μL of water are added to a solution of 290 mg of N-[3-[6-(4-methylpiperazin-1-yl)-1H-benzimidazol-2-yl]-1-(tetrahydropyran-2-yl)-1H-pyrazol-4-yl]piperidine-1-carboxamide in solution in 3 mL of dichloromethane. The reaction medium is stirred at 22° C. for 24 hours. The reaction medium is concentrated under vacuum in a rotary evaporator. 0.5 mL of dichloromethane, 0.5 mL of trifluoroacetic acid and 100 μL of water are added. The reaction medium is stirred at 22° C. for 4 hours. After evaporation, the reaction crude is purified by flash chromatography on an Intelliflash apparatus on an Analogix RS-12 cartridge. The elution is carried out in dichloromethane containing 15% of methanol. 40 mg of N-{3-[6-(4-methylpiperazin-1-yl)-1H-benzimidazol-2-yl]-1H-pyrazol-4-yl}piperidine-1-carboxamide are isolated. 123 mg of N-[3-[6-(4-methylpiperazin-1-yl)-1H-benzimidazol-2-yl]-1-(tetrahydropyran-2-yl)-1H-pyrazol-4-yl]piperidine-1-carboxamide are isolated and reacted again with 2.8 mL of TFA and 700 μL of water. The reaction medium is stirred at 22° C. for 72 hours. After evaporation, the reaction crude is purified by flash chromatography on an Intelliflash apparatus on an Analogix RS-12 cartridge. The elution is carried out in dichloromethane containing 15% of methanol. 37 mg of N-{3-[6-(4-methylpiperazin-1-yl)-1H-benzimidazol-2-yl]-1H-pyrazol-4-yl}piperidine-1-carboxamide are isolated. That is to say, 77 mg of N-{3-[6-(4-methylpiperazin-1-yl)-1H-benzimidazol-2-yl]-1H-pyrazol-4-yl}piperidine-1-carboxamide are isolated in total. $^1$H NMR (400 MHz, DMSO-d6, δ in ppm): 1.43 to 1.63 (m, 6H); 2.90 (s, 3H); 3.05 (m, 2H); 3.22 (m, 2H); 3.43 (m, 4H); 3.58 (m, 2H); 3.89 (m, 2H); 7.17 (broad s, 1H); 7.31 (broad d, J=9.0 Hz, 1H); 7.65 (d, J=9.0 Hz, 1H); 8.02 (s, 1H).

Example 21

N-[3-(5-fluoro-6-piperazin-1-yl-1H-benzimidazol-2-yl)-1H-pyrazol-4-yl]piperidine-1-carboxamide

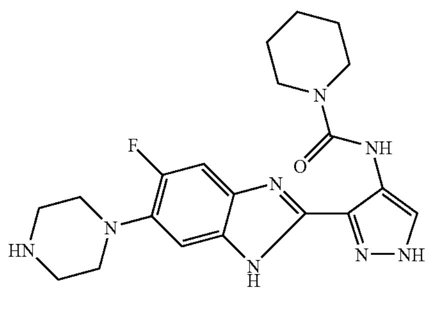 [SMILES: O=C(Nc1c[nH]nc1-c1nc2cc(F)c(N3CCNCC3)cc2[nH]1)N1CCCCC1]

Stage I 4-(5-amino-2-fluoro-4-nitrophenyl)piperazine-1-carboxylic Acid Tert-Butyl Ester

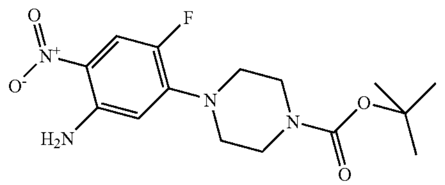 [SMILES: CC(C)(C)OC(=O)N1CCN(c2cc(N)c([N+](=O)[O-])cc2F)CC1]

2.4 g of potassium bicarbonate and 1 g of 4,5-difluoro-2-nitroaniline are added to a solution of 3.3 g of piperazine-1-carboxylic acid tert-butyl ester in 30 mL of anhydrous DMF. The reaction medium is heated at 60° C. using an oil bath for 30 minutes. The reaction medium is cooled to ambient temperature, then 150 mL of water are added thereto, and precipitation occurs. The precipitate is filtered off through sintered glass. The solid is dried in an oven at 50° C. 1.4 g of 4-(5-amino-2-fluoro-4-nitrophenyl)piperazine-1-carboxylic acid tert-butyl ester are obtained in the form of a yellow solid. $^1$H NMR (300 MHz, DMSO-d6, δ in ppm): 1.42 (s, 9H); 3.14 (m, 4H); 3.46 (m, 4H); 6.43 (d, J=8.0 Hz, 1H); 7.36 (broad s, 2H); 7.66 (d, J=14.5 Hz, 1H). EI mass spectrum: m/z=340 M+., m/z=284 (M−$C_4$H+., m/z=264 (m/z=284−HF)+, m/z=57 $C_4$H+ (base peak).

Stage II 4-(4,5-diamino-2-fluorophenyl)piperazine-1-carboxylic Acid Tert-Butyl Ester

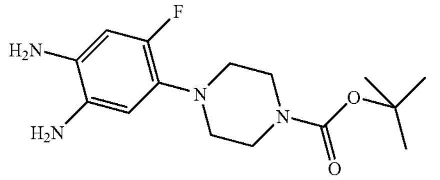 [SMILES: CC(C)(C)OC(=O)N1CCN(c2cc(N)c(N)cc2F)CC1]

1.4 g of 4-(5-amino-2-fluoro-4-nitrophenyl)piperazine-1-carboxylic acid tert-butyl ester in solution in 20 mL of methanol are hydrogenated under 1 bar of hydrogen pressure in the presence of 139 mg of palladium-on-charcoal at 22° C. for 16 hours. The reaction crude is filtered through celite and the filtrate is concentrated under vacuum in a rotary evaporator. 1.4 g of 4-(4,5-diamino-2-fluorophenyl)piperazine-1-carboxylic acid tert-butyl ester are isolated in the form of a brown resin. $^1$H NMR (300 MHz, DMSO-d6, δ in ppm): 1.41 (s, 9H); 2.73 (m, 4H); 3.40 (m, 4H); 4.23 (broad s, 2H); 4.37 (broad s, 2H); 6.27 (d, J=8.5 Hz, 1H); 6.31 (d, J=13.5 Hz, 1H). EI mass spectrum: m/z=310 M+. (base peak), m/z=254 (M-$C_4$H)+, m/z=57 $C_4$H+.

Stage III

4-{6-fluoro-2-[4-nitro-1-(tetrahydropyran-2-yl)-1H-pyrazol-3-yl]-3H-benzimidazol-5-yl}piperazine-1-carboxylic Acid Tert-Butyl Ester

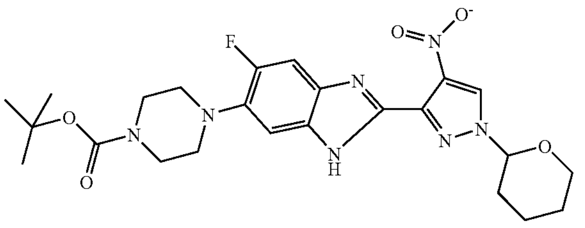

0.9 g of 4-nitro-1-(tetrahydropyran-2-yl)-1H-pyrazole-3-carbaldehyde is added to a solution of 1.2 g of 4-(4,5-diamino-2-fluorophenyl)piperazine-1-carboxylic acid tert-butyl ester in 30 mL of methanol. The reaction medium is stirred at 22° C. for 16 hours. After evaporation, the reaction crude is purified by flash chromatography, elution being carried out with a mixture of dichloromethane/acetone. 530 mg of 4-{6-fluoro-2-[4-nitro-1-(tetrahydropyran-2-yl)-1H-pyrazol-3-yl]-3H-benzimidazol-5-yl}piperazine-1-carboxylic acid tert-butyl ester are isolated in the form of a red foam. $^1$H NMR (400 MHz, DMSO-d6, δ in ppm): from 1.35 to 2.25 (m, 6H); 1.43 (s, 9H); 3.03 (m, 4H); 3.52 (m, 4H); 3.72 (m, 1H); 4.00 (m, 1H); 5.65 (dd, J=2.0 and 10.0 Hz, 1H); 7.31 (d, J=8.0 Hz, 1H); 7.54 (d, J=12.0 Hz, 1H); 9.17 (s, 1H). ES mass spectrum: m/z=516 MH+ (base peak).

Stage IV

4-{2-[4-amino-1-(tetrahydropyran-2-yl)-1H-pyrazol-3-yl]-6-fluoro-3H-benzimidazol-5-yl}piperazine-1-carboxylic Acid Tert-Butyl Ester

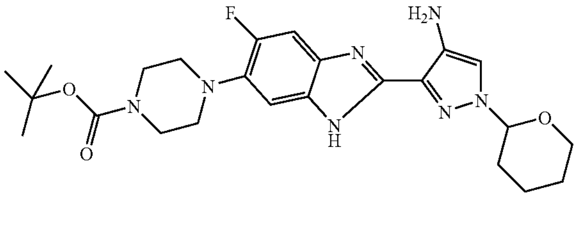 [SMILES: CC(C)(C)OC(=O)N1CCN(c2cc3[nH]c(-c4nn(C5CCCCO5)cc4N)nc3cc2F)CC1]

A suspension of 540 mg of 4-{6-fluoro-2-[4-nitro-1-(tetrahydropyran-2-yl)-1H-pyrazol-3-yl]-3H-benzimidazol-5-yl}piperazine-1-carboxylic acid tert-butyl ester in 15 mL of methanol and 54 mg of palladium-on-charcoal is hydrogenated under 1 bar of hydrogen pressure at ambient temperature for 16 hours. The reaction medium is filtered through celite and the filtrate is concentrated under reduced pressure in a rotary evaporator. 900 mg of 4-{2-[4-amino-1-(tetrahydropyran-2-yl)-1H-pyrazol-3-yl]-6-fluoro-3H-benzimidazol-5-yl}piperazine-1-carboxylic acid tert-butyl ester are obtained in the form of a black solid. $^1$H NMR (400 MHz, DMSO-d6, δ in ppm): from 1.30 to 2.20 (m, 6H); 1.42 (s, 9H); 3.00 (m, 4H); 3.52 (m, 4H); 3.67 (m, 1H); 3.96 (m, 1H); 5.55 (broad d, J=10.0 Hz, 1H); 7.22 (d, J=7.5 Hz, 1H); 7.46 (d, J=12.5 Hz, 1H); 8.17 (s, 1H). ES mass spectrum: m/z=486 MH+ (base peak).

Stage V

4-{6-fluoro-2-[4-[(piperidine-1-carbonyl)amino]-1-(tetrahydropyran-2-yl)-1H-pyrazol-3-yl]-3H-benzimidazol-5-yl}piperazine-1-carboxylic Acid Tert-butyl Ester

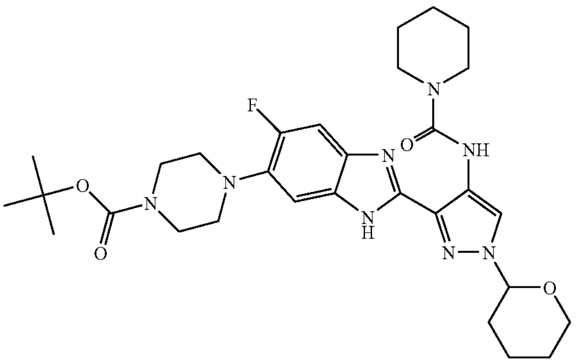 [SMILES: CC(C)(C)OC(=O)N1CCN(c2cc3[nH]c(-c4nn(C5CCCCO5)cc4NC(=O)N4CCCCC4)nc3cc2F)CC1]

1.2 mL of 1-piperidinecarbonyl chloride and 1.7 mL of N,N-diisopropylethylamine are added to a solution of 480 mg of 4-{2-[4-amino-1-(tetrahydropyran-2-yl)-1H-pyrazol-3-yl]-6-fluoro-3H-benzimidazol-5-yl}piperazine-1-carboxylic acid tert-butyl ester in 10 mL of THF. The reaction mixture is heated at 80° C. for 16 hours. The reaction medium is cooled to ambient temperature and 20 mL of a saturated solution of sodium bicarbonate are added. The aqueous phases are extracted with 3 times 10 mL of EtOAc. The organic phases are dried over $MgSO_4$, filtered and concentrated under vacuum in a rotary evaporator. The reaction crude is purified by flash chromatography, elution being carried out with a mixture of cyclohexane/ethyl acetate. 350 mg of 4-{6-fluoro-2-[4-[(piperidine-1-carbonyl)amino]-1-(tetrahydropyran-2-yl)-1H-pyrazol-3-yl]-3H-benzimidazol-5-yl}piperazine-1-carboxylic acid tert-butyl ester are obtained in the form of a brown foam. $^1H$ NMR (400 MHz, DMSO-d6, δ in ppm): from 1.37 to 2.22 (m, 12H); 1.42 (s, 9H); 3.04 (m, 4H); 3.44 (m, 4H); 3.53 (m, 4H); 3.67 (m, 1H); 3.96 (m, 1H); 5.52 (dd, J=2.0 and 10.0 Hz, 1H); 7.29 (d, J=7.5 Hz, 1H); 7.56 (d, J=11.5 Hz, 1H); 8.15 (s, 1H). ES mass spectrum: m/z=597 MH+ (base peak).

Stage VI

N-[3-(5-fluoro-6-piperazin-1-yl-1H-benzimidazol-2-yl)-1H-pyrazol-4-yl]-piperidine-1-carboxamide

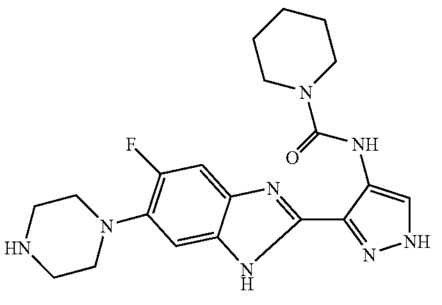 [SMILES: O=C(Nc1c[nH]nc1-c1nc2cc(F)c(N3CCNCC3)cc2[nH]1)N1CCCCC1]

0.5 mL of water is added to a solution of 380 mg of 4-{6-fluoro-2-[4-[(piperidine-1-carbonyl)amino]-1-(tetrahydropyran-2-yl)-1H-pyrazol-3-yl]-3H-benzimidazol-5-yl}piperazine-1-carboxylic acid tert-butyl ester in solution in 2 mL of trifluoroacetic acid. The reaction medium is stirred at 22° C. for 48 hours. The reaction medium is concentrated under vacuum in a rotary evaporator. The reaction crude is purified by flash chromatography on an Intelliflash apparatus on an Analogix RS-40 cartridge. The elution is carried out with pure dichloromethane and then with dichloromethane containing 5% of ammoniacal methanol. 195 mg of N-[3-(5-fluoro-6-piperazin-1-yl-1H-benzimidazol-2-yl)-1H-pyrazol-4-yl]-piperidine-1-carboxamide are obtained in the form of a yellow solid. $^1H$ NMR (400 MHz, DMSO-d6, δ in ppm): from 1.48 to 1.68 (m, 6H); 3.23 (m, 4H); 3.30 (m, 4H); 3.47 (m, 4H); 7.24 (d, J=8.0 Hz, 1H); 7.48 (d, J=11.5 Hz, 1H); 8.01 (s, 1H). ES mass spectrum: m/z=413 MH+, m/z=328 $(M+H—C_5H_{11}N)+$, m/z=227.9 $(M+CH_3CN+2H)2+/2$ (base peak). Remark: the acetonitrile explaining the m/z=227.9 peak is in the mobile phase.

Examples 22 to 30, 33 and 36 are carried out according to scheme 4:

Scheme 4

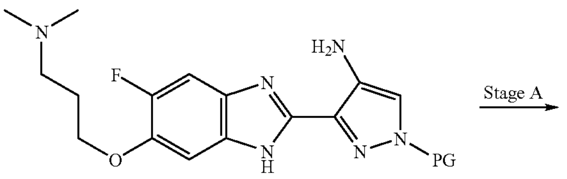

Intermediate 1

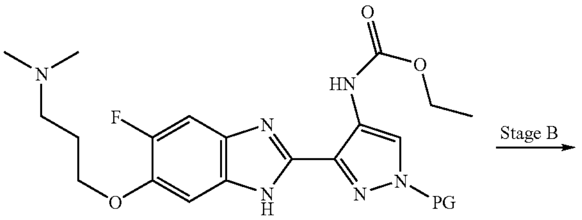

Intermediate 2

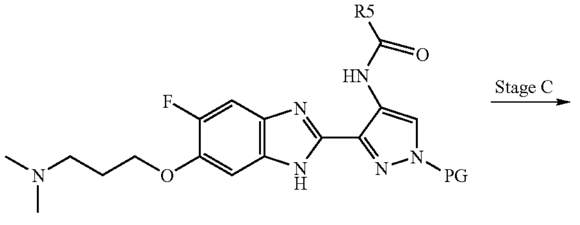

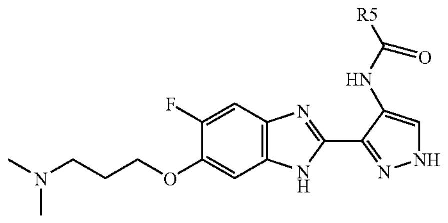

Preferably, the protective group used is the following:

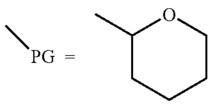

(tetrahydropyran)

Stage A

[3-[6-(3-dimethylaminopropoxy)-5-fluoro-1H-benzimidazol-2-yl]-1-(tetrahydropyran-2-yl)-1H-pyrazol-4-yl]carbamic Acid Ethyl Ester (Intermediate 2)

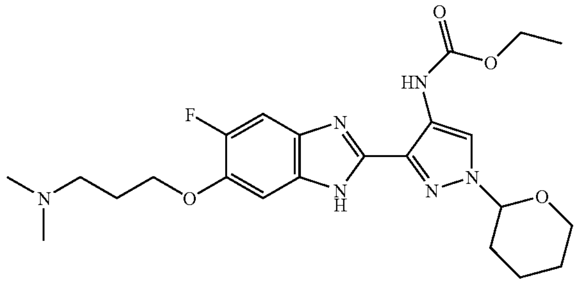 [SMILES: CCOC(=O)Nc1cn(C2CCCCO2)nc1-c1nc2cc(F)c(OCCCN(C)C)cc2[nH]1]

71 μL of ethyl chloroformate and 103.8 μL of triethylamine are added to a solution of 0.3 g of intermediate 1 in 5 mL of dichloromethane. The reaction mixture is stirred at 22° C. for 2.5 hours. The reaction medium is washed with 5 mL of water. The aqueous phase is extracted with 3 times 5 mL of dichloromethane. The organic phases are dried over $MgSO_4$, filtered and concentrated under vacuum in a rotary evaporator. 307 mg of [3-[6-(3-dimethylaminopropoxy)-5-fluoro-1H-benzimidazol-2-yl]-1-(tetrahydropyran-2-yl)-1H-pyrazol-4-yl]carbamic acid ethyl ester are obtained in the form of a brown powder. $^1$H NMR (300 MHz, DMSO-d6, δ in ppm): 1.25 (m, 3H); 1.60 to 2.18 (m, 6H); 2.2 (m, 2H); 2.86 (s, 6H); 3.3 (t, J=8 Hz, 2H); 3.7 (m, 1H); 3.9 (m, 1H); 4.2 (m, 4H); 5.4 (m, 1H); 7.4 (d, J=8 Hz, 1H); 7.61 (d, J=10.0 Hz, 1H); 8.20 (s, 1H).

Stage B General Method 50 eq of amine to be substituted are added to a solution of 30 or 50 mg of intermediate 2 in 1 mL of DMF. The reaction mixture is irradiated for 40 min at 200° C. on a microwave on a Personal Synthesizer. The reaction medium is concentrated under vacuum in a rotary evaporator. The concentrate is used immediately in the subsequent stage.

Stage C General Method

A solution of the concentrate in solution in 40 eq of a 4N solution of hydrochloric acid in dioxane is stirred at 22° C. for approximately 4 hours (until the starting product has disappeared). The reaction medium is concentrated under vacuum in a rotary evaporator. The concentrate is purified by preparative LC/MS with, as eluent, a gradient of water/acetonitrile containing respectively 0.07% of trifluoroacetic acid.

Example 22

Cyclopropyl-3-{3-[6-(3-dimethylaminopropoxy)-5-fluoro-1H-benzimidazol-2-yl]-1H-pyrazol-4-yl}urea

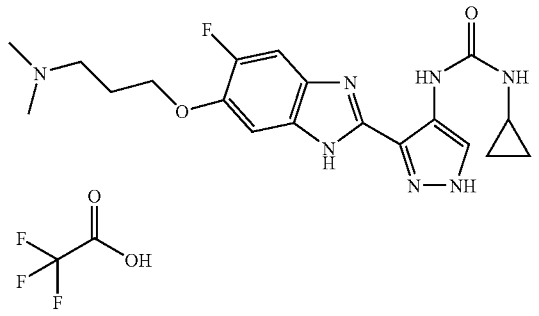 [SMILES: CN(C)CCCOc1cc2[nH]c(-c3n[nH]cc3NC(=O)NC3CC3)nc2cc1F ; O=C(O)C(F)(F)F]

Stage B

Preparation of 1-cyclopropyl-3-[3-[6-(3-dimethylaminopropoxy)-5-fluoro-1H-benzimidazol-2-yl]-1-(tetrahydropyran-2-yl)-1H-pyrazol-4-yl]urea Starting from 30 mg of intermediate 2 and cyclopropylamine according to the general procedure. Analytical LC/MS: Tr=2.46 min; $[M+H]^+$=486.19; ELSD=60%; DAD=56%.

Stage C

1-cyclopropyl-3-{3-[6-(3-dimethylaminopropoxy)-5-fluoro-1H-benzimidazol-2-yl]-1H-pyrazol-4-yl}urea The crude obtained according to the general method is purified by preparative LC/MS with the standard gradient. 13 mg of 1-cyclopropyl-3-{3-[6-(3-dimethylaminopropoxy)-5-fluoro-1H-benzimidazol-2-yl]-1H-pyrazol-4-yl}urea are obtained in the form of a brown powder. $^1$H NMR (400 MHz, DMSO-d6, δ in ppm): 0.32 (m, 2H); 0.53 (m, 2H); 0.78 (m, 1H); 2.18 (m, 2H); 2.85 (s, 6H); 3.27 (m, 2H); 4.17 (t, J=6.0 Hz, 2H); 7.27 (d, J=7.5 Hz, 1H); 7.48 (d, J=10.5 Hz, 1H); 8.05 (s, 1H).

Example 23

N-{3-[6-(3-dimethylaminopropoxy)-5-fluoro-1H-benzimidazol-2-yl]-1H-pyrazol-4-yl}-pyrrolidine-1-carboxamide

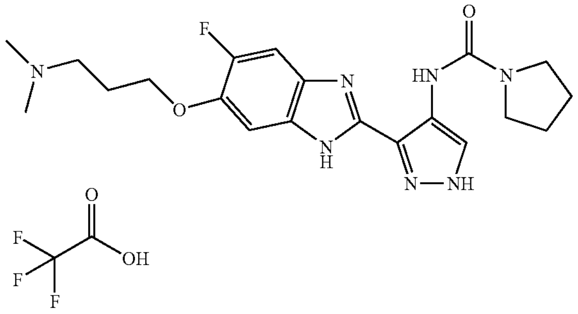 [SMILES: CN(C)CCCOc1cc2[nH]c(-c3n[nH]cc3NC(=O)N3CCCC3)nc2cc1F ; O=C(O)C(F)(F)F]

Stage B

N-[3-[6-(3-dimethylaminopropoxy)-5-fluoro-1H-benzimidazol-2-yl]-1-(tetrahydropyran-2-yl)-1H-pyrazol-4-yl]pyrrolidine-1-carboxamide Starting from 30 mg of intermediate 2 and pyrrolidine according to the general procedure. Analytical LC/MS: Tr=2.53 min; $[M+H]^+$=500.58; ELSD=66%; DAD=71%.

Stage C

Preparation of N-{3-[6-(3-dimethylaminopropoxy)-5-fluoro-1H-benzimidazol-2-yl]-1H-pyrazol-4-yl}pyrrolidine-1-carboxamide The crude obtained according to the general method is purified by preparative LC/MS with the standard gradient. 22.5 mg of N-{3-[6-(3-dimethylaminopropoxy)-5-fluoro-1H-benzimidazol-2-yl]-1H-pyrazol-4-yl}pyrrolidine-1-carboxamide are obtained in the form of a brown powder. $^1H$ NMR (400 MHz, DMSO-d6, δ in ppm): 1.89 (m, 4H); 2.19 (m, 2H); 2.85 (s, 6H); 3.28 (m, 2H); 3.41 (m, 4H); 4.22 (t, J=6.0 Hz, 2H); 7.39 (d, J=7.5 Hz, 1H); 7.63 (d, J=10.5 Hz, 1H); 8.00 (s, 1H).

Example 24

1-{3-[6-(3-Dimethylaminopropoxy)-5-fluoro-1H-benzimidazol-2-yl]-1H-pyrazol-4-yl}-3-isopropylurea

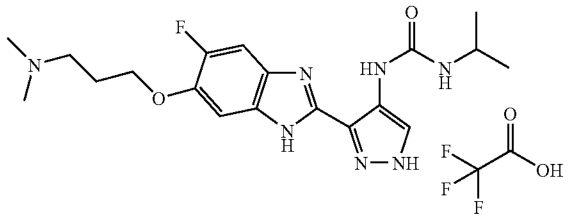

Stage B

Preparation of 1-[3-[6-(3-dimethylaminopropoxy)-5-fluoro-1H-benzimidazol-2-yl]-1-(tetrahydro-pyran-2-yl)-1H-pyrazol-4-yl]-3-isopropylurea Starting from 30 mg of intermediate 2 and diisopropylamine according to the general method. Analytical LC/MS: Tr=2.53 min; $[M+H]^+$=488.35; ELSD=55%; DAD=41%.

Stage C

Preparation of 1-{3-[6-(3-dimethylaminopropoxy)-5-fluoro-1H-benzimidazol-2-yl]-1H-pyrazol-4-yl}-3-isopropylurea The crude obtained according to the general method is purified by preparative LC/MS with the standard gradient. 12.5 mg of 1-{3-[6-(3-dimethylaminopropoxy)-5-fluoro-1H-benzimidazol-2-yl]-1H-pyrazol-4-yl}-3-isopropylurea are obtained in the form of a brown powder. $^1H$ NMR (400 MHz, DMSO-d6, δ in ppm): 1.11 (d, J=6.5 Hz, 6H); 2.18 (m, 2H); 2.85 (s, 6H); 3.28 (m, 2H); 3.78 (m, 1H); 4.18 (t, J=6.0 Hz, 2H); 7.29 (broad d, J=8.0 Hz, 1H); 7.48 (broad d, J=10.5 Hz, 1H); 8.05 (s, 1H).

Example 25

N-{3-[6-(3-Dimethylaminopropoxy)-5-fluoro-1H-benzimidazol-2-yl]-1H-pyrazol-4-yl}morpholine-4-carboxamide

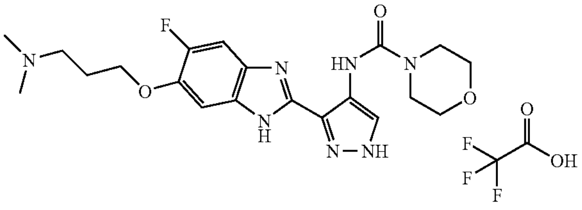

Stage B

Preparation of N-[3-[6-(3-dimethylaminopropoxy)-5-fluoro-1H-benzimidazol-2-yl]-1-(tetrahydro-pyran-2-yl)-1H-pyrazol-4-yl]morpholine-4-carboxamide Starting from 30 mg of intermediate 2 and morpholine according to the general method. Analytical LC/MS: Tr=2.50 min; $[M+H]^+$=516.35; ELSD=90%; DAD=81%.

Stage C

Preparation of N-{3-[6-(3-dimethylaminopropoxy)-5-fluoro-1H-benzimidazol-2-yl]-1H-pyrazol-4-yl}morpholine-4-carboxamide The crude obtained according to the general method is purified by preparative LC/MS with the standard gradient. 25.1 mg of N-{3-[6-(3-dimethylaminopropoxy)-5-fluoro-1H-benzimidazol-2-yl]-1H-pyrazol-4-yl}morpholine-4-carboxamide are obtained in the form of a brown powder. $^1H$ NMR (400 MHz, DMSO-d6, δ in ppm): 2.18 (m, 2H); 2.85 (s, 6H); 3.27 (m, 2H); 3.45 (m, 4H); 3.65 (m, 4H); 4.20 (t, J=6.0 Hz, 2H); 7.34 (d, J=8.0 Hz, 1H); 7.62 (d, J=11.0 Hz, 1H); 8.05 (s, 1H).

Example 26

3-{3-[6-(3-Dimethylaminopropoxy)-5-fluoro-1H-benzimidazol-2-yl]-1H-pyrazol-4-yl}-1-isopropyl-1-methylurea

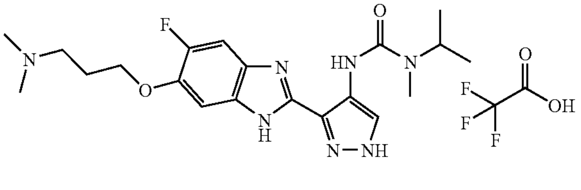

Stage B

Preparation of 3-[3-[6-(3-dimethylaminopropoxy)-5-fluoro-1H-benzimidazol-2-yl]-1-(tetrahydro-pyran-2-yl)-1H-pyrazol-4-yl]-1-isopropyl-1-methylurea Starting from 50 mg of intermediate 2 and N-methyl-N-isopropylamine according to the general method. Analytical LC/MS: Tr=2.70 min; $[M+H]^+$=502.26; ELSD=73%; DAD=43%.

Stage C

Preparation of 3-{3-[6-(3-dimethylaminopropoxy)-5-fluoro-1H-benzimidazol-2-yl]-1H-pyrazol-4-yl}-1-isopropyl-1-methylurea The crude product obtained according to the general method is purified by preparative LC/MS with the standard gradient. 34.3 mg of 3-{3-[6-(3-dimethylaminopropoxy)-5-fluoro-1H-benzimidazol-2-yl]-1H-pyrazol-4-yl}-1-isopropyl-1-methylurea are obtained in the form of a brown powder. $^1$H NMR (400 MHz, DMSO-d6, δ in ppm): 1.11 (d, J=6.5 Hz, 6H); 2.18 (m, 2H); 2.85 (s, 6H); 2.87 (s, 3H); 3.27 (m, 2H); 4.20 (t, J=6.0 Hz, 2H); 4.45 (m, 1H); 7.34 (d, J=8.0 Hz, 1H); 7.57 (d, J=11.0 Hz, 1H); 8.01 (s, 1H).

Example 27

1-tert-Butyl-3-{3-[6-(3-dimethylaminopropoxy)-5-fluoro-1H-benzimidazol-2-yl]-1H-pyrazol-4-yl}urea

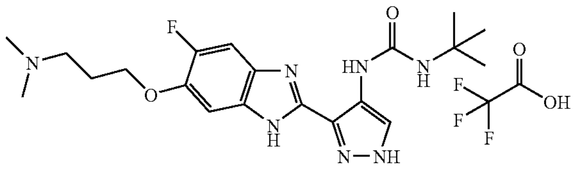

Stage B

Preparation of 1-tert-Butyl-3-[3-[6-(3-dimethylaminopropoxy)-5-fluoro-1H-benzimidazol-2-yl]-1-(tetrahydropyran-2-yl)-1H-pyrazol-4-yl]urea Starting from 50 mg of intermediate 2 and tert-butylamine according to the general method. Analytical LC/MS: Tr=2.85 min; $[M+H]^+$=502.52; ELSD=34%; DAD=31%.

Stage C 1-tert-Butyl-3-{3-[6-(3-dimethylaminopropoxy)-5-fluoro-1H-benzimidazol-2-yl]-1H-pyrazol-4-yl}urea The crude product obtained according to the general method is purified by preparative LC/MS with the standard gradient. 8.9 mg of 1-tert-butyl-3-{3-[6-(3-dimethylaminopropoxy)-5-fluoro-1H-benzimidazol-2-yl]-1H-pyrazol-4-yl}urea are obtained in the form of a brown powder. $^1$H NMR (400 MHz, DMSO-d6, δ in ppm): 1.28 (s, 9H); 2.19 (m, 2H); 2.85 (s, 6H); 3.28 (m, 2H); 4.21 (t, J=6.0 Hz, 2H); 7.38 (d, J=7.0 Hz, 1H); 7.63 (d, J=10.0 Hz, 1H); 8.10 (s, 1H).

Example 28

1-{3-[6-(3-dimethylaminopropoxy)-5-fluoro-1H-benzimidazol-2-yl]-1H-pyrazol-4-yl}-3-isobutylurea

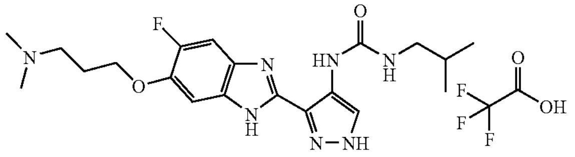

Stage B

Preparation of 1-[3-[6-(3-dimethylaminopropoxy)-5-fluoro-1H-benzimidazol-2-yl]-1-(tetrahydro-pyran-2-yl)-1H-pyrazol-4-yl]-3-isobutylurea Starting from 50 mg of intermediate 2 and s-butylamine according to the general method. Analytical LC/MS: Tr=2.78 min; $[M+H]^+$=502.25; ELSD=58%; DAD=34%.

Stage C

Preparation of 1-{3-[6-(3-dimethylaminopropoxy)-5-fluoro-1H-benzimidazol-2-yl]-1H-pyrazol-4-yl}-3-isobutylurea The crude product obtained according to the general method is purified by preparative LC/MS with the standard gradient. 14.4 mg of 1-{3-[6-(3-dimethylaminopropoxy)-5-fluoro-1H-benzimidazol-2-yl]-1H-pyrazol-4-yl}-3-isobutylurea are obtained in the form of a brown powder. $^1$H NMR (400 MHz, DMSO-d6, δ in ppm): 0.86 (d, J=6.5 Hz, 6H); 1.68 (m, 1H); 2.19 (m, 2H); 2.85 (s, 6H); 2.93 (d, J=7.0 Hz, 2H); 3.28 (m, 2H); 4.21 (t, J=6.5 Hz, 2H); 7.39 (d, J=8.0 Hz, 1H); 7.62 (d, J=10.5 Hz, 1H); 8.07 (s, 1H).

Example 29

3-{3-[6-(3-Dimethylaminopropoxy)-5-fluoro-1H-benzimidazol-2-yl]-1H-pyrazol-4-yl}-1,1-diisopropylurea

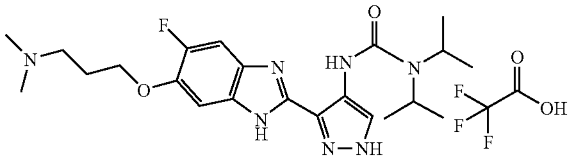

Stage B

Preparation of 3-[3-[6-(3-dimethylaminopropoxy)-5-fluoro-1H-benzimidazol-2-yl]-1-(tetrahydro-pyran-2-yl)-1H-pyrazol-4-yl]-1,1-diisopropylurea Starting from 50 mg of intermediate 2 and N,N-diisopropylamine.

Analytical LC/MS: Tr=3.18 min; $[M+H]^+$=530.25; ELSD=21%; DAD=25%.

Stage C

Preparation of 3-{3-[6-(3-dimethylaminopropoxy)-5-fluoro-1H-benzimidazol-2-yl]-1H-pyrazol-4-yl}-1,1-diisopropylurea The crude product obtained according to the general method is purified by preparative LC/MS with the standard gradient. 2.4 mg of 3-{3-[6-(3-dimethylaminopropoxy)-5-fluoro-1H-benzimidazol-2-yl]-1H-pyrazol-4-yl}-1,1-diisopropylurea are obtained in the form of a brown powder. Analytical LC/MS: Tr=2.8 min; $[M+H]^+$=446.42; ELSD=100%; DAD=94%.

Example 30

3-{3-[6-(3-Dimethylaminopropoxy)-5-fluoro-1H-benzimidazol-2-yl]-1H-pyrazol-4-yl}-1,1-dipropylurea

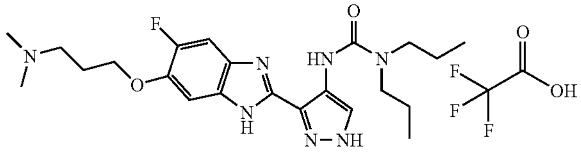

Stage B

3-[3-[6-(3-Dimethylaminopropoxy)-5-fluoro-1H-benzimidazol-2-yl]-1-(tetrahydropyran-2-yl)-1H-pyrazol-4-yl]-1,1-dipropylurea Starting from 50 mg of intermediate 2 and N,N-dipropylamine according to the general method. Analytical LC/MS: Tr=3.04 min; $[M+H]^+$=530.91; ELSD=92%; DAD=77%.

Stage C

3-{3-[6-(3-Dimethylaminopropoxy)-5-fluoro-1H-benzimidazol-2-yl]-1H-pyrazol-4-yl}-1,1-dipropylurea The crude product obtained according to the general method is purified by preparative LC/MS with the standard gradient. 35.4 mg of 3-{3-[6-(3-dimethylaminopropoxy)-5-fluoro-1H-benzimidazol-2-yl]-1H-pyrazol-4-yl}-1,1-dipropylurea are obtained in the form of a brown powder. $^1$H NMR (400 MHz, DMSO-d6, δ in ppm): 0.95 (t, J=7.0 Hz, 6H); 1.64 (m, 4H); 2.17 (m, 2H); 2.85 (s, 6H); 3.30 (m, 6H); 4.16 (t, J=6.5 Hz, 2H); 7.22 (d, J=7.5 Hz, 1H); 7.39 (d, J=11.0 Hz, 1H); 8.02 (s, 1H).

Example 31

N-{3-[6-(3-Dimethylaminopropoxy)-5-fluoro-1H-benzimidazol-2-yl]-1H-pyrazol-4-yl}piperazine-1-carboxamide

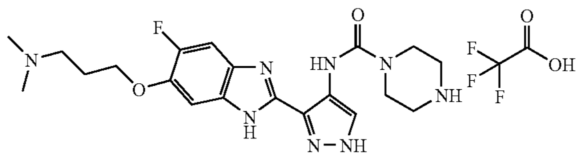

Stage B

4-[3-[6-(3-Dimethylaminopropoxy)-5-fluoro-1H-benzimidazol-2-yl]-1-(tetrahydropyran-2-yl)-1H-pyrazol-4-ylcarbamoyl]piperazine-1-carboxylic acid tert-butyl ester 10 eq of 1-Boc-piperazine are added to a solution of 50 mg of intermediate 2 in 1 mL of DMF. The reaction mixture is irradiated for 40 min at 200° C. in a microwave on a Personal Synthesizer. The reaction medium is concentrated under vacuum in a rotary evaporator. The concentrate is used immediately in the subsequent stage. Analytical LC/MS: Tr=3.11 min; $[M+H]^+$=615.41; ELSD=18%; DAD=18%.

Stage C

N-{3-[6-(3-Dimethylaminopropoxy)-5-fluoro-1H-benzimidazol-2-yl]-1H-pyrazol-4-yl}piperazine-1-carboxamide The crude product obtained according to the general method is purified by preparative LC/MS with the standard gradient. 28.2 mg of N-{3-[6-(3-dimethylaminopropoxy)-5-fluoro-1H-benzimidazol-2-yl]-1H-pyrazol-4-yl}piperazine-1-carboxamide are obtained in the form of a brown powder. $^1$H NMR (400 MHz, DMSO-d6, δ in ppm): 2.18 (m, 2H); 2.85 (s, 6H); from 3.17 to 3.33 (m, 6H); 3.70 (m, 4H); 4.18 (t, J=6.0 Hz, 2H); 7.31 (d, J=7.5 Hz, 1H); 7.61 (d, J=10.5 Hz, 1H); 8.04 (s, 1H).

Example 32

1-{3-[6-(3-Dimethylaminopropoxy)-5-fluoro-1H-benzimidazol-2-yl]-1H-pyrazol-4-yl}-3-ethylurea

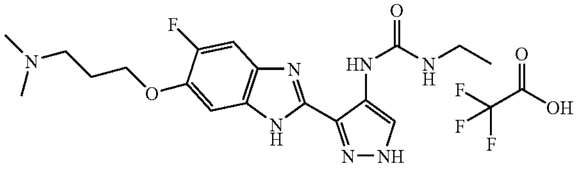

Stage B

1-[3-[6-(3-dimethylaminopropoxy)-5-fluoro-1H-benzimidazol-2-yl]-1-(tetrahydropyran-2-yl)-1H-pyrazol-4-yl]-3-ethylurea 50 eq of ethylamine in THF at 2N are added to 50 mg of intermediate 2. The reaction mixture is irradiated for 40 min at 160° C. in a microwave on a Personal Synthesizer. 10 eq of ethylamine are added. The reaction mixture is irradiated for 20 min at 80° C. in a microwave. The reaction medium is concentrated under vacuum in a rotary evaporator. 50 eq of ethylamine and 0.5 mL of DMF are added. The reaction mixture is irradiated for 10 min at 160° C., then for 20 min at 160° C., then for 60 min at 160° C., and then for 60 min at 160° C. in a microwave. The reaction medium is concentrated under vacuum in a rotary evaporator. 50 eq of ethylamine and 0.5 mL of DMF are added. The reaction mixture is irradiated for 60 min at 160° C. The reaction medium is concentrated under vacuum in a rotary evaporator. The concentrate is used immediately in the subsequent stage. Analytical LC/MS: Tr=2.34 min; $[M+H]^+$=474.34; ELSD=31%; DAD=22%.

Stage C

Preparation of 1-{3-[6-(3-dimethylaminopropoxy)-5-fluoro-1H-benzimidazol-2-yl]-1H-pyrazol-4-yl}-3-ethylurea The crude product obtained according to the general method is purified by preparative LC/MS with the standard gradient. 14.2 mg of 1-{3-[6-(3-dimethylaminopropoxy)-5-fluoro-1H-benzimidazol-2-yl]-1H-pyrazol-4-yl}-3-ethylurea are obtained in the form of a brown powder. $^1$H NMR (400 MHz, DMSO-d6, δ in ppm): 1.07 (t, J=7.5 Hz, 3H); 2.19 (m, 2H); 2.85 (s, 6H); 3.13 (q, J=7.5 Hz, 2H); 3.28 (m, 2H); 4.20 (t, J=6.0 Hz, 2H); 7.35 (d, J=7.5 Hz, 1H); 7.59 (d, J=10.5 Hz, 1H); 8.05 (s, 1H).

Example 33

3-{3-[6-(3-dimethylaminopropoxy)-5-fluoro-1H-benzimidazol-2-yl]-1H-pyrazol-4-yl}-1-ethyl-1-isopropylurea

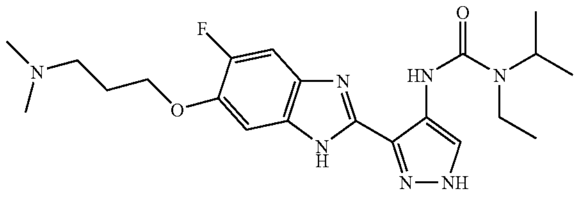 [SMILES: CCN(C(=O)Nc1c[nH]nc1-c1nc2cc(F)c(OCCCN(C)C)cc2[nH]1)C(C)C]

Stage B

3-[3-[6-(3-Dimethylaminopropoxy)-5-fluoro-1H-benzimidazol-2-yl]-1-(tetrahydropyran-2-yl)-1H-pyrazol-4-yl]-1-ethyl-1-isopropylurea Starting from 47 mg of intermediate 2 and N-ethyl-N-isopropylamine according to the general method. Analytical LC/MS: Tr=3.08 min; $[M+H]^+$=516.30; ELSD=82%; DAD=67%.

Stage C

Preparation of 3-{3-[6-(3-dimethylaminopropoxy)-5-fluoro-1H-benzimidazol-2-yl]-1H-pyrazol-4-yl}-1-ethyl-1-isopropylurea The crude product obtained according to the general method is purified by preparative LC/MS with the standard gradient. 15.7 mg of 3-{3-[6-(3-dimethylaminopropoxy)-5-fluoro-1H-benzimidazol-2-yl]-1H-pyrazol-4-yl}-1-ethyl-1-isopropylurea are obtained in the form of a brown powder. $^1$H NMR (400 MHz, DMSO-d6, δ in ppm): 1.17 (d, J=7.0 Hz, 6H); 1.28 (t, J=7.5 Hz, 3H); 2.17 (m, 2H); 2.85 (s, 6H); 3.27 (m, 2H); 3.33 (q, J=7.5 Hz, 2H); 4.18 (t, J=6.0 Hz, 2H); 4.41 (m, 1H); 7.26 (d, J=7.5 Hz, 1H); 7.47 (d, J=10.5 Hz, 1H); 8.01 (s, 1H).

Example 34

1,1-Diisopropyl-3-{3-[6-(4-methylpiperazin-1-yl)-1H-benzimidazol-2-yl]-1H-pyrazol-4-yl}urea

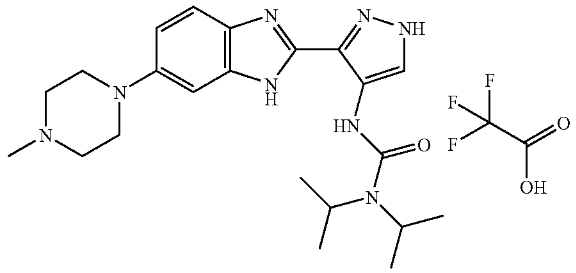

Stage III 1,1-Diisopropyl-3-[3-[6-(4-methylpiperazin-1-yl)-1H-benzimidazol-2-yl]-1-(tetrahydropyran-2-yl)-1H-pyrazol-4-yl]urea 5 eq of diisopropylcarbamoyl chloride and 1 eq of N,N-diisopropylethylamine are added to a solution of 200 mg of intermediate 3 in 22 mL of THF. The reaction mixture is heated at 52° C. for 4 hours. The reaction medium is cooled to ambient temperature and 20 mL of a saturated solution of sodium bicarbonate are added. The aqueous phase is extracted with 3 times 20 mL of EtOAc. The organic phases are dried over $MgSO_4$, filtered and concentrated under vacuum in a rotary evaporator. 230 mg of 1,1-diisopropyl-3-[3-[6-(4-methylpiperazin-1-yl)-1H-benzimidazol-2-yl]-1-(tetrahydropyran-2-yl)-1H-pyrazol-4-yl]urea are obtained. Analytical LC/MS: Tr=3.04 min; $[M+H]^+$=509.32; ELSD=82%; DAD=100%.

Stage IV

Preparation of 1,1-diisopropyl-3-{3-[6-(4-methylpiperazin-1-yl)-1H-benzimidazol-2-yl]-1H-pyrazol-4-yl}urea A solution of 230 mg of 1,1-diisopropyl-3-[3-[6-(4-methylpiperazin-1-yl)-1H-benzimidazol-2-yl]-1-(tetrahydropyran-2-yl)-1H-pyrazol-4-yl]urea in solution in 40 eq of a 4N solution of hydrochloric acid in dioxane is stirred at 22° C. for approximately 4 hours, and precipitation occurs. The suspension is filtered through sintered glass and the solid is rinsed with dioxane and with isopropyl ether. The precipitate is dried in an oven. The precipitate is dissolved in 5 mL of 2N NaOH, and then extracted with 2 times 5 mL of ethyl acetate then 2 times 10 mL of ethyl acetate. The organic phases are dried over $MgSO_4$, filtered and concentrated under vacuum in a rotary evaporator. The concentrate is purified by preparative HPLC with, as eluent, a gradient of water/acetonitrile containing respectively 0.07% of trifluoroacetic acid. 99 mg of 1,1-diisopropyl-3-{3-[6-(4-methylpiperazin-1-yl)-1H-benzimidazol-2-yl]-1H-pyrazol-4-yl}urea are isolated in the form of a pale yellow powder. $^1$H NMR (400 MHz, DMSO-d6, δ in ppm): 1.25 (d, J=7.0 Hz, 12H); 2.90 (s, 3H); 3.03 (m, 2H); 3.23 (m, 2H); 3.58 (m, 2H); 3.87 (m, 4H); 7.12 (d, J=2.0 Hz, 1H); 7.24 (dd, J=2.0 and 9.0 Hz, 1H); 7.58 (d, J=9.0 Hz, 1H); 7.98 (s, 1H).

Example 35

3-{3-[6-(4-Methylpiperazin-1-yl)-1H-benzimidazol-2-yl]-1H-pyrazol-4-yl}-1,1-dipropylurea

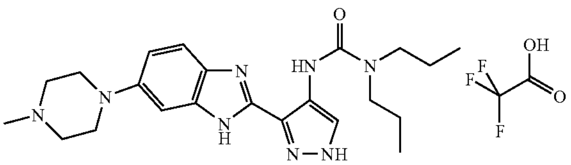

Stage III

[3-[6-(4-Methylpiperazin-1-yl)-1H-benzimidazol-2-yl]-1-(tetrahydropyran-2-yl)-1H-pyrazol-4-yl]carbamic Acid Ethyl Ester 50 µL of ethyl chloroformate and 73 µL of triethylamine are added to a solution of 200 mg of intermediate 3 in 3.6 mL of dichloromethane. The reaction mixture is stirred at 22° C. for 72 hours. The reaction medium is washed with 4 mL of water. The aqueous phase is extracted with 3 times 4 mL of dichloromethane. The organic phases are dried over $MgSO_4$, filtered and concentrated under vacuum in a rotary evaporator. 168 mg of [[3-[6-(4-methylpiperazin-1-yl)-1H-benzimidazol-2-yl]-1-(tetrahydropyran-2-yl)-1H-pyrazol-4-yl]carbamic acid ethyl ester are obtained in the form of a pale yellow solid. $^1$H NMR (400 MHz, DMSO-d6, δ in ppm): 1.24 (m, 3H); 1.60 to 2.21 (m, 6H); 2.90 (s, 3H); 3.03 (t, 2H); 3.23 (t, 2H); 3.58 (d, 2H); 3.70 (m, 1H); 3.89 (d, 2H); 3.98 (m, 1H); 4.15 (q, 2H); 5.55 (m, 1H); 7.16 (d, J=2.0 Hz, 1H); 7.28 (dd, J=2.0 and 9.0 Hz, 1H); 7.64 (d, J=9.0 Hz, 1H); 8.21 (s, 1H). Analytical LC/MS: Tr=2.38 min; $[M+H]^+$=454.32; ELSD=100%; DAD=91%.

Stage IV

3-[3-[6-(4-Methylpiperazin-1-yl)-1H-benzimidazol-2-yl]-1-(tetrahydropyran-2-yl)-1H-pyrazol-4-yl]-1,1-dipropylurea 50 eq of dipropylamine are added to a solution of 118 mg of [3-[6-(4-methylpiperazin-1-yl)-1H-benzimidazol-2-yl]-1-(tetrahydropyran-2-yl)-1H-pyrazol-4-yl]carbamic acid ethyl ester in 4.1 mL of DMF. The reaction mixture is irradiated for 40 min at 200° C. with microwaves on a Personal Synthesizer. The reaction medium is concentrated under vacuum in a rotary evaporator. The concentrate is used immediately in the subsequent stage. Analytical LC/MS: Tr=3.23 min; $[M+H]^+$=509.92; ELSD=91%; DAD=70%.

Stage V

3-{3-[6-(4-Methylpiperazin-1-yl)-1H-benzimidazol-2-yl]-1H-pyrazol-4-yl}-1,1-dipropylurea A solution of 190 mg of 3-[3-[6-(4-methylpiperazin-1-yl)-1H-benzimidazol-2-yl]-1-(tetrahydropyran-2-yl)-1H-pyrazol-4-yl]-1,1-dipropylurea in solution in 3.5 mL of a 4N solution of hydrochloric acid in dioxane is stirred at 22° C. for 4 hours. A solid precipitates. The solid is filtered off and washed with dioxane and with isopropyl ether. The solid becomes pasty. Filtrate and precipitate are grouped together with methanol and the mixture is concentrated. The reaction crude is dissolved in a 2N aqueous solution of NaOH, and a sticky paste forms, which does not dissolve. It is recovered with methanol and the product is concentrated. The concentrate is dissolved in 10 mL of water and extracted with 2 times 10 mL and 2 times 15 mL of ethyl acetate. The organic phases are dried over $MgSO_4$, filtered and concentrated under vacuum in a rotary evaporator. The precipitate obtained is purified by preparative HPLC with, as eluent, a gradient of water/acetonitrile containing respectively 0.07% of trifluoroacetic acid. 65 mg of 3-{3-[6-(4-methylpiperazin-1-yl)-1H-benzimidazol-2-yl]-1H-pyrazol-4-yl}-1,1-dipropylurea are obtained in the form of a yellow solid. $^1$H NMR (400 MHz, DMSO-d6, δ in ppm): 0.89 (t, J=7.5 Hz, 6H); 1.57 (m, 4H); 2.89 (s, 3H); 3.03 (m, 2H); 3.23 (m partially masked, 2H); 3.29 (m, 4H); 3.57 (m, 2H); 3.87 (m, 2H); 7.13 (d, J=2.0 Hz, 1H); 7.24 (broad d, J=9.0 Hz, 1H); 7.59 (d, J=9.0 Hz, 1H); 7.98 (s, 1H).

Example 36

N-{3-[6-(3-Dimethylaminopropoxy)-5-fluoro-1H-benzimidazol-2-yl]-1H-pyrazol-4-yl}-4-methylpiperazine-1-carboxamide

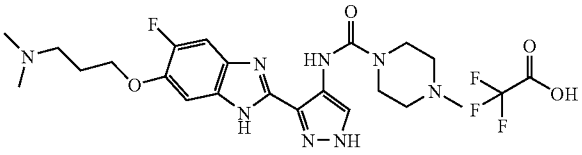

Stage B

N-[3-[6-(3-Dimethylaminopropoxy)-5-fluoro-1H-benzimidazol-2-yl]-1-(tetrahydropyran-2-yl)-1H-pyrazol-4-yl]-4-methylpiperazine-1-carboxamide Starting from 47 mg of intermediate 2 and N-methylpiperazine according to the general method. Analytical LC/MS: Tr=1.92 min; $[M+H]^+$=528.99; ELSD=93%; DAD=81%.

Stage C

Preparation of N-{3-[6-(3-dimethylaminopropoxy)-5-fluoro-1H-benzimidazol-2-yl]-1H-pyrazol-4-yl}-4-methylpiperazine-1-carboxamide The crude product obtained according to the general method is purified by preparative HPLC with, as eluent, a gradient of water/acetonitrile containing respectively 0.07% of trifluoroacetic acid. 16.9 mg of N-{3-[6-(3-dimethylaminopropoxy)-5-fluoro-1H-benzimidazol-2-yl]-1H-pyrazol-4-yl}-4-methylpiperazine-1-carboxamide are obtained in the form of a brown powder. $^1$H NMR (400 MHz, DMSO-d6, δ in ppm): 2.19 (m, 2H); 2.85 (s, 6H); 2.87 (s, 3H); 3.06 (m, 2H);

3.27 (m, 4H); 3.52 (m, 2H); 4.20 (m, 4H); 7.35 (d, J=7.5 Hz, 1H); 7.63 (d, J=10.5 Hz, 1H); 8.04 (s, 1H).

Example 37

1-Ethyl-1-isopropyl-3-{3-[6-(4-methylpiperazin-1-yl)-1H-benzimidazol-2-yl]-1H-pyrazol-4-yl}urea

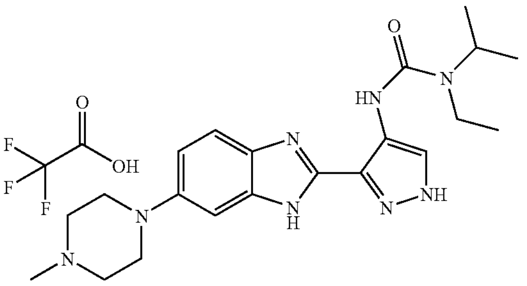

Stage III

1-Ethyl-1-isopropyl-3-[3-[6-(4-methylpiperazin-1-yl)-1H-benzimidazol-2-yl]-1-(tetrahydro-pyran-2-yl)-1H-pyrazol-4-yl]urea A solution of 300 mg of intermediate 3 in solution in 1 mL of acetonitrile and 2 mL of DMF is added to a solution of 16 mg of imidazole and of 192 mg of N,N'-carbonyldiimidazole in 4.5 mL of acetonitrile cooled to 0° C. The reaction mixture is stirred at 22° C. for 2 hours. 685 μL of N-ethylisopropylamine are added. The reaction mixture is irradiated for 45 min at 150° C. in a microwave on a Personal Synthesizer. The reaction medium is concentrated under vacuum in a rotary evaporator. The concentrate is used immediately in the subsequent stage. Analytical LC/MS: Tr=2.9 min; $[M+H]^+$=495.29; ELSD=90%; UV254 nm=58%.

Stage IV

Preparation of 1-Ethyl-1-isopropyl-3-{3-[6-(4-methylpiperazin-1-yl)-1H-benzimidazol-2-yl]-1H-pyrazol-4-yl}urea A solution of the concentrate in solution in 40 eq of a 4N solution of hydrochloric acid in dioxane is stirred at 22° C. for approximately 4 hours (until the starting product has disappeared). The reaction medium is concentrated under vacuum in a rotary evaporator. The concentrate is purified by preparative LC/MS with, as eluent, a gradient of water/acetonitrile containing respectively 0.07% of trifluoroacetic acid. 160 mg of 1-ethyl-1-isopropyl-3-{3-[6-(4-methylpiperazin-1-yl)-1H-benzimidazol-2-yl]-1H-pyrazol-4-yl}urea are obtained in the form of a brown powder. $^1$H NMR (300 MHz, DMSO-d6, δ in ppm): 1.13 (d, J=6.5 Hz, 6H); 1.16 (t partially masked, J=7.0 Hz, 3H); 2.90 (s, 3H); 3.04 (m, 2H); 3.23 (m, 2H); 3.28 (q partially masked, J=7.0 Hz, 2H); 3.57 (m, 2H); 3.88 (m, 2H); 4.34 (m, 1H); 7.16 (d, J=2.0 Hz, 1H); 7.27 (dd, J=2.0 and 9.0 Hz, 1H); 7.62 (d, J=9.0 Hz, 1H); 8.00 (s, 1H).

Example 38

N-[3-(5-fluoro-6-(1,4-oxazepan-4-yl-1H-benzimidazol-2-yl)-1H-pyrazol-4-yl]piperidine-1-carboxamide Stage V Preparation of N-[3-(5-fluoro-6-perhydro-1,4-oxazepin-4-yl-1H-benzimidazol-2-yl)-1-(tetrahydropyran-2-yl)-1H-pyrazol-4-yl]piperidine-1-carboxamide

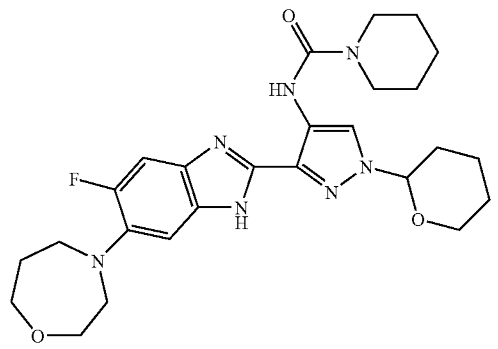 [SMILES: O=C(Nc1cn(C2CCCCO2)nc1-c1nc2cc(F)c(N3CCCOCC3)cc2[nH]1)N1CCCCC1]

570 μL of 1-piperidinecarbonyl chloride and 800 μL of N,N-diisopropylethylamine are added to a solution of 367 mg of intermediate 6 in 5 mL of THF. The reaction mixture is heated at 80° C. for 5 hours. The reaction medium is cooled to ambient temperature and concentrated under vacuum in a rotary evaporator. The reaction crude is purified by flash chromatography, elution being carried out with the mixture of dichloromethane/methanol. The mixture containing the expected product is concentrated and then repurified by flash chromatography, elution being carried out with a mixture of cyclohexane/ethyl acetate. 80 mg of N-[3-(5-fluoro-6-perhydro-1,4-oxazepin-4-yl-1H-benzimidazol-2-yl)-1-(tetrahydropyran-2-yl)-1H-pyrazol-4-yl]piperidine-1-carboxamide are obtained in the form of a beige foam. $^1$H NMR (400 MHz DMSO-d6, δ in ppm): from 1.30 to 2.24 (m, 14H); 3.43 (m, 4H); 3.51 (m, 4H); 3.66 (m, 1H); 3.76 (m, 2H); 3.82 (m, 2H); 3.96 (m, 1H); 5.51 (broad d, J=10.0 Hz, 1H); 7.34 (d, J=7.5 Hz, 1H); 7.55 (d, J=12.0 Hz, 1H); 8.15 (s, 1H).

Stage VI

N-[3-(5-Fluoro-6-perhydro-1,4-oxazepin-4-yl-1H-benzimidazol-2-yl)-1H-pyrazol-4-yl]piperidine-1-carboxamide A solution of 80 mg of N-[3-(5-fluoro-6-perhydro-1,4-oxazepin-4-yl-1H-benzimidazol-2-yl)-1-(tetrahydropyran-2-yl)-1H-pyrazol-4-yl]piperidine-1-carboxamide in solution in 4 mL of a 4N solution of hydrochloric acid in dioxane is stirred at 22° C. for 1 hour. The reaction medium is concentrated under vacuum in a rotary evaporator, and then reacted again at 22° C. for 16 hours with 4 mL of a 4N solution of hydrochloric acid in dioxane is stirred at 22° C. The reaction medium is concentrated under vacuum in a rotary evaporator. The product is made into a paste in isopropyl ether, but the product is hydroscopic. The reaction crude is purified by flash chromatography, elution being carried out with a mixture of cyclohexane/ethyl acetate then dichloromethane/methanol. The product is diluted in ethyl acetate, and washed with 2 times 5 mL of a 2N aqueous solution of sodium hydroxide. The aqueous phases are extracted with 3 times 10 mL of ethyl acetate. The organic phases are dried over $MgSO_4$, filtered and concentrated under vacuum in a rotary evaporator. 65 mg of N-[3-(5-fluoro-6-perhydro-1,4-oxazepin-4-yl-1H-benzimidazol-2-yl)-1H-pyrazol-4-yl]piperidine-1-carboxamide are obtained in the form of a gray solid.

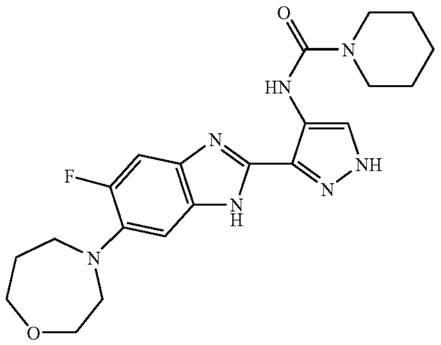 [SMILES: O=C(Nc1c[nH]nc1-c1nc2cc(F)c(N3CCCOCC3)cc2[nH]1)N1CCCCC1]

$^1$H NMR (400 MHz, DMSO-d6, δ in ppm): 1.58 (m, 6H); 1.99 (m, 2H); 3.30 (m partially masked, 4H); 3.49 (m, 4H); 3.78 (m, 4H); from 7.03 to 7.40 (broad m, 2H); 7.99 (s, 1H); 9.93 (s, 1H); 12.9 (broad m, 2H).

Example 39

3-{3-[5-Fluoro-6-(4-methylpiperazin-1-yl)-1H-benzimidazol-2-yl]-1H-pyrazol-4-yl}-1,1-diisopropylurea trifluoroacetate

Stage V

3-[3-[5-Fluoro-6-(4-methylpiperazin-1-yl)-1H-benzimidazol-2-yl]-1-(tetrahydropyran-2-yl)-1H-pyrazol-4-yl]-1,1-diisopropylurea

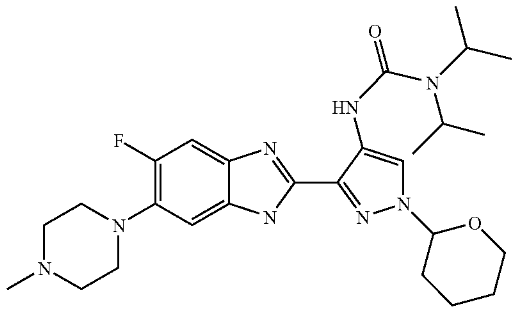 [SMILES: CC(C)N(C(=O)Nc1cn(C2CCCCO2)nc1-c1nc2cc(F)c(N3CCN(C)CC3)cc2[nH]1)C(C)C]

82 mg of diisopropylcarbamoyl chloride and 436 μL of N,N-diisopropylethylamine are added to a solution of 200 mg of intermediate 5 in 21.2 mL of THF. The reaction mixture is heated at 66° C. for 1.7 hours, then stirred for 16 hours at ambient temperature, then heated at 66° C. for 7.75 hours, then stirred for 16 hours at ambient temperature, then heated at 66° C. for 8 hours, and then stirred for 16 hours. The reaction medium is washed with 20 mL of saturated $NaHCO_3$ solution water. The aqueous phase is extracted with 3 times 20 mL of EtOAc. The organic phases are dried over $MgSO_4$, filtered and concentrated under vacuum in a rotary evaporator. 364 mg of 3-[3-[5-fluoro-6-(4-methylpiperazin-1-yl)-1H-benzimidazol-2-yl]-1-(tetrahydropyran-2-yl)-1H-pyrazol-4-yl]-1,1-diisopropylurea are obtained in the form of an orange solid. $^1$H NMR (400 MHz, DMSO-d6, δ in ppm): 1.32 (d, J=7.0 Hz, 12H); from 1.51 to 2.20 (m, 6H); 2.89 (s, 3H); 3.05 (m, 2H); 3.28 (m, 2H); 3.53 (m, 4H); 3.66 (m, 1H); 3.96 (m, 1H); 4.02 (m, 2H); 5.46 (dd, J=2.0 and 10.0 Hz, 1H); 7.16 (d, J=8.0 Hz, 1H); 7.40 (d, J=11.5 Hz, 1H); 8.16 (s, 1H). ES mass spectrum: m/z=527: MH+ (base peak)—m/z=426: (M+H—$C_6H_{15}N$)+—m/z=342: (m/z=426—$C_5H_8O$)+.

Stage VI

3-{3-[5-Fluoro-6-(4-methylpiperazin-1-yl)-1H-benzimidazol-2-yl]-1H-pyrazol-4-yl}-1,1-diisopropylurea in the Form of a Trifluoroacetate Salt

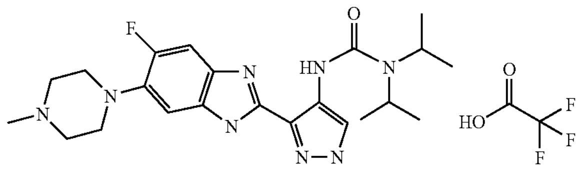 [SMILES: CC(C)N(C(=O)Nc1c[nH]nc1-c1nc2cc(F)c(N3CCN(C)CC3)cc2[nH]1)C(C)C ; O=C(O)C(F)(F)F]

A solution of 364 mg of 3-[3-[5-fluoro-6-(4-methylpiperazin-1-yl)-1H-benzimidazol-2-yl]-1-(tetrahydropyran-2-yl)-1H-pyrazol-4-yl]-1,1-diisopropylurea in solution in 6.9 mL of a 4N solution of hydrochloric acid in dioxane is stirred at 22° C. for 4 hours. After evaporation, the reaction crude is purified by preparative HPLC with, as eluent, a gradient of water/acetonitrile containing respectively 0.07% of trifluoroacetic acid. 123 mg of 3-{3-[5-fluoro-6-(4-methylpiperazin-1-yl)-1H-benzimidazol-2-yl]-1H-pyrazol-4-yl}-1,1-diisopropylurea in the form of a trifluoroacetate salt are obtained in the form of a pink solid. $^1$H NMR (400 MHz, DMSO-d6, δ in ppm): 1.32 (d, J=7.0 Hz, 12H); 2.91 (s, 3H); 3.04 (m, 2H); 3.28 (m, 2H); 3.53 (m, 4H); 4.01 (m, 2H); 7.18 (d, J=8.0 Hz, 1H); 7.41 (d, J=11.5 Hz, 1H); 8.03 (s, 1H). ES m/z=443: MH+ (base peak)—m/z=342: (M+H—$C_6H_{15}N$)+.

Example 40

3-{3-[5-Fluoro-6-(4-methylperhydro-1,4-diazepin-1-yl)-1H-benzimidazol-2-yl]-1H-pyrazol-4-yl}-1,1-diisopropylurea

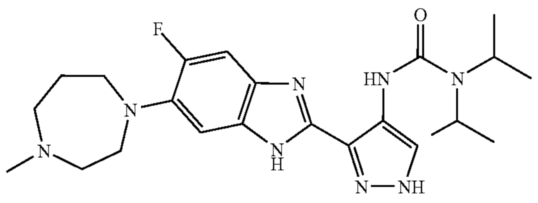 [SMILES: CC(C)N(C(=O)Nc1c[nH]nc1-c1nc2cc(F)c(N3CCCN(C)CC3)cc2[nH]1)C(C)C]

Stage V

3-[3-[5-Fluoro-6-(4-methylperhydro-1,4-diazepin-1-yl)-1H-benzimidazol-2-yl]-1-(tetrahydro-pyran-2-yl)-1H-pyrazol-4-yl]-1,1-diisopropylurea

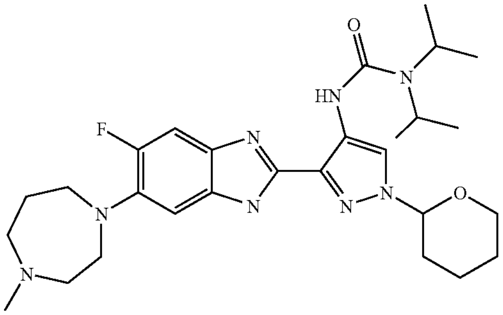 [SMILES: CC(C)N(C(=O)Nc1cn(C2CCCCO2)nc1-c1nc2cc(F)c(N3CCCN(C)CC3)cc2[nH]1)C(C)C]

70 mg of diisopropylcarbamoyl chloride and 373 μL of N,N-diisopropylethylamine are added to a solution of 177 mg of intermediate 4 in 20 mL of THF. The reaction mixture is heated at 66° C. for 3 hours, then stirred for 65 hours at ambient temperature, then heated at 66° C. for 7.75 hours, then stirred for 16 hours at ambient temperature, then heated at 66° C. for 7.75 hours, then stirred for 16 hours at ambient temperature, then heated at 66° C. for 3.5 hours, and then stirred for 16 hours at ambient temperature. 20 mL of a saturated solution of $NaHCO_3$ are added. The aqueous phase is extracted with 3 times 20 mL of EtOAc. The organic phases are dried over $MgSO_4$, filtered and concentrated under vacuum in a rotary evaporator. 159 mg of 3-[3-[5-fluoro-6-(4-methylperhydro-1,4-diazepin-1-yl)-1H-benzimidazol-2-yl]-1-(tetrahydropyran-2-yl)-1H-pyrazol-4-yl]-1,1-diisopropylurea are obtained in the form of an orange solid. Analytical LC/MS: Tr=3.24 min; $[M+H]^+$=541.67; ELSD=87%; DAD=37%.

Stage VI

3-{3-[5-Fluoro-6-(4-methylperhydro-1,4-diazepin-1-yl)-1H-benzimidazol-2-yl]-1H-pyrazol-4-yl}-1,1-diisopropylurea A solution of 278.5 mg of 3-[3-[5-fluoro-6-(4-methylperhydro-1,4-diazepin-1-yl)-1H-benzimidazol-2-yl]-1-(tetrahydropyran-2-yl)-1H-pyrazol-4-yl]-1,1-diisopropylurea in solution in 5.1 mL of a 4N solution of hydrochloric acid in dioxane is stirred at 22° C. for 4 hours. After evaporation, the reaction crude is purified by preparative HPLC with, as eluent, a gradient of water/acetonitrile containing respectively 0.07% of trifluoroacetic acid. 15.2 mg of 3-{3-[5-fluoro-6-(4-methylperhydro-1,4-diazepin-1-yl)-1H-benzimidazol-2-yl]-1H-pyrazol-4-yl}-1,1-diisopropylurea are isolated in the form of a trifluoroacetate salt. $^1H$ NMR (300 MHz, DMSO-d6, δ in ppm): 1.26 (d, J=7.0 Hz, 12H); 2.21 (broad m, 2H); 2.90 (s, 3H); from 3.14 to 3.68 (m, 8H); 3.90 (m, 2H); 7.16 (d, J=8.0 Hz, 1H); 7.48 (d, J=12.0 Hz, 1H); 7.98 (s, 1H). ES mass spectrum: m/z=457: MH+(base peak)—m/z=330 (MH−$C_7H_{13}NO$)+.

TABLE I (compounds of formula (I) with $R_1 = R_4 = H$)

| Ex | $R_2$ | $R_3$ | $R_5$ |
|---|---|---|---|
| 1 | F | 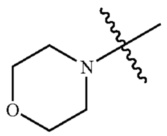 [SMILES: *N1CCOCC1] | 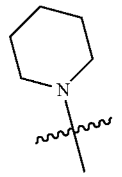 [SMILES: *N1CCCCC1] |
| 2 | F | 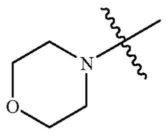 [SMILES: *N1CCOCC1] | —$NEt_2$ |
| 3 | F | 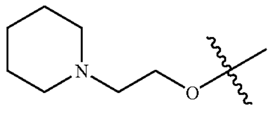 [SMILES: *OCCN1CCCCC1] | 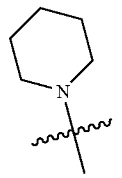 [SMILES: *N1CCCCC1] |
| 4 | F | 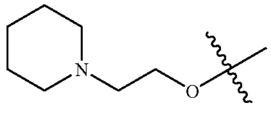 [SMILES: *OCCN1CCCCC1] | —$NEt_2$ |
| 5 | F | $Me_2N(CH_2)_3O$— | —$NEt_2$ |

TABLE I-continued
| (compounds of formula (I) with $R_1 = R_4 = H$) | | | |
|---|---|---|---|
| Ex | $R_2$ | $R_3$ | $R_5$ |
| 6 | F | 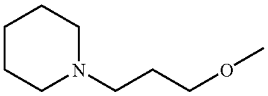 | —$NEt_2$ |
| 7 | F | $Me_2N(CH_2)_3O$— | 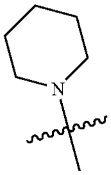 [SMILES: *N1CCCCC1] |
| 8 | F | 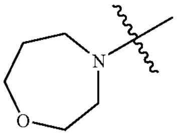 [SMILES: *N1CCCOCC1] | —$N(^iPr)_2$ |
| 9 | 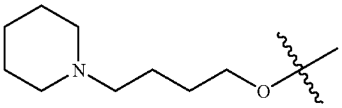 [SMILES: *OCCCCN1CCCCC1] | F | —$NEt_2$ |
| 10 | 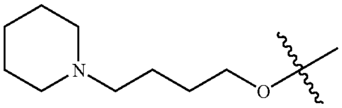 [SMILES: *OCCCCN1CCCCC1] | F | 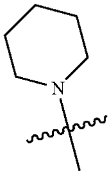 [SMILES: *N1CCCCC1] |
| 11 | F | 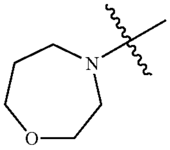 [SMILES: *N1CCCOCC1] | —$NEt_2$ |
| 12 | F | 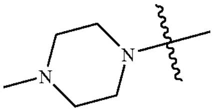 [SMILES: *N1CCN(C)CC1] | 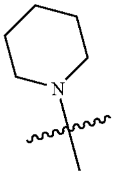 [SMILES: *N1CCCCC1] |
| 13 | F | 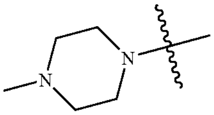 [SMILES: *N1CCN(C)CC1] | —$NEt_2$ |
| 14 | F | ($Et_2N$—CO)($Me_2NCH_2CH_2$)N— | —$NEt_2$ |
| 15 | F | $NMe_2CH_2CH_2NH$— | —$NEt_2$ |
| 16 | F | 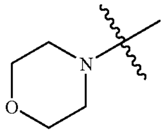 | —$N(^iPr)_2$ |

TABLE I-continued
| (compounds of formula (I) with $R_1 = R_4 = H$) | | | |
|---|---|---|---|
| Ex | $R_2$ | $R_3$ | $R_5$ |
| 17 | F | 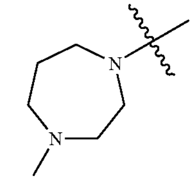 [SMILES: *N1CCCN(C)CC1] | 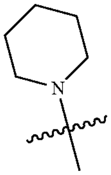 [SMILES: *N1CCCCC1] |
| 18 | F | 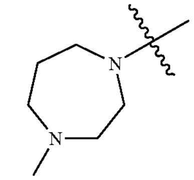 [SMILES: *N1CCCN(C)CC1] | —$NEt_2$ |
| 19 | H | 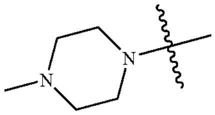 [SMILES: *N1CCN(C)CC1] | —$NEt_2$ |
| 20 | H | 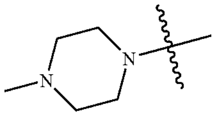 [SMILES: *N1CCN(C)CC1] | 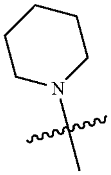 [SMILES: *N1CCCCC1] |
| 21 | F | 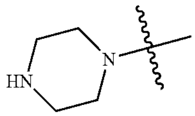 [SMILES: *N1CCNCC1] | 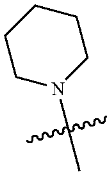 [SMILES: *N1CCCCC1] |
| 22 | F | $NMe_2(CH_2)_3O$— | —NHCy |
| 23 | F | $NMe_2(CH_2)_3O$— | 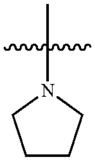 [SMILES: *N1CCCC1] |
| 24 | F | $NMe_2(CH_2)_3O$— | —NH($^i$Pr) |
| 25 | F | $NMe_2(CH_2)_3O$— | 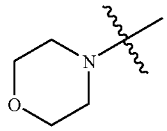 [SMILES: *N1CCOCC1] |
| 26 | F | $NMe_2(CH_2)_3O$— | —NMe($^i$Pr) |
| 27 | F | $NMe_2(CH_2)_3O$— | —NH($^t$Bu) |
| 28 | F | $NMe_2(CH_2)_3O$— | —NH($^i$Bu) |
| 29 | F | $NMe_2(CH_2)_3O$— | —N($^i$Pr)$_2$ |
| 30 | F | $NMe_2(CH_2)_3O$— | —N($^n$Pr)$_2$ |
| 31 | F | $NMe_2(CH_2)_3O$— | 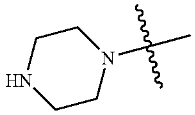 [SMILES: *N1CCNCC1] |

TABLE I-continued (compounds of formula (I) with $R_1 = R_4 = H$)

| Ex | $R_2$ | $R_3$ | $R_5$ |
|---|---|---|---|
| 32 | F | $NMe_2(CH_2)_3O$— | —NHEt |
| 33 | F | $NMe_2(CH_2)_3O$— | —NEt($^{i}$Pr) |
| 34 | H | 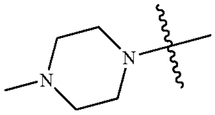 [SMILES: *N1CCN(C)CC1] | —N($^{i}$Pr)$_2$ |
| 35 | H | 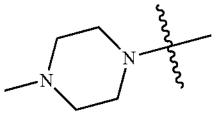 [SMILES: *N1CCN(C)CC1] | N($^{n}$Pr2) |
| 36 | F | $NMe_2(CH_2)_3O$— | 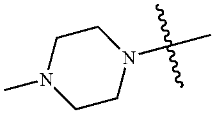 [SMILES: *N1CCN(C)CC1] |
| 37 | H | 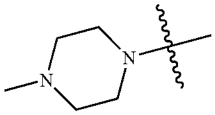 [SMILES: *N1CCN(C)CC1] | —NEt($^{i}$Pr) |
| 38 | F | 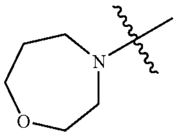 [SMILES: *N1CCCOCC1] | 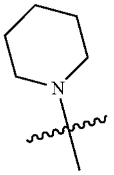 [SMILES: *N1CCCCC1] |
| 39 | F | 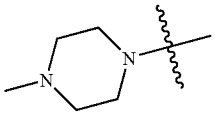 [SMILES: *N1CCN(C)CC1] | —N($^{i}$Pr)$_2$ |
| 40 | F | 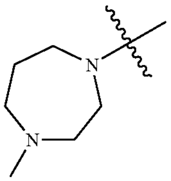 [SMILES: *N1CCCN(C)CC1] | —N($^{i}$Pr)$_2$ |

Experimental Protocols of the Cell Assays

The compounds were tested in a viability/proliferation assay for comparing, under similar conditions, their activity on proliferating tumor cells and on quiescent normal cells.

Cell Origin:

The HeLa cells (tumor cell line) and the PBLs (quiescent cells, peripheral blood lymphocytes) originate, respectively, from the ATCC and from Cambrex.

Principle of the FDA-PI Viability/Proliferation Assay:

The HeLa cells (tumor cell line) are seeded at $0.25 \times 10^6$ cells/well in 2 mL of culture medium. The products are added 24 h after seeding. After incubation for 48 h in the presence of the products, all the HeLa cells (supernatant and adherent cells) are recovered, centrifuged and taken up in PBS containing a final concentration of 0.25 μg/mL of fluorescein diacetate (FDA), 10 μg/mL of propidium iodide (PI) and 3 μL/mL of 10 μm beads. The cell suspensions are filtered immediately before analysis on the Facscalibur. The PBLs are seeded at $10^6$ cells/well in 2 mL of culture medium. The products are added 1-4 h after seeding. After incubation for 48 h in the presence of the products, half the cell suspension is recovered and incubated in the presence of a final concentration of 0.25 μg/mL of fluorescein diacetate (FDA), 10 μg/mL of propidium iodide (PI) and 2 μL/mL of 10 μm beads.

Reading Principle:

The FDA which enters the cells is cleaved by esterases only in live cells, releasing the fluorescein which emits a fluorescent radiation in the green range when it is excited (generally by UV radiation). The PI enters only the dead cells, the membrane of which is permeabilized, and emits a fluorescent radiation in the red range when it is excited. The beads are used as tracers for the dead cells having already disappeared at the time of reading.

Calculation: The % of viable cells relative to the nontreated control is given by: (number of live cells/number of live cells in the control)/(number of beads/number of beads in the control)×100 for the HeLa cells, and by: (number of live cells/number of live cells in the control)×100 for the quiescent PBLs. The products according to the invention are tested at several concentrations and an IC50, corresponding to the concentration which causes 50% of the maximum inhibition, is calculated.

The products according to the invention exhibit cellular activity in the tumor cell (HeLa line) viability/proliferation inhibition assay and great selectivity with respect to quiescent peripheral blood lymphocytes (PBLs), as quiescent cell model. The PBL viability inhibition IC50/HeLa cell viability inhibition IC50 ratio for the products according to the invention is greater than 10, and generally greater than 50; with a HeLa cell viability inhibition IC50 of less than 1 μM.

The IC50 values, on the tumor cells, for the compounds according to the invention range from 5 to 50 μM. In particular, the IC50 values for the compounds of examples 2, 4, 5, 6, 8, 9, 11, 13, 15, 16, 19, 20, 33, 34, 37, 39 and 40 are less than 100 nM. In particular, that for the compound of example 31 is between 5 and 30 μM.

TABLE II

| Example | Viability PBL IC50 (nM) | Viability HeLa IC50 (nM) | ratio |
|---|---|---|---|
| 1 | 7552 | 107 | 70 |
| 12 | 3487 | 56 | 62 |
| 17 | 4246 | 100 | 42 |
| 18 | 3764 | 39 | 96 |
| 38 | 9166 | 85 | 108 |

The invention claimed is:

1. A compound of general formula (I) below:

(I)

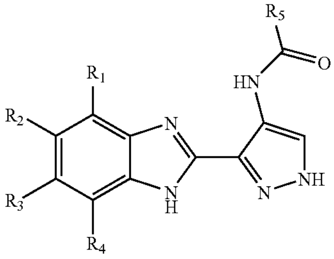

in which:

$R_1$ and $R_4$ are independently selected from the group consisting of H, Me, Et, $CO_2R_c$, $CH_2OR_c$, $OR_c$, F, Cl and C(=O)NH($R_d$); in which $R_c$ is chosen from H, ($C_1$-$C_6$)alkyl, substituted ($C_1$-$C_6$)alkyl, ($C_3$-$C_7$)cycloalkyl, substituted ($C_3$-$C_7$)cycloalkyl, aryl, substituted aryl, heteroaryl and substituted heteroaryl; and in which $R_d$ is chosen from H, ($C_1$-$C_6$)alkyl, substituted ($C_1$-$C_6$)alkyl, ($C_3$-$C_7$)cycloalkyl, substituted ($C_3$-$C_7$)cycloalkyl, and optionally substituted ($C_3$-$C_7$)heterocycloalkyl comprising from 1 to 3 heteroatoms chosen from N, O and S;

$R_3$ is $O(CH_2)_nN(Me)_2$ with n=2, 3 or 4, or $NH(CH_2)_2N(Me)_2$; and $R_2$ is F;

$R_5$ is selected from the group consisting of NMe(Et), NH($^i$Pr), $N(Et)_2$, $N(^iPr)_2$, NEt($^i$Pr), pyrrolidinyl, piperidinyl, morpholinyl, N-methylpiperazinyl, NH(Cy), $N(Cy)_2$, NMe($^i$Pr), NH($^i$Bu), NH($^t$Bu), $N(^nBu)_2$, piperazinyl, NH(Et), $N(^nPr)_2$ and NEt($^i$Pr);

or a salt thereof.

2. A compound as claimed in claim 1, wherein $R_5$ is selected from the group consisting of NMe(Et), NH($^i$Pr), $N(Et)_2$, $N(^iPr)_2$, NEt($^i$Pr), pyrrolidinyl, piperidinyl, morpholinyl, N-methylpiperazinyl, NH(Cy) and $N(Cy)_2$;

or a salt thereof.

3. A compound according to claim 1 wherein:

$R_5$ is NH($^i$Pr), NH(Et), $N(Et)_2$, $N(^iPr)_2$, NEt($^i$Pr), pyrrolidinyl, piperidinyl or morpholinyl;

or a salt thereof.

4. A compound according to claim 1 wherein $R_1$ and $R_4$ both denote H;

or a salt thereof.

5. A compound of formula (Ia):

(Ia)

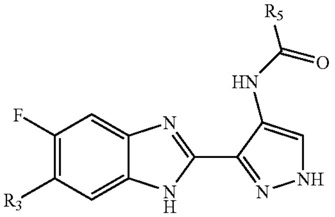

in which:

$R_3$ is $O(CH_2)_nN(Me)_2$ with n=2, 3 or 4, or $NH(CH_2)_2N(Me)_2$; and $R_5$ is NH($^i$Pr), NH(Et), $N(Et)_2$, $N(^iPr)_2$, NEt($^i$Pr), pyrrolidinyl, piperidinyl or morpholinyl;

or a salt thereof.

6. A compound as claimed in claim 5, wherein $R_3$ is $O(CH_2)_3N(Me)_2$, and $R_5$ is $N(Et)_2$ or piperidinyl;

or a salt thereof.

7. A compound according to claim 5 of formula (Ia) in which $R_3$ is $O(CH_2)_3N(Me)_2$;

or a salt thereof.

8. A compound according to claim 1 wherein $R_5$ is piperidin-1-yl;

or a salt thereof.

9. A compound according to claim 1 selected from the group consisting of:

3-{3-[6-(3-Dimethylaminopropoxy)-5-fluoro-1H-benzimidazol-2-yl]-1H-pyrazol-4-yl}-1,1-diethylurea;

N-{3-[6-(3-dimethylaminopropoxy)-5-fluoro-1H-benzimidazol-2-yl]-1H-pyrazol-4-yl}piperidine-1-carboxamide;

3-{3-[6-(2-Dimethylaminoethylamino)-5-fluoro-1H-benzimidazol-2-yl]-1H-pyrazol-4-yl}-1,1-diethylurea;

Cyclopropyl-3-{3-[6-(3-dimethylaminopropoxy)-5-fluoro-1H-benzimidazol-2-yl]-1H-pyrazol-4-yl}urea;

N-{3-[6-(3-Dimethylaminopropoxy)-5-fluoro-1H-benzimidazol-2-yl]-1H-pyrazol-4-yl}pyrrolidine-1-carboxamide;

1-{3-[6-(3-Dimethylaminopropoxy)-5-fluoro-1H-benzimidazol-2-yl]-1H-pyrazol-4-yl}-3-isopropylurea;

N-{3-[6-(3-Dimethylaminopropoxy)-5-fluoro-1H-benzimidazol-2-yl]-1H-pyrazol-4-yl}morpholine-4-carboxamide;

3-{3-[6-(3-Dimethylaminopropoxy)-5-fluoro-1H-benzimidazol-2-yl]-1H-pyrazol-4-yl}-1-isopropyl-1-methylurea;

1-tert-Butyl-3-{3-[6-(3-dimethylaminopropoxy)-5-fluoro-1H-benzimidazol-2-yl]-1H-pyrazol-4-yl}urea;

1-{3-[6-(3-Dimethylaminopropoxy)-5-fluoro-1H-benzimidazol-2-yl]-1H-pyrazol-4-yl}-3-isobutylurea;

3-{3-[6-(3-Dimethylaminopropoxy)-5-fluoro-1H-benzimidazol-2-yl]-1H-pyrazol-4-yl}-1,1-diisopropylurea;
3-{3-[6-(3-Dimethylaminopropoxy)-5-fluoro-1H-benzimidazol-2-yl]-1H-pyrazol-4-yl}-1,1-dipropylurea;
N-{3-[6-(3-Dimethylaminopropoxy)-5-fluoro-1H-benzimidazol-2-yl]-1H-pyrazol-4-yl}piperazine-1-carboxamide;
1-{3-[6-(3-Dimethylaminopropoxy)-5-fluoro-1H-benzimidazol-2-yl]-1H-pyrazol-4-yl}-3-ethylurea;
3-{3-[6-(3-Dimethylaminopropoxy)-5-fluoro-1H-benzimidazol-2-yl]-1H-pyrazol-4-yl}-1-ethyl-1-isopropylurea;
N-{3-[6-(3-Dimethylaminopropoxy)-5-fluoro-1H-benzimidazol-2-yl]-1H-pyrazol-4-yl}-4-methylpiperazine-1-carboxamide;

or a salt thereof.

10. A pharmaceutical composition comprising a compound according to claim 1, or a salt thereof, in combination with a pharmaceutically acceptable excipient.

11. A compound of formula (I) according to claim 1, wherein $R_3$ is $O(CH_2)_nN(Me)_2$, with n=2, 3 or 4; or a salt thereof.

12. A compound of formula (I) according to claim 1, wherein $R_3$ is $NH(CH_2)_2N(Me)_2$; or a salt thereof.

13. A compound of formula (Ia) according to claim 5, wherein $R_3$ is $O(CH_2)_2N(Me)_2$, with n=2, 3 or 4; or a salt thereof.

14. A compound of formula (Ia) according to claim 5, wherein $R_3$ is $NH(CH_2)_2N(Me)_2$; or a salt thereof.

* * * * *

UNITED STATES PATENT AND TRADEMARK OFFICE

CERTIFICATE OF CORRECTION

PATENT NO. : 9,126,969 B2
APPLICATION NO. : 12/338176
DATED : September 8, 2015
INVENTOR(S) : Marie-Pierre Cherrier et al.

It is certified that error appears in the above-identified patent and that said Letters Patent is hereby corrected as shown below:

In the Claims:

At column 83, claim number 13, line number 26, please replace "$O(CH_2)_2N(Me)_2$" with --$O(CH_2)_nN(Me)_2$--.

Signed and Sealed this
Fifteenth Day of March, 2016

Michelle K. Lee
*Director of the United States Patent and Trademark Office*